(12) United States Patent
Harp

(10) Patent No.: US 7,837,700 B2
(45) Date of Patent: *Nov. 23, 2010

(54) DRIVE APPARATUS

(75) Inventor: Richard J. Harp, Carlsbad, CA (US)

(73) Assignee: Surgitech, LLC, Charlotte, NC (US)

( * ) Notice: Subject to any disclaimer, the term of this patent is extended or adjusted under 35 U.S.C. 154(b) by 1350 days.

This patent is subject to a terminal disclaimer.

(21) Appl. No.: 11/269,231

(22) Filed: Nov. 8, 2005

(65) Prior Publication Data

US 2006/0079919 A1 Apr. 13, 2006

Related U.S. Application Data

(63) Continuation of application No. 10/675,068, filed on Sep. 29, 2003, now Pat. No. 7,390,330.

(60) Provisional application No. 60/414,690, filed on Sep. 27, 2002.

(51) Int. Cl.
*A61B 17/32* (2006.01)
(52) U.S. Cl. .......................... 606/171; 606/85
(58) Field of Classification Search ................ 606/85, 606/171, 177, 170
See application file for complete search history.

(56) References Cited

U.S. PATENT DOCUMENTS

| | | | |
|---|---|---|---|
| 3,642,002 A | 2/1972 | Otterstrom | |
| 3,857,240 A * | 12/1974 | McIntyre | .................... 60/221 |
| 3,978,862 A | 9/1976 | Morrison | |
| 4,262,501 A * | 4/1981 | Vaughn et al. | ................ 464/36 |
| 4,867,155 A | 9/1989 | Isaacson | |
| 4,891,884 A | 1/1990 | Torbet | |
| 5,092,873 A | 3/1992 | Simpson et al. | |
| 5,103,642 A | 4/1992 | Suzuki | |
| 5,222,966 A | 6/1993 | Perkins et al. | |
| 5,411,513 A | 5/1995 | Ireland et al. | |
| 5,540,693 A | 7/1996 | Fisher | |

(Continued)

FOREIGN PATENT DOCUMENTS

EP 0 716 831 3/1999

(Continued)

OTHER PUBLICATIONS

K. Tomita, MD, Ph.D. and N. Kawahara, MD, Ph.D.; The Threadwire Saw; a New Device for Cutting Bone; The Journal of Bone and Joint Surgery; Dec. 1996; vol. 78-A (12); pp. 1915-1917.

(Continued)

*Primary Examiner*—Michael J Milano
*Assistant Examiner*—Victor X Nguyen
(74) *Attorney, Agent, or Firm*—Knobbe, Martens, Olson & Bear, LLP

(57) ABSTRACT

The invention relates to shielded reciprocating surgical file system for precisely removing bone and/or other tissue material. The system allows a user to maneuver the system and navigate into hard to access sites under a direct vision mechanism included in the system. A transmission mechanism converts rotary motion from a motor into reciprocating motion and provides it to the surgical file for precision bone and/or tissue removal. A pulsatile pump mechanism is operatively coupled with the transmission mechanism and provides irrigating fluid to the surgical site.

32 Claims, 41 Drawing Sheets

U.S. PATENT DOCUMENTS

| | | | |
|---|---|---|---|
| 5,643,304 | A | 7/1997 | Schechter et al. |
| 5,784,923 | A | 7/1998 | Kuehnle |
| 5,846,244 | A | 12/1998 | Cripe |
| 6,001,115 | A | 12/1999 | Ahola et al. |
| 6,048,345 | A | 4/2000 | Berke et al. |
| 6,309,106 | B1 | 10/2001 | Hooley |
| 6,860,886 | B1 | 3/2005 | Lee |
| 7,390,330 | B2 * | 6/2008 | Harp .................... 606/171 |
| 2004/0122459 | A1 | 6/2004 | Harp |
| 2006/0058732 | A1 | 3/2006 | Harp |
| 2006/0161189 | A1 | 7/2006 | Harp |
| 2006/0200153 | A1 | 9/2006 | Harp |
| 2006/0200154 | A1 | 9/2006 | Harp |
| 2006/0200155 | A1 | 9/2006 | Harp |
| 2006/0206117 | A1 | 9/2006 | Harp |
| 2008/0058820 | A1 | 3/2008 | Harp |

FOREIGN PATENT DOCUMENTS

| | | |
|---|---|---|
| EP | 0716831 | 3/1999 |
| JP | 2002-177317 | 6/2002 |
| WO | WO 89/09028 | 10/1989 |
| WO | WO89/09028 | 10/1989 |
| WO | WO 99/39724 | 8/1999 |
| WO | WO99/39724 | 8/1999 |
| WO | WO01/08571 | 2/2001 |
| WO | WO 01/13802 | 3/2001 |
| WO | WO01/13802 | 3/2001 |
| WO | WO01/66021 | 9/2001 |
| WO | WO 01/66021 | 9/2001 |
| WO | WO 02/36023 | 5/2002 |
| WO | WO02/36023 | 5/2002 |
| WO | WO2004/002331 | 1/2004 |
| WO | WO2004/080316 | 9/2004 |

OTHER PUBLICATIONS

Jeong Tae Kim, M.D., Ph.D. and Seok Kwun Kim, M.D. Ph.D.; Endoscopically Assisted, Intraorally Approached Corrective Rhinoplasty; Department of Plastic and Reconstructive Surgery at the Dong-A-University College of Medicine and Institute of Medical Science; Jul. 2001; vol. 108, No. 1; pp. 199-205.

K. Tomita, Md, Ph.D. and N. Kawahara, MD, Ph.D.; *The Threadwire Saw: a New Device for Cutting Bone; The Journal of Bone and Joint Surgery*; Dec. 1996; vol. 78-A (12); pp. 1915-1917.

Jeong Tae Kim, MD, Ph.D. and Seok Kwun Kim, MD, Ph.D.; *Endoscopically Assisted, Intraorally Approached Corrective Rhinoplasty, Department of Plastic and Reconstructive Surgery at the Dong-A-University College of Medicine and Institute of Medical Science*; Jul. 2001; vol. 108, No. 1; pp. 199-205.

The PCT International Search Report from a counterpart International Application.

* cited by examiner

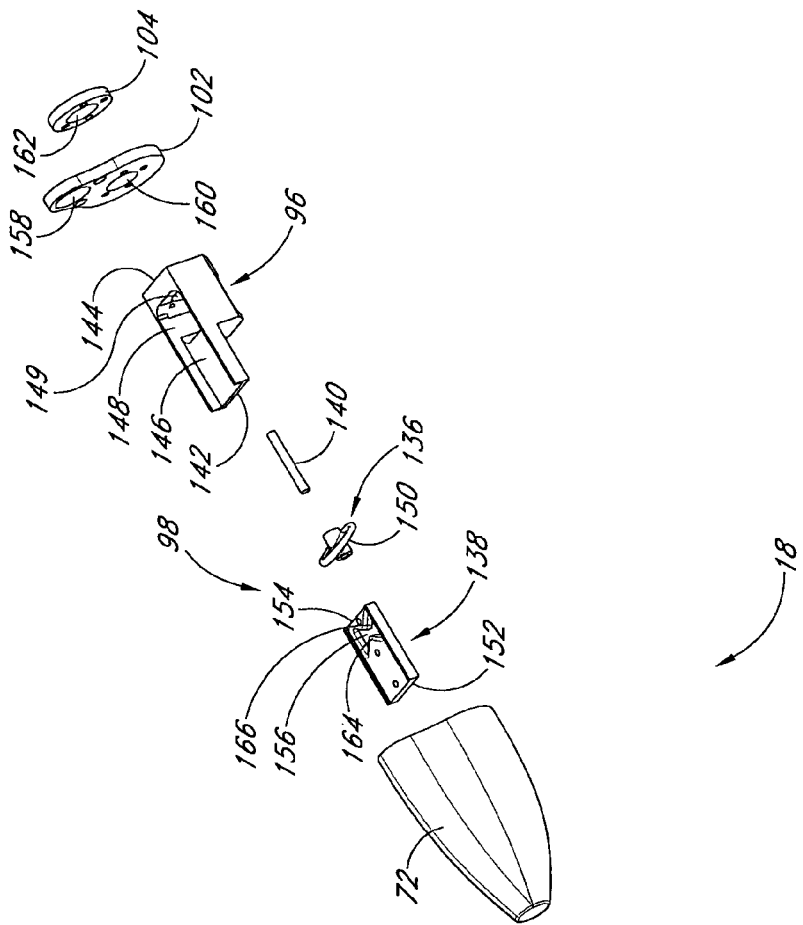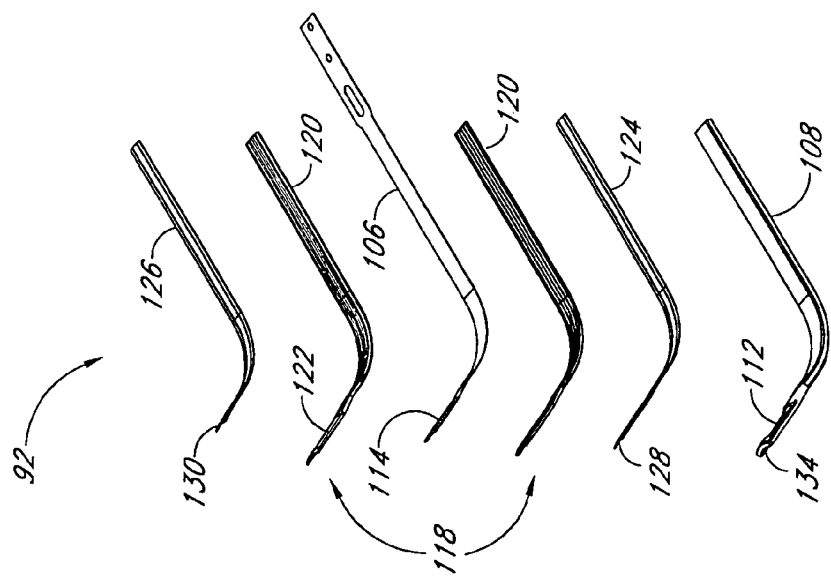
FIG. 9

DRIVE APPARATUS

RELATED APPLICATIONS

This application is a continuation of U.S. patent application Ser. No. 10/675,068 filed Sep. 29, 2003 now U.S. Pat. No. 7,390,330, entitled SHIELDED RECIPROCATING SURGICAL FILE and also claims priority from U.S. Provisional Application No. 60/414,690 filed Sep. 27, 2002, entitled SHIELDED RECIPROCATING SURGICAL FILE, the entireties of which are hereby incorporated by reference herein.

BACKGROUND OF THE INVENTION

1. Field of the Invention

The invention relates generally to systems and methods for tissue cutting and removal. More particularly, the invention relates to a shielded reciprocating surgical file system for cutting, removing, grinding, shaping and sculpturing bone and/or tissue material under direct vision.

2. Description of the Related Art

Adjacent spinal vertebrae are spaced by intervertebral discs that are tough and semi-elastic. The discs act as a flexible spacer between the vertebrae that makeup the backbone. Vertebrae are shaped to provide a bony tubular shaped tunnel between upper and lower pairs of vertebrae and this tunnel is made-up in part by the spacing disc. These tubular shaped tunnels are called neuroforamen and serve as a passageway for nerve roots. The size of the neuroforamen tubular shaped tunnels is a close fit for the nerve roots that pass through these tunnels on their way from the spinal cord to the arms, legs and other muscles.

Each year millions of people encounter neck and back injuries. Many million suffer from truly problematic back pain that either keeps them out of work or debilitates them in some way. Many vertebral and disc injuries result in pain from nerve irritation and compression.

When an intervertebral disc is damaged, often it is because of a physical overrotation between two vertebrae and normal wear and tear. When a vertebra is overrotated, small facet joints called the zygapophyseal capsules that are located to the left and right sides of the disc are damaged. When the body incurs damage to these small joints, unwanted osteophytes and bony overgrowths frequently occur at the edges of these tiny joints. The unwanted bony overgrowth restricts the neuroforamen and pinches the delicate and sensitive nerve roots.

Also, with age, for many people, the sensation of thirst is somewhat reduced. As a result, sometimes less water is consumed than needed by the body. The intervertebral discs depend on water as well as other materials to maintain a healthy function. When a disc looses a part of its fluid mass it is said to desiccate. When a disc is desiccated it reduces in height and reduces the space between the two vertebras it is connected to, that is, the neuroforamen becomes constricted and pinches nerve roots.

Pinched nerves that are constrained in between vertebras can cause neck and back pain. The bony overgrowth and a reduction in the space between vertebras pinch the nerves causing irritation, pain and numbness. The pinching can potentially result in a loss of use of the limbs controlled by the affected nerve.

Thus, when intervertebral discs are damaged from accident, age and/or general wear and tear the intervertebral nerve roots in the neuroforamen are irritated and pinched and can cause unwanted involuntary muscular contractions. The muscle contractions can come in the form of a continuous low-grade ache or become more severe as a spasm. The muscle contractions can act to further compress the space between the vertebras, which further pinches the nerve. This becomes a severely painful, self-destructive and self-feeding problem.

One current technology to treat a patient with nerve compression that causes pain and numbness involves the removal of the disc and fusion of the vertebra below with the vertebra above it. Vertebral fusion removes a disc that was flexible and fuses one vertebra together with the adjacent vertebra resulting in a rigid joint between two vertebrae. This causes added strain on the disc above and below the now rigid bone fusion. Sometimes the attempted fusion of one vertebra onto another vertebra is unsuccessful and does not provide the intended fusion.

Disadvantageously, the intervertebral fusion is an invasive and relatively complicated procedure. In addition, and undesirably, the fusion process can result in a long hospital stay for the patient, a long recuperation and rehabilitation period and high costs for both the patient and care providers.

SUMMARY OF THE INVENTION

Embodiments of the invention overcome some or all of the above disadvantages by providing systems and methods for tissue cutting and removal including a shielded reciprocating surgical file and a direct vision apparatus. Some embodiments provide surgical instrumentation that allows a surgeon to navigate into the tiny neuroforamen next to delicate nerves under direct vision, and locate and remove obstructions of tissue that can cause nerve compression and irritation. Advantageously, this offers many patients a minimally invasive surgical option that can result in shorter hospital stays and lower cost.

Embodiments of the invention can desirably be adapted and tailored to serve at least three surgical fields. These include, but are not limited to, neurosurgery, orthopaedic surgery and plastic surgery. The neurosurgical embodiments enable surgeons to safely enlarge the constricted neuroforamen and provide more space for the nerve roots to pass through the rigid bony vertebral structure, thereby relieving the nerve pinching and compression.

The orthopaedic embodiments provide improved bone and/or tissue removal instrumentation and methodology, for example, for orthopaedic surgical procedures such as knee surgery. The plastic surgery embodiments provide improved bone and/or tissue sculpturing instrumentation and methodology, for example, for cosmetic surgical procedures such as nose reshaping or rhinoplasty.

Some embodiments include a surgical instrument comprising a blade; a housing in which the blade moves, the housing having a long axis; a transmission that converts rotary motion to reciprocating, linear motion, wherein the transmission is coupled to the blade such that the blade moves reciprocally in the housing; a first opening in the housing through which a portion of the blade is exposed; and a cutting surface on the exposed portion of the blade, the surface configured to perform at least one of grinding, filing, and cutting of tissue.

In some embodiments the housing is concave about at least a portion of its long axis, such as at least a distal portion of its long axis. In some embodiments the housing is convex about at least a portion of its long axis, such as at least a distal portion of its long axis. In some embodiments the first opening is in an opening surface on the housing. In some embodiments the housing is curved along its long axis, to assist in placing the surgical instrument in the body of a patient. In some embodiments the blade is substantially flat.

In some embodiments the housing is curved along its long axis in a direction toward the opening surface. Some embodiments further comprise at least one bearing retainer for reducing friction. In some embodiments the at least one bearing retainer has at least one slot configured to transmit fluid toward a distal end of the instrument. Some embodiments further comprise at least one fiberoptic in or on the housing, for transmission of at least one of a video signal and illumination light. In some embodiments the housing has at least a second opening at a distal end of the housing.

Some embodiments further comprise at least two lenses coupled to the at least one fiberoptic. In some embodiments, at least one of the at least two lenses is disposed at a distal end of the housing, and another of the at least two lenses is disposed in proximity to the first opening in the housing. Some embodiments further comprise a pump for pumping fluid through the surgical instrument. In some embodiments the pump is mechanically coupled to the transmission. In some embodiments, the transmission comprises: two surfaces that are a substantially fixed distance apart; a cam that rotates about a central axis, the central axis being at an angle to a plane extending between the two surfaces; and the cam having a curvilinear body, the body having a nonuniform thickness, wherein the body continuously contacts the two surfaces as the cam rotates about the central axis, such that the two surfaces remain at the substantially fixed distance apart as they move linearly in response to the cam's rotation about the central axis.

In some embodiments, the cam's central axis is substantially parallel to a direction of the linear motion of the two surfaces. In some embodiments, the central axis is substantially perpendicular to the plane extending between the two surfaces. In some embodiments the two surfaces move linearly back and forth in reciprocating motion in response to the cam's rotation about the central axis. In some embodiments the curvilinear body has a shape comprising at least two toruses, the at least two toruses being partially superimposed, and each of the at least two toruses has a central axis, wherein the central axes of the at least two toruses are at an angle to each other. In some embodiments at least one bearing comprises the two surfaces. In some embodiments two bearings respectively comprise the two surfaces.

In some embodiments the curvilinear body is disposed at an angle to the central axis of the cam. Some embodiments include an apparatus for translating a rotary motion to a linear motion, the apparatus comprising: two surfaces that are a substantially fixed distance apart; and a cam that rotates about a central axis, the central axis being at an angle to a plane extending between the two surfaces; the cam having a curvilinear body, the body having a nonuniform thickness, wherein the body continuously contacts the two surfaces as the cam rotates about the central axis, such that the two surfaces remain at the substantially fixed distance apart as they move linearly in response to the cam's rotation about the central axis.

In some embodiments the cam's central axis is substantially parallel to a direction of the linear motion of the two surfaces. In some embodiments the central axis is substantially perpendicular to the plane extending between the two surfaces. In some embodiments the two surfaces move linearly back and forth in reciprocating motion in response to the cam's rotation about the central axis. In some embodiments the curvilinear body has a shape comprising at least two toruses, the at least two toruses being partially superimposed, and each of the at least two toruses has a central axis, wherein the central axes of the at least two toruses are at an angle to each other.

In some embodiments at least one bearing comprises the two surfaces. In some embodiments two bearings respectively comprise the two surfaces. In some embodiments the curvilinear body is disposed at an angle to the central axis of the cam. Some embodiments include a pump comprising: a fluid path; two plungers configured to at least partially occlude the fluid path; a cam configured to cause the two plungers to at least partially occlude the fluid path alternatingly; and at least one check valve along the fluid path for reducing backflow of fluid within the fluid path.

In some embodiments the cam translates in a direction that is substantially perpendicular to a long axis of at least one of the two plungers. In some embodiments the cam translates in a direction that is substantially perpendicular to a long axis of each of the two plungers. In some embodiments the pump comprises: a fluid path; two plungers configured to at least partially occlude the fluid path; a cam configured to cause the two plungers to at least partially occlude the fluid path alternatingly; and at least one check valve along the fluid path for reducing backflow of fluid within the fluid path.

In some embodiments the cam translates in a direction that is substantially perpendicular to a long axis of at least one of the two plungers. In some embodiments the cam translates in a direction that is substantially perpendicular to a long axis of each of the two plungers. Some embodiments of the instrument further comprise at least one opening in the exposed portion of the blade, for transmitting fluid. In some embodiments the cutting surface comprises an abrasive material. In some embodiments the cutting surfaces comprises diamond. In some embodiments the blade comprises stainless steel.

Some embodiments further comprise a handpiece coupled to the housing. Some embodiments further comprise a video camera. In some embodiments the camera is configured to couple with a fiberoptic that extends to a distal end of the housing. In some embodiments a video camera is located in the handpiece. Some embodiments further comprise a watertight seal in the handpiece. In some embodiments the handpiece is configured to contain the video camera in a chamber such that the watertight seal reduces or prevents ingress of at least one of water and bacteria from outside the handpiece into the chamber containing the video camera in the handpiece.

Some embodiments further comprise a motor in the handpiece, the motor configured to power the rotary motion. In some embodiments the motor comprises a gas turbine. Some embodiments further comprise a cord configured to couple to a proximal end of the surgical instrument, the cord comprising at least one of a fiberoptic, an electrical line, an irrigation channel, a suction line, and a gas tube for powering a gas turbine motor in the surgical instrument.

For purposes of summarizing the invention, certain aspects, advantages and novel features of the invention have been described herein above. Of course, it is to be understood that not necessarily all such advantages may be achieved in accordance with any particular embodiment of the invention. Thus, the invention may be embodied or carried out in a manner that achieves or optimizes one advantage or group of advantages as taught or suggested herein without necessarily achieving other advantages as may be taught or suggested herein.

All of these embodiments are intended to be within the scope of the invention herein disclosed. These and other embodiments of the invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention and some of its features and advantages, certain preferred embodiments and modifications thereof will become apparent to those skilled in the art from the detailed description herein having reference to the figures that follow, of which:

FIG. 9 is a simplified exploded perspective view of the distal tip assembly of FIG. 8 illustrating features and advantages in accordance with an embodiment of the invention.

DETAILED DESCRIPTION OF THE PREFERRED EMBODIMENTS

The preferred embodiments of the invention described herein relate generally to systems and methods for tissue cutting and removal and, in particular, to a shielded reciprocating surgical file system for cutting, removing, shaping and sculpturing bone and/or tissue material under direct vision.

While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described herein.

Figure 1:
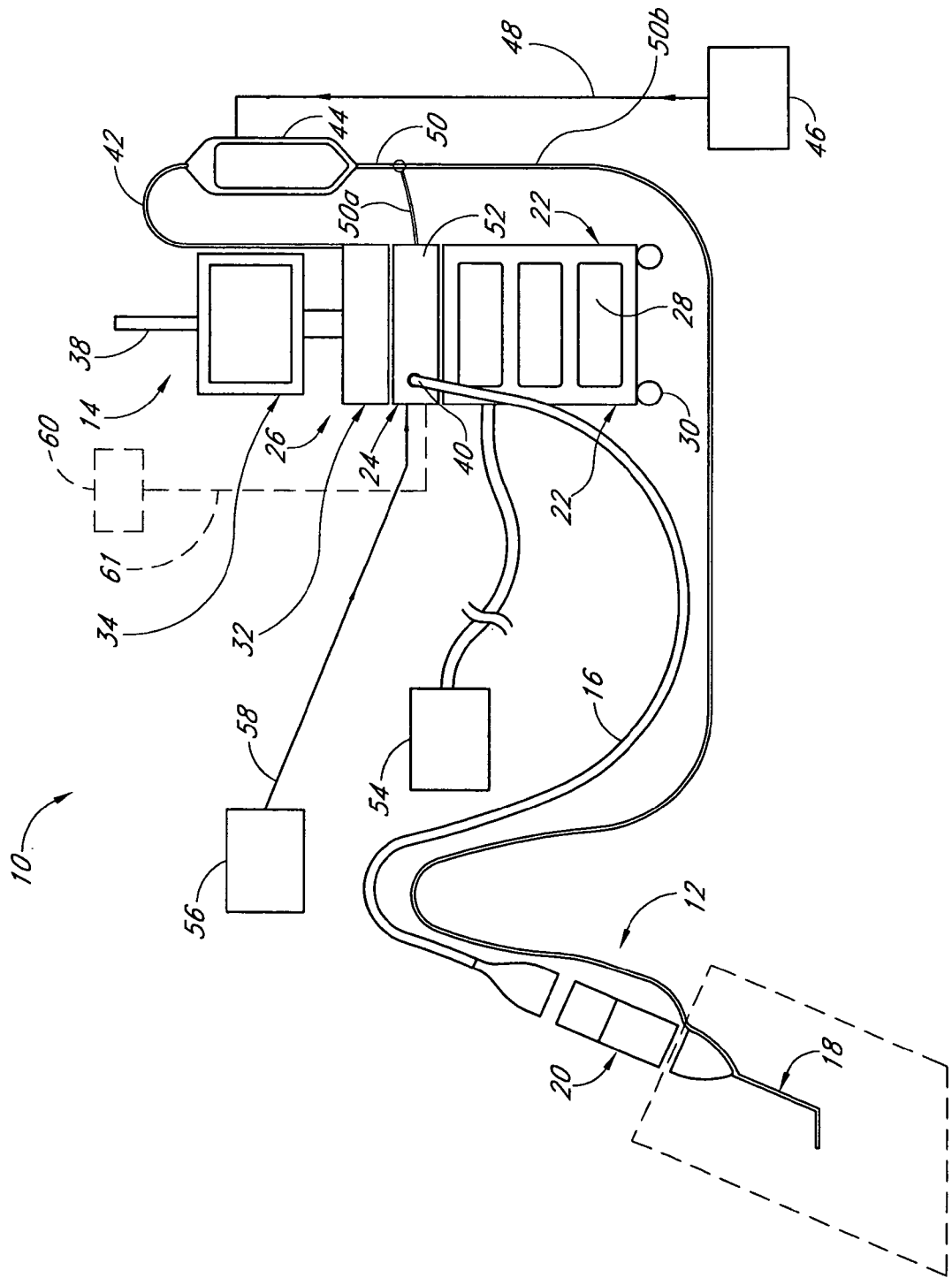
FIG. 1 is a simplified schematic view of a surgical file system illustrating features and advantages in accordance with an embodiment of the invention.
Figure 2:
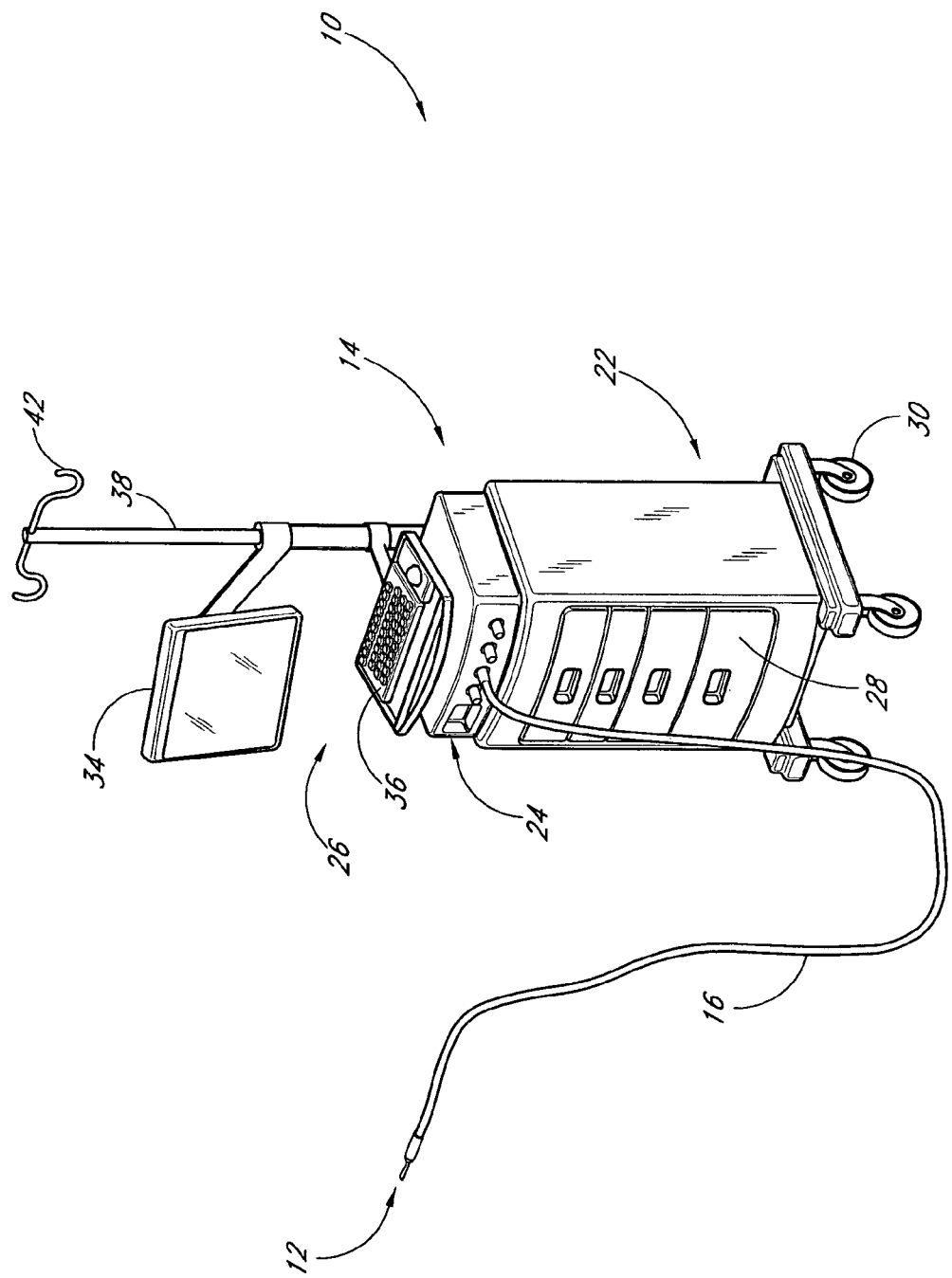
FIG. 2 is a simplified perspective view of the surgical file system of FIG. 1.

FIGS. 1 and 2 show a surgical file system 10 generally comprising a motorized reciprocating shielded surgical file instrument, apparatus, assembly or device 12 and a mobile portable control system 14 connected via a flexible umbilical cable 16. The surgical file device 12 generally comprises a distal tip assembly 18 and a powered handpiece 20. Reciprocating as used herein generally includes back and forth motion and to and from motion.

The system 14 generally comprises a mobile portable stand, cabinet or trolley 22 that supports a controller or control unit or box 24 and a computer system 26. In on embodiment, the system 14 has a footprint of about 0.2 m$^2$ (2 square feet (ft$^2$)) and a height of about 1.8 m (6 feet (ft)). In modified embodiments, other suitable dimensions may be efficaciously used, as needed or desired. The system 14 may also utilize wireless communication.

The cabinet 22 has a plurality of drawers or compartments 28 to store system parts, including spare parts, such as cables, connection lines, powered hand piece 20 and an array of various disposable distal cutting tip assemblies, for example, for neurosurgery, orthopaedic surgery and plastic surgery. The storage drawers 28 also serve to store instructions.

The cabinet 22 has a plurality of wheels 30 such as caster wheels to enable movement of the system 14. In the illustrated embodiment, the cabinet 22 has four wheels 30. The caster wheels 30 have wheel locks or other suitable fastening mechanisms to enable stationarily locking the unit at the desired position in the operating room or other area.

The computer system 26 comprises a central processing unit (CPU) 32, a monitor 34, a keyboard 36 including a mouse and a color printer to produce color pictures. The CPU 32 may be supported on (see, for example, FIG. 1) or within (see, for example, FIG. 2) the movable cabinet 22. The CPU 32 includes a video processing system, such as but not limited to a data acquisition board and the like, to process video signals from the surgical file device 12 and supply the signals to the monitor or video display 34. The CPU 32 has a printer port to interface it with the color printer.

The display monitor 34 can comprise any one of a number of suitable commercially available monitors. In one embodiment, the display 34 is a 17-inch (43 cm) liquid crystal display (LCD) monitor.

The storage cabinet 22 includes a substantially vertical pole or rod 38 to support the monitor 34. The height and tilt angle of the display 34 is adjustable to allow suitable viewing for the operating surgeons. In one embodiment, the monitor 34 is positioned at a height of about 1.5 meters (5 feet). As discussed further below, the monitor 34 can display a magnified visual picture of the view from the distal end of the cutting tip assembly 18.

The cabinet 22 includes one or more hooks or supports 42 for mounting of an irrigation fluid bag, container or pouch 44. The hooks 42 can be positioned at a suitable position, for example, on the pole 38. The irrigation bag 44 is provided sterile irrigation water from a source 46 through a feedline 48. The sterile water is transported to the distal cutting tip assembly 18 during device operation through feed line 50.

In one embodiment, sterile water is provided to the distal cutting tip assembly 18 through the control unit 24 via feedline 50a. In a modified embodiment, the sterile water is provided directly to the distal cutting tip assembly 18 via feedline 50b.

The control unit 24 is supported at a suitable working height by the cabinet structure 22. The control unit 24 is operatively interfaced or connected the cable 16 at its proximal end 40. In the illustrated embodiment, the cable 16 connects to a front face 52 of the control box 24. The control box 24 and the CPU 32 can be housed in a single unit.

The control unit 24 and the computer system 26 are powered by a conventional 115-Volt AC electrical power supply 54, for example, by connecting a male plug to a wall receptacle. In modified embodiments, the system may be powered by a portable power supply such as a generator and the like.

In one embodiment, the control unit 24 connects to a pressurized gas or air source supply 56 via feedline 58. As discussed further below, the pressurized gas is used to power an air turbine motor of the powered handpiece 20. The pressurized gas is supplied by the hospital or house supply. In modified embodiments, a portable pressurized gas source such a cylinder may be efficaciously used, as needed or desired.

In one embodiment, the pressurized gas and the irrigation water are supplied from the control unit 24 and through the umbilical cable 16 to the surgical file device 12. In addition, the cable 16 provides video signals from the surgical file device 12 to the control unit 24 and computer system 26. The umbilical cable 16 provides a mechanical and waterproof connection for electrical, video, pressurized gas and irrigation water supply. In modified embodiments, one or more of the electrical and video signals, gas and water may be transmitted through separate cables with efficacy, as needed or desired.

The cable 16 can be any suitable length, for example, about 16 feet long. The cable 16 is sterilizable. The cable 16 may also be used to provide a suction line, as needed or desired.

The control box 24 houses switches and valves to control the flow of the pressurized gas and irrigation water. The control unit 24 has electrical controls for the handpiece 20 and video signals for the computer system 26. The control unit 24 may also include sensors such as pressure sensors, flow rate sensors and the like to monitor the flow of the pressurized gas and irrigation water.

Software is provided that interfaces with the control unit 24 to monitor and control system operation and perform various other related functions. For example, the software allows the operating room personnel to enter the patient identification and date and other pertinent data into the computer for record reference.

The software also allows operating room personnel to change video picture zoom ratios and to control and modify details of the picture for clarity. The computer based system enables the operating personnel to save pictures of the patient's anatomy, including before and after pictures, to a computer file and to print out color pictures in seconds.

The software is used to control the pressurized gas and irrigation liquid flow to the surgical file device 12. The software can also be used to turn the device 12 on and off and control the frequency of cutting blade reciprocation during filing procedures.

The control unit 24 accommodates connection to existing cauterizing equipment. As discussed further below, and as shown in phantom in FIG. 1, the control unit 24 can be connected to a cauterizing system 60 through connection line 61 to stop or prevent undesirable bleeding during surgery.

In brief, to enable the surgeon to stop the bleeding of freshly cut bone tissue, the cutting blade surface can feature an electrically conductive surface that is operatively connected to an electric circuit, for example, 60. This allows a controlled pulse of electricity to generate a small amount of heat applied directly onto the bone surface to coagulate the blood and stop the bleeding at the freshly cut bone surface only, while insulating delicate nerve roots from unwanted heat damage. The irrigation water also works in conjunction to assist in keeping heat precisely localized and preventing heat injury to the nearby delicate nerve roots and spinal cord.

Figure 3:
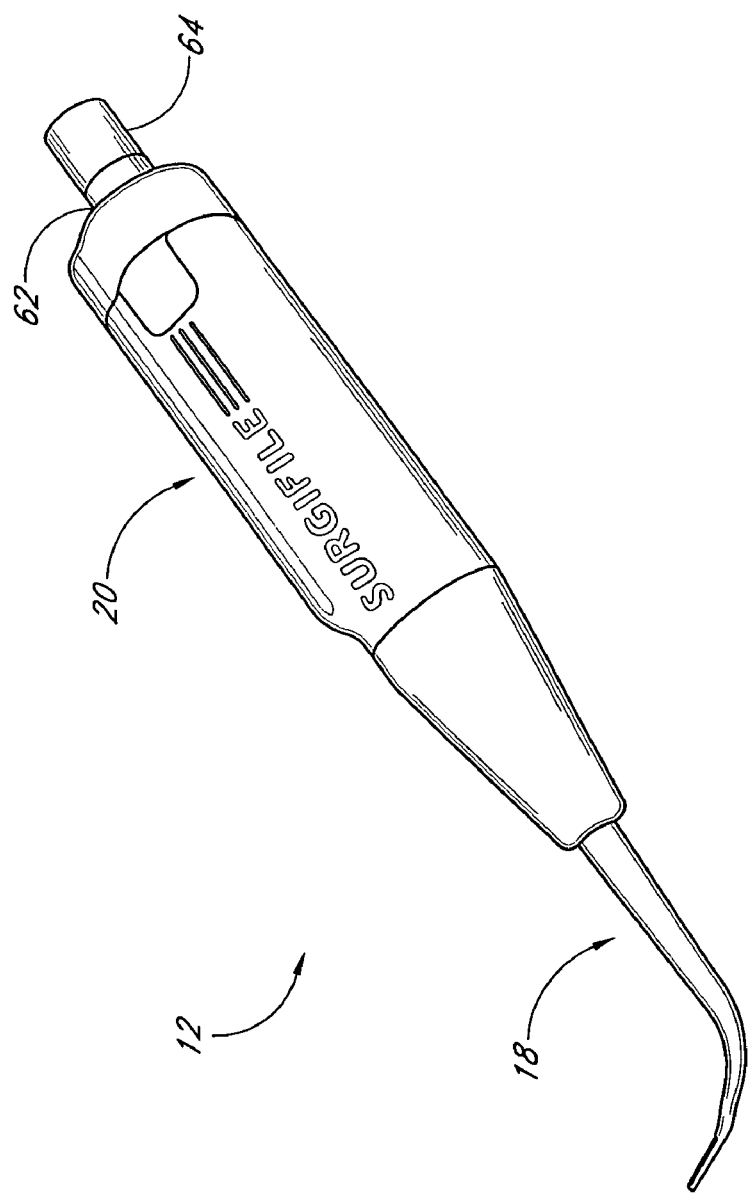
FIG. 3 is a simplified perspective view of a surgical file device with a curved distal tip configuration illustrating features and advantages in accordance with an embodiment of the invention.
Figure 4:
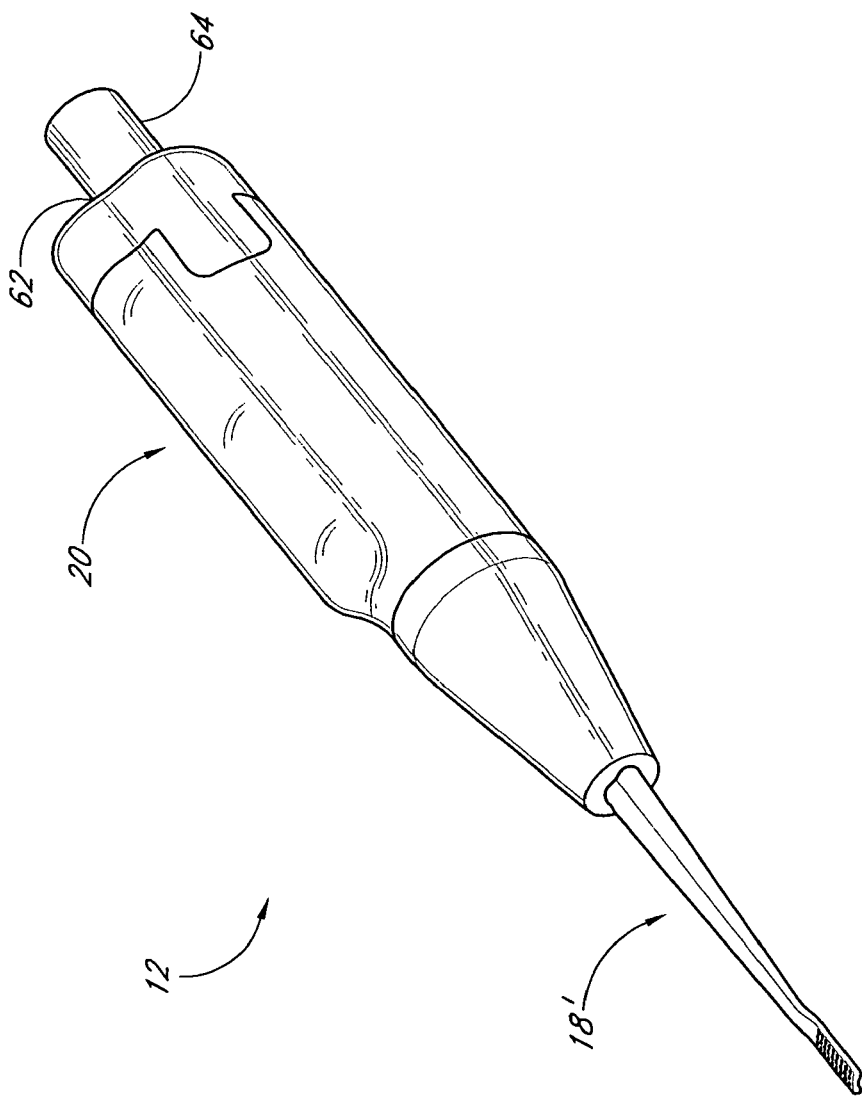
FIG. 4 is a simplified perspective view of a surgical file device with a straight distal tip configuration illustrating features and advantages in accordance with another embodiment of the invention.

FIG. 3 shows the surgical file device 12 with a distal tip assembly 18 having a generally curved and/or angled configuration. FIG. 4 shows the surgical file device 12 with a distal tip assembly 18' having a generally straight configuration. The powered handpiece 20 has at its proximal end 62 a quick connect docking feature 64 to enable connection to the umbilical cable 16 that provides a mechanical and waterproof connection for electrical, pressurized gas and irrigation water supply.

Figure 5:
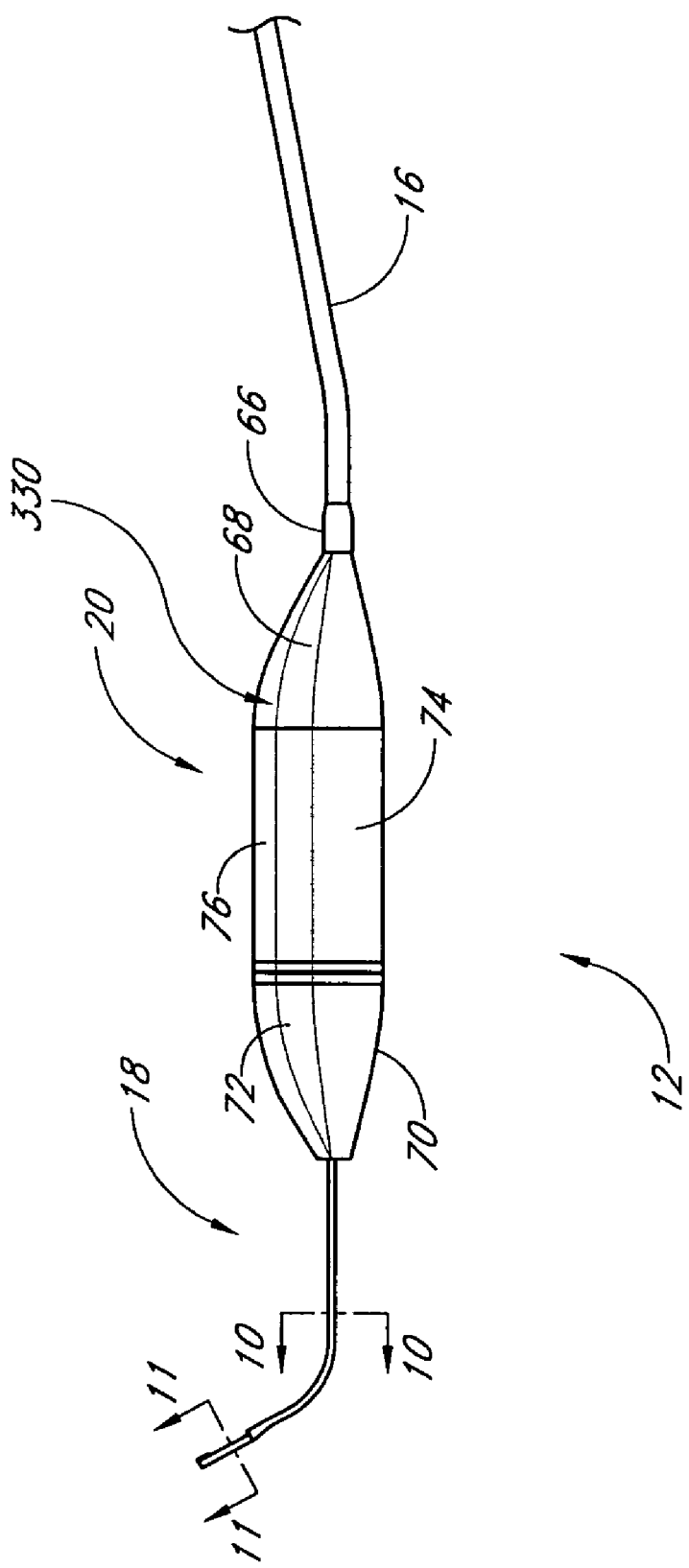
FIG. 5 is a simplified side view of a surgical file device illustrating features and advantages in accordance with an embodiment of the invention.

FIG. 5 shows the surgical file device 12 connected to the umbilical cable 16 at its distal end 66. The interface or connection between a proximal end 330 of the powered handpiece 18 and the cable 16 includes a cover or housing 68. In the illustrated embodiment, the cover 68 is generally frusto-conical in shape, though in modified embodiments other suitable shapes such as cylindrical and the like may be efficaciously utilized, as needed or desired.

The distal tip assembly 18 at its proximal portion or end 70 includes a cover or housing 72. In the illustrated embodiment, the cover 72 is generally frusto-conical in shape, though in modified embodiments other suitable shapes such as cylindrical and the like may be efficaciously utilized, as needed or desired.

The powered handpiece 20 includes a cover 74 intermediate the front and back covers 68 and 72. In the illustrated embodiment, the cover 74 is generally cylindrical in shape and can include a longitudinally extending bulging portion 76 for housing a video camera. In other embodiments, the cover 74 may be efficaciously contoured in suitable ergonomic shapes that facilitate operation by a surgeon or other operator.

The covers 68, 72, 74 can be formed from a number of suitably durable materials. In one embodiment, the covers 68, 72, 74 are formed from a suitable plastic such as a thermoplastic. In another embodiment, the covers 68, 72, 74 are formed from a suitable metal such as stainless steel. In modified embodiments, other suitable plastics, metals, alloys, ceramics, combinations thereof, among others, may be efficaciously utilized, as needed or desired. Suitable surface coatings or finishes may be applied, as required or desired.

The covers 68, 72, 74 can be fabricated by using a number of manufacturing techniques. These include, but are not limited to, molding, machining, casting, forging, laser cutting and/or processing, laminating, adhesively fixing, welding, combinations thereof, among others, with efficacy, as needed or desired.

Figure 6:
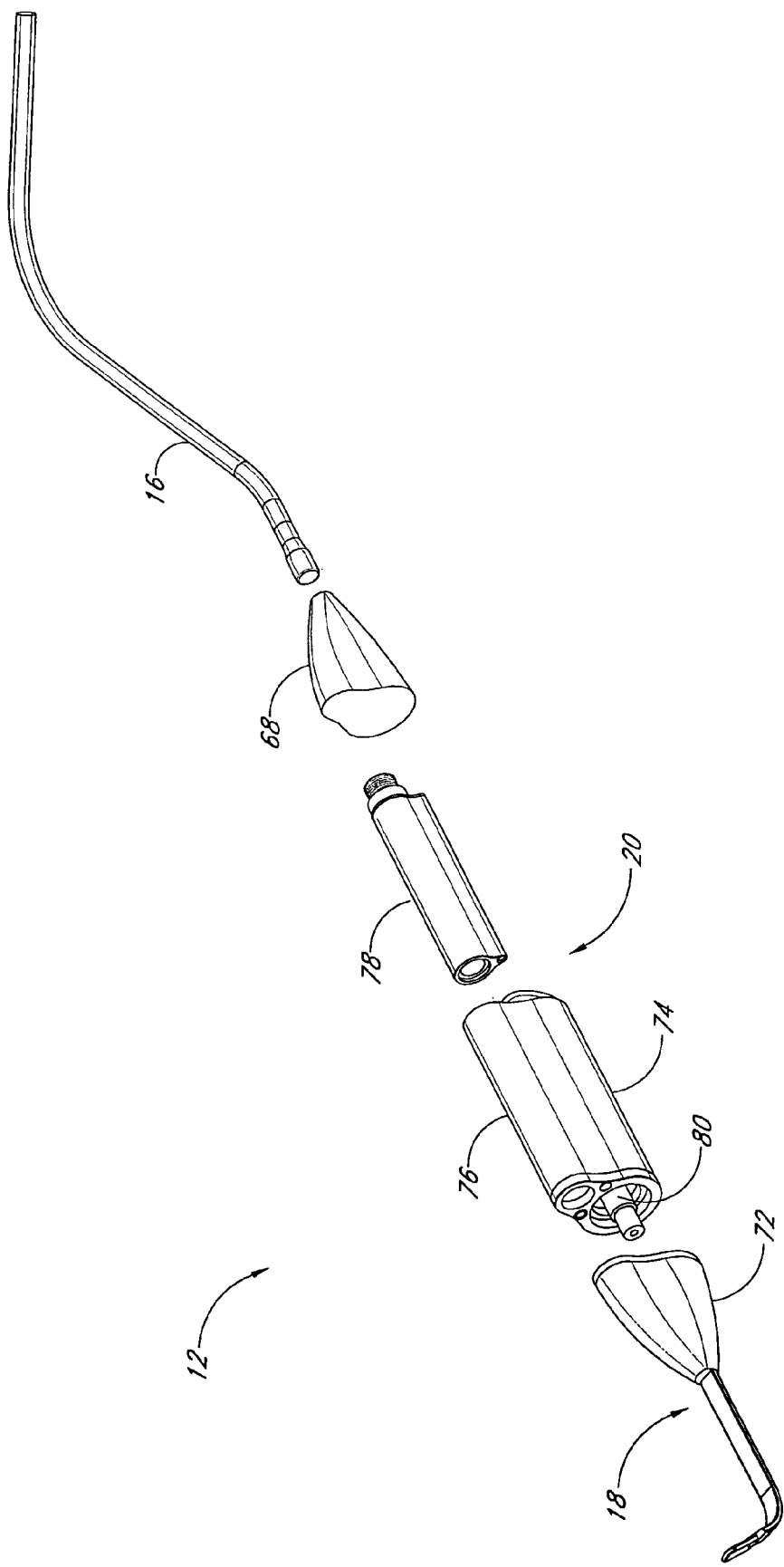
FIG. 6 is a simplified partially exploded view of the surgical file device of FIG. 5.
Figure 7:
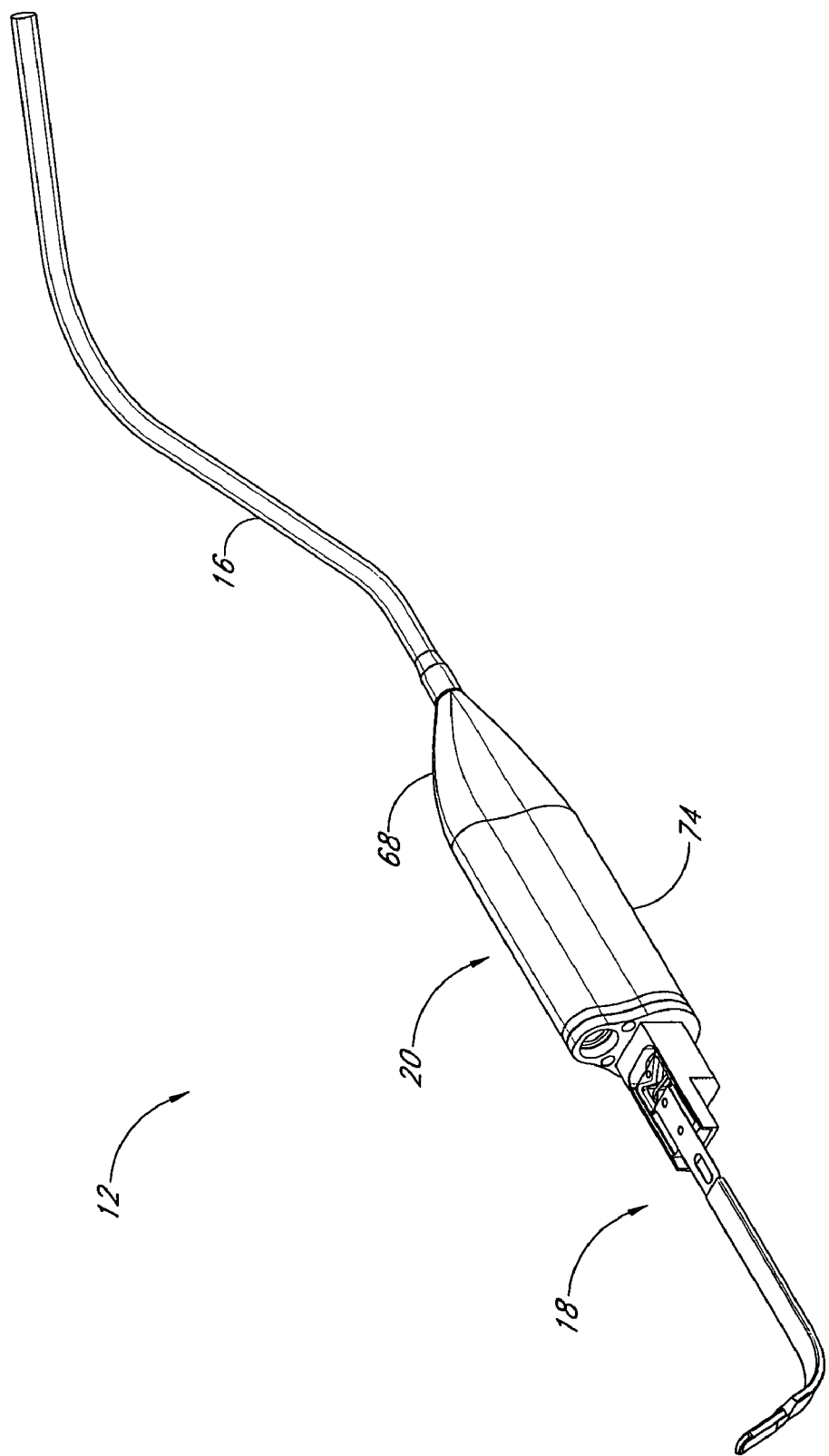
FIG. 7 is a simplified perspective view of the surgical file device of FIG. 5 with the distal cover removed illustrating features and advantages in accordance with an embodiment of the invention.

FIG. 6 shows a partially exploded view of the surgical file device 12. As discussed further below, the powered handpiece 20 includes a video camera 78 and a micro-motor 80 that provides rotary motion which is converted to linear reciprocating motion within the distal tip assembly 18. FIG. 7 shows another perspective view of the surgical file device 12 with the distal cover 72 removed illustrating some of the features of the distal tip assembly.

Distal Tip Assembly

Figure 8:
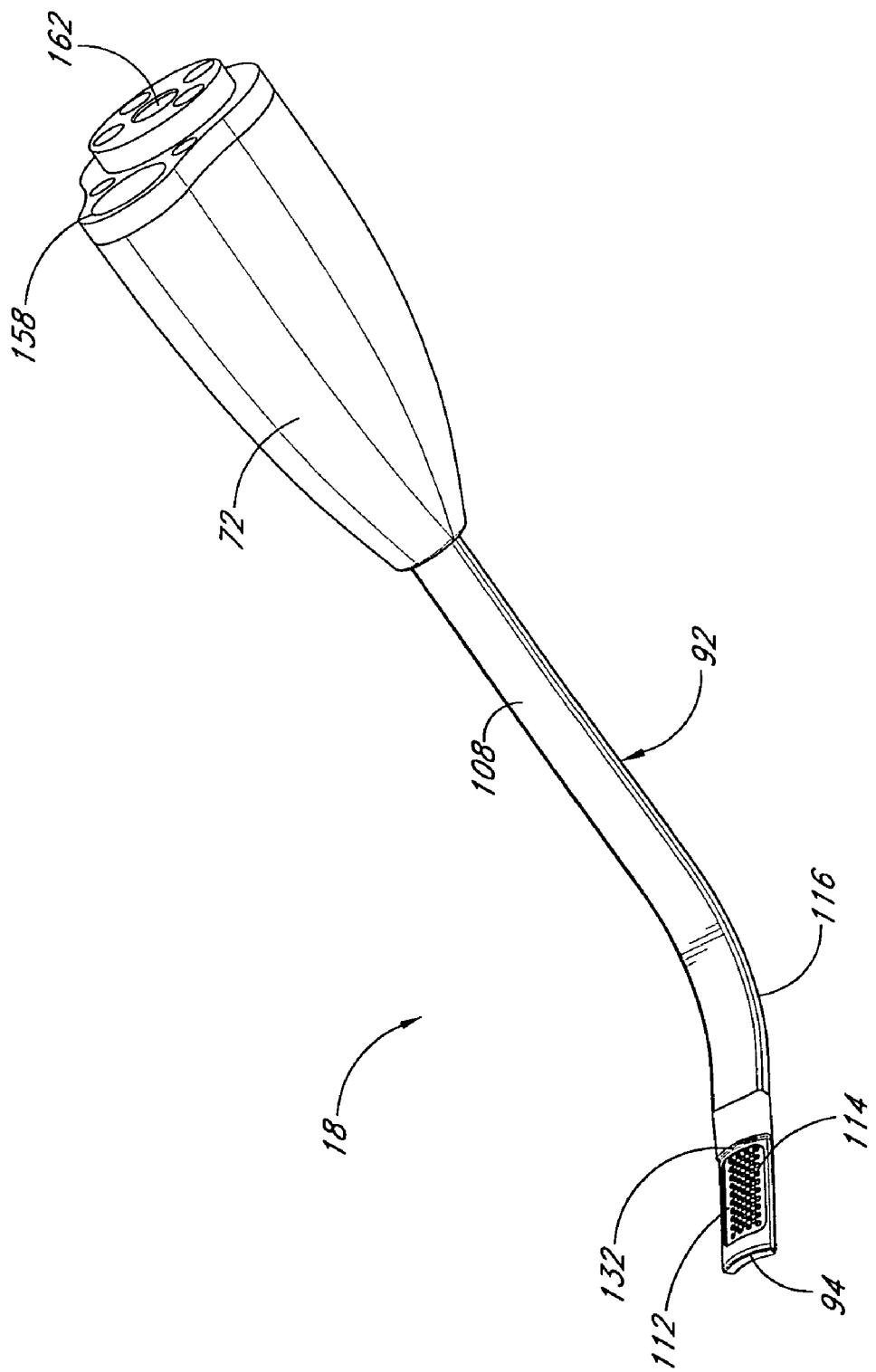
FIG. 8 is a simplified perspective view of a distal tip assembly of the surgical file device of FIG. 5.

FIGS. 8 and 9 show the distal tip assembly 18 in greater detail. In one embodiment, the composite tip 18 has a length of about 10 cm (4 inches) to about 15 cm (6 inches), including all values and sub-ranges therebetween. In one embodiment, the composite tip 18 has a length of about 5 cm (2 inches) to about 30 cm (12 inches), including all values and sub-ranges therebetween. In modified embodiments, other suitable lengths may be efficaciously utilized, as needed or desired.

The distal tip assembly 18 is sterile to maintain appropriate surgical standards and is provided in a sterile packaging. In one embodiment, the distal tip assembly 18 is for one time use and is disposable thereafter. As described further below, embodiments of the distal tip assembly 18 include a cartilage or other tissue and bone removal file with vision, illumination, irrigation and cauterization features.

The distal tip assembly 18 generally comprises a distal tip portion 92 that has a distal-most end 94 and a proximal portion extending into the cover 72 that encloses a housing 96 that receives a toroidal power converter system 98 and a water pump system. The distal tip assembly 18 further includes an interface member 102 and a coupling 104 that facilitate connection between the distal tip assembly 18 and the powered handpiece 20.

The distal tip portion 92 generally comprises a reciprocating cutting or filing blade 106 that is enclosed in a protective case or shield 108. The shield 108 has an aperture, window, opening 112 to expose a cutting surface 114 of the filing blade 106 proximate the distal end 94. Desirably, the shielded blade 106 permits surgical bone and/or tissue removal substantially without risk of damage to nearby delicate tissues such as nerve tissue.

The distal tip portion 92 can be configured to be small and thin so it is minimally intrusive and can go around corners and into any small inaccessible blind channels where nerves are located. The distal tip portion 92 can be configured to fit any desired cavity or contoured shape. The tip portion 92 can be supplied in a variety of sizes and shapes to suit a particular application such as, but not limited to, neurosurgery, orthopaedic surgery and plastic surgery.

The blade cutting surface 114 can be located on the end of an extension with a bend 116 of any desired angle. In the illustrated embodiment of FIGS. 8 and 9, the tip portion 92 has a curved, angled or bent configuration with the bend 116. In another embodiment, the distal tip portion 92 has a substantially straight and/or planar (flat) configuration.

The tip portion 92 further includes a linear bearing retainer 118 within the shield 108. The reciprocating blade 106 is precision fitted within the bearing retainer 118 that allows free linear motion of the reciprocation blade stroke. Advantageously, the bearing retainer 118 provides low friction bearing surfaces for the reciprocating motion of the blade 106.

The bearing retainer 118 comprises a plurality of stationary linear bearings 120 which are positioned on the top, bottom and both sides of the reciprocation blade. The top linear bearing 120 has an aperture, opening or window 122 that is substantially aligned with the shield aperture 112 to expose the blade cutting surface 114. In one embodiment, the tip portion 92 (and hence the lengths of the blade cutting surface 114 and the apertures 112, 122) are configured so that substantially the entire blade cutting surface 114 is exposed during the full blade reciprocation cycle.

The bearing retainer 118 can be formed from a number of suitably durable materials. In one embodiment, the bearing retainer 118 is formed from a suitable plastic such as a thermoplastic. In modified embodiments, other suitable plastics, metals, alloys, ceramics, combinations thereof, among others, may be efficaciously utilized, as needed or desired. Suitable surface coatings or finishes may be applied, as required or desired.

The bearing retainer 118 can be fabricated by using a number of manufacturing techniques. These include, but are not limited to, molding, machining, casting, forging, laser cutting and/or processing, laminating, adhesively fixing, welding, combinations thereof, among others, with efficacy, as needed or desired.

As described in more detail below, the distal tip portion 92 further includes a pair of fiber optic probes 124, 126 that are part of an on-board optical illumination and vision system. The fiber optic probes 124, 126 optically connect or interface at their proximal ends to the video camera 78.

The bottom or lower fiber optic probe 124 is below the lower bearing 120. The fiber optic probe 124 may be housed within the shield 108 or it may have its independent protective jacket below the shield 108. The fiber optic probe 124 has a distal end 128 at about the distal-most end 94 of the tip portion 92.

The top or lower fiber optic probe 126 is above the upper bearing 120. The fiber optic probe 126 may be housed within the shield 108 or it may have its independent protective jacket above the shield 108. The fiber optic probe 126 has a distal end 130 proximal to a proximal end 132 of the aperture 112 and/or the cutting surface 114.

The shield 108 can include the aperture 112 on any one of its sides depending on the positioning of the cutting surface 114. This includes the top (as shown in, for example, FIGS. 8 and 9), the bottom and the sides of the shield 108 and even its distal end 134. The shield 108 has a longitudinally extending cavity that houses the blade 106, the bearing retainer 118 and in some embodiments the fiber optic probes 124, 126. In the illustrated embodiment, the distal end 134 closes the longitudinal shield cavity.

In one embodiment, the shield 108 is capable of deflecting and bends at predetermined and/or low loads (for example about 2 lbs.) in order to prevent injury or damage to tissue, such as nerve tissue, engaged by the shield 108. The shield 108 has a predetermined stress-strain curve and spring constant to provide the desired deflection and can comprise, for example, a suitable polymer and the like. The shield 108 may bend at the bend location 116 or at a location proximate to the contact with the tissue. One or more of the associated tip portion 92 components such as the blade 106, bearings 120 and the fiber optic probes 124, 126 can also bend with the shield 108, as needed or desired.

The shield 108 can be formed from a number of suitably durable materials. In one embodiment, the shield 108 is formed from a suitable plastic such as a thermoplastic. In another embodiment, the shield 108 is formed from a polymer that is flexible or can bend under a predetermined load. In modified embodiments, other suitable plastics, metals, alloys, ceramics, combinations thereof, among others, may be efficaciously utilized, as needed or desired. Suitable surface coatings or finishes may be applied, as required or desired.

The shield 108 can be fabricated by using a number of manufacturing techniques. These include, but are not limited to, molding, machining, casting, forging, laser cutting and/or processing, laminating, adhesively fixing, welding, combinations thereof, among others, with efficacy, as needed or desired.

The shield 108, the bearing retainer 118 and the fiber optic probes 124, 126 generally conform in shape to the longitudinal profile of the blade 106. In the illustrated embodiment of FIGS. 8 and 9, this is a curved, angled or bent profile with a bend at around 116.

Figure 10:
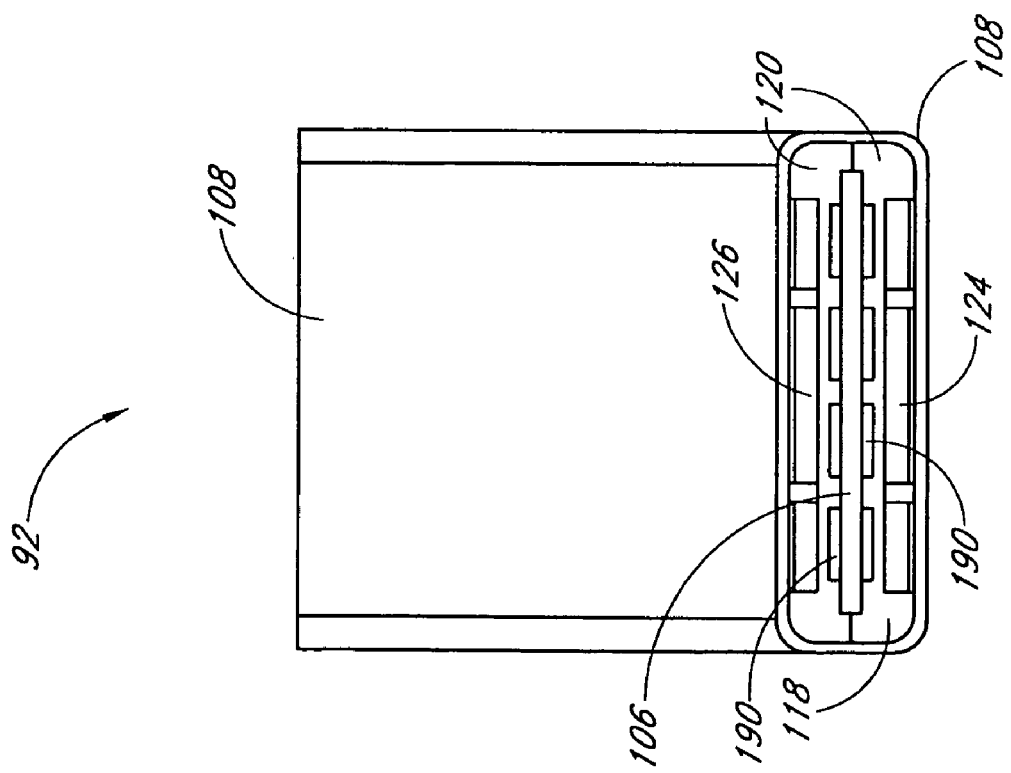
FIG. 10 is a sectional view along line 10-10 of FIG. 5 illustrating features and advantages in accordance with an embodiment of the invention.

FIG. 10 shows a cross-sectional view of the distal tip portion 92 at a location proximal to the aperture 112 and the bend 116. The blade 106 is substantially centrally located within the shield or outer jacket 108. The blade 106 is precision fitted within the bearing retainer 118 including the linear bearings 120. The respective lower and upper fiber optic probes 124, 126 are buffered from the blade 106 by the stationary bearings 120.

The cutting blade linear bearing 120 has a series of shallow slots 190 running substantially longitudinally in line with the proximal to distal axis. The slots 190 serve as water passageways to enable irrigation water to be transported from a proximal to a distal location. The irrigation water serves several functions and provides several advantages.

The water is a lubricant for the interface between the moving blade 106 and the stationary linear bearings 120, which in one embodiment are positioned on the top and bottom and both sides of the reciprocation blade 106. The water cools the blade and bearing material, and in the embodiment the bearing material is plastic, prevents the plastic bearing material from getting hot and softening. The water also serves to wet the cutting blade surface. The water is also used to clean tissue and transport the cut tissue away from the cutting blade 106. Additionally, water transported across the linear blade 106 intimately irrigates the volume of water in the distal blade area to clear the optical vision field for clear viewing.

Figure 11:
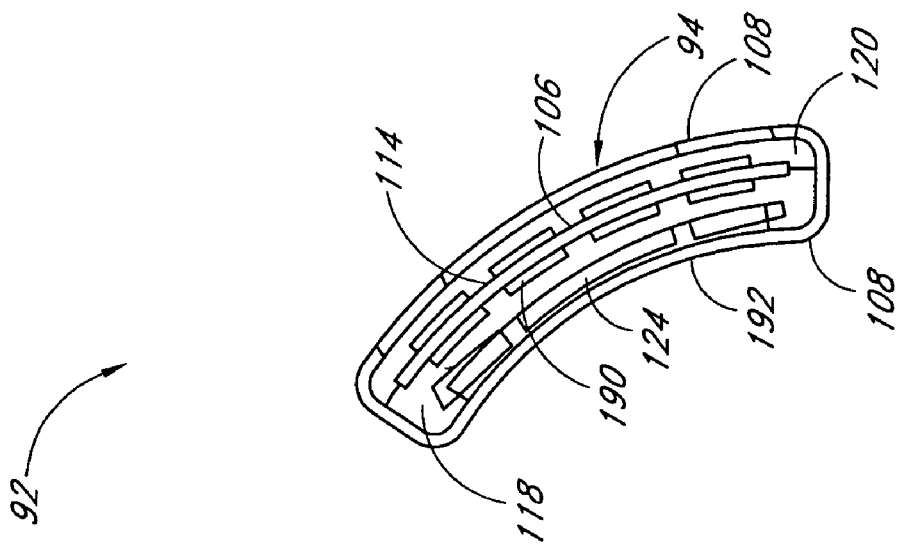
FIG. 11 is a sectional view along line 11-11 of FIG. 5 illustrating features and advantages in accordance with an embodiment of the invention.

FIG. 11 shows a cross-sectional view of the distal tip portion 92 at the shield aperture 112. The cutting surface 114 of the blade 106 is exposed and is above the lower bearing 120, the lower fiber optic probe 124 and a lower portion 192 of the shield 108. The drawing also shows portions of the shield 108 and the upper bearing 120 at the tip distal end 94. In this embodiment, the cross-sectional profile of the cutting surface 114 is convex and the associated portions of the shield 108, bearings 120 and lower fiber optic probe 124 generally conform to this shape.

In one embodiment, and as described further below, the toroidal drive system 98 is substantially mounted within the housing 96 and generally comprises a rotatable toroid drive 136 and a drive slide 138. A drive shaft 140 is connected to the handpiece motor 80 and transfers rotary motion to the toroid drive 136 which engages the linear slider 138 to convert rotary motion into reciprocating motion that is provided to the blade 106 for performing bone and/or tissue removal operations. In modified embodiments, other suitable rotary to reciprocating motion mechanisms or devices may be used, as needed or desired, to reciprocatingly drive the blade 106.

As discussed further below, the drive shaft 140 is connected to the toroid drive 136 and has a specially designed female receptor hole. The receptor hole allows the drive shaft 140 to substantially irrotationally mate with a power drive shaft of the motor 80.

The housing 96 has a distal end 142 and a proximal end 144 and a generally flat recessed surface 146 extending from the distal end 142 towards the proximal end 144. The linear slide 138 is reciprocatingly seated on or within the recessed surface 146. The housing 96 includes a cavity 148 intermediate the recessed surface 146 and the housing proximal end 144 that receives the rotatable toroid drive 136. The housing proximal end 144 has an opening 149 that receives a power shaft of the handpiece motor 80 that connects to the drive shaft 140.

The housing 96 can be formed from a number of suitably durable materials. In one embodiment, the housing 96 is formed from a suitable plastic such as a thermoplastic. In modified embodiments, other suitable plastics, metals, alloys, ceramics, combinations thereof, among others, may be efficaciously utilized, as needed or desired. Suitable surface coatings or finishes may be applied, as required or desired.

The housing 96 can be fabricated by using a number of manufacturing techniques. These include, but are not limited to, molding, machining, casting, forging, laser cutting and/or processing, laminating, adhesively fixing, welding, combinations thereof, among others, with efficacy, as needed or desired. The housing 96 and bearing retainer 118 may comprise an integral unit, for example, they may be formed by molding and the like.

The toroid drive 136 is connected with the drive shaft 140. The toroid drive 136 has an outer rim 150 that is engaged with the slider 138 and transmits rotary motion that is converted into reciprocating motion by the slider 138.

The slide plate 138 has a distal end 152, a proximal end 154 and a specially contoured slot 156 proximate to the proximal end 152 with a pair of generally opposed bearing surfaces 164, 166. As described in greater detail below, the slot 156 receives the rotating outer rim 150 of the toroid drive 136.

The blade 106 is connected to the slide 138. As described in greater detail below, this connection utilizes shear pins to provide a safety mechanism against blade buckling.

The slide 138 can be formed from a number of suitably durable materials. In one embodiment, the slide 138 is formed from a suitable plastic such as a thermoplastic. In modified embodiments, other suitable plastics, metals, alloys, ceramics, combinations thereof, among others, may be efficaciously utilized, as needed or desired. Suitable surface coatings or finishes may be applied, as required or desired.

The slide 138 can be fabricated by using a number of manufacturing techniques. These include, but are not limited to, molding, machining, casting, forging, laser cutting and/or processing, laminating, adhesively fixing, welding, combinations thereof, among others, with efficacy, as needed or desired.

The interface member 102 has an opening 158 which allows passage of the fiber optic probes 124, 126 for connection to the camera 78. The interface member 102 has an opening 160 that receives that receives a power shaft of the handpiece motor 80 that connects to the drive shaft 140.

The coupling 104 has an opening 162 that receives that receives a power shaft of the handpiece motor 80 that connects to the drive shaft 140. The openings 149, 160 and 162 are substantially aligned with one another.

The interface member 102 and coupling 104 can be formed from a number of suitably durable materials. In one embodiment, the interface member 102 and coupling 104 are formed from a suitable plastic such as a thermoplastic. In modified embodiments, other suitable plastics, metals, alloys, ceramics, combinations thereof, among others, may be efficaciously utilized, as needed or desired. Suitable surface coatings or finishes may be applied, as required or desired.

The interface member 102 and coupling 104 can be fabricated by using a number of manufacturing techniques. These include, but are not limited to, molding, machining, casting, forging, laser cutting and/or processing, laminating, adhesively fixing, welding, combinations thereof, among others, with efficacy, as needed or desired.

Blade Embodiments

Embodiments of the invention provide reciprocating cutting blade for precision bone and/or tissue removal. In one embodiment, the reciprocating cutting blade is shielded or covered or guarded on five sides to provide a shielded surgical file.

The shielded file can be flat, planar, convex or concave in its cross-section. The shielded file can extend generally straight or be curved, angled or bent along its longitudinal axis. Advantageously, the angled configuration allows the cutting surface to travel around a corner to reach into usually inaccessible body cavities. Desirably, this provides the ability to remove unwanted tissue in a blind tunnel or body cavity while enabling direct vision through the illumination and vision probes.

The shielded file can be dimensioned in a number of manners. The shielded file can be any length or width suitable for the human or mammalian anatomy proportions. For other non-medical applications, the shielded file can be of any length or width to suit the material removal application.

The thickness of the shielded file can be varied to be very thin. In one embodiment, the thickness can be of the order of $1/10^{th}$ of an inch. Advantageously, this enables the shielded file to fit into small spaces such as between a nerve and the foramen opening that it is passing through. In other embodiments, the thickness of the shielded file can be greater, as needed or desired.

The cutting blade can be shaped and contoured in several configurations. In one embodiment, the reciprocating cutting blade is straight and planer (in one flat plane). In another embodiment the reciprocating cutting blade that is curved convex or concave in its cross sectional shape. In yet another embodiment, the reciprocating cutting blade that is substantially straight in its longitudinal axis. In still another embodiment, the reciprocating cutting blade is curved in its longitudinal axis.

The thickness of the cutting blade drive 106 can be varied. In one embodiment, the cutting blade thickness is in the range from about 100 microns or μm (0.004 inches) to about 300 μm (0.012 inches). In another embodiment, the cutting blade thickness is in the range from about 50 μm (0.002 inches) to about 600 μm (0.024 inches). In yet another embodiment, the cutting blade thickness is in the range from about 25 μm (0.001 inches) to about 2.5 mm (0.1 inches). In modified embodiments, other suitable dimensions may be efficaciously utilized, as needed or desired.

The cutting blade 106 can be formed from a number of suitably durable materials. In one embodiment, the cutting blade 106 is formed from steel. In another embodiment, the cutting blade 106 comprises spring stainless steel. In modified embodiments, other suitable metals, alloys, plastics, ceramics, combinations thereof, among others, may be efficaciously utilized, as needed or desired. Suitable surface coatings or finishes may be applied, as required or desired.

The cutting blade 106 can be fabricated by using a number of manufacturing techniques. These include, but are not limited to, molding, machining, casting, forging, laser cutting and/or processing, laminating, adhesively fixing, welding, combinations thereof, among others, with efficacy, as needed or desired.

In one embodiment, the cutting blade 106 is flexible. Advantageously, this allows the cutting blade to be easily bent, angled or curved along its length as it is enclosed in a bent, angled or curved outer shield 108. In another embodiment, the cutting blade is substantially rigid. This can be suitable for blade configurations that are generally straight. The rigid blade may also be bent by suitable techniques, as needed or desired. In modified embodiments, the cutting blade 106 may efficaciously comprise one or more flexible portions and one or more rigid portions, as needed or desired.

Figure 12:
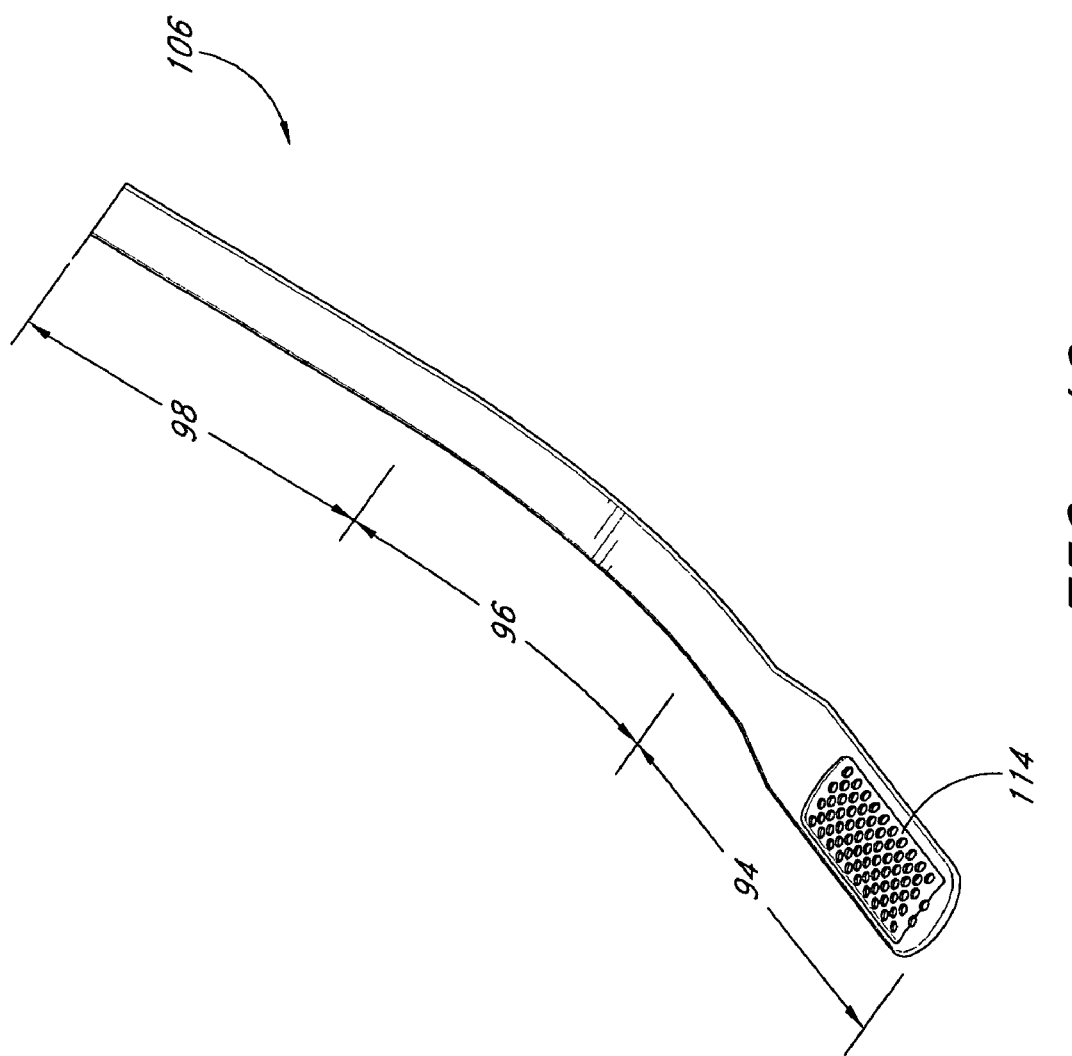
FIG. 12 is a simplified perspective view of a surgical cutting blade illustrating features and advantages in accordance with an embodiment of the invention.

FIG. 12 shows an embodiment of the cutting blade 106. The blade 106 comprises a thin flexible material that is capable of bending along its length. The blade 106 includes a distal section or portion 194 with the cutting surface 114, a medial section or portion 196 and a proximal section or portion 198. When enclosed within the curved, angled or bent shield 108 the blade 106 flexes like a thin spring to conform to the shape of the shield or guide cover 108. Thus, the medial section 196 is curved, angled or bent while the respective distal and proximal sections 194, 198 extend generally straight.

Figure 13:
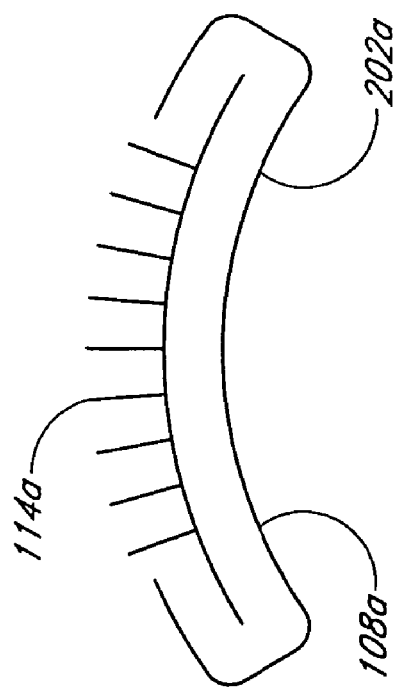
FIG. 13 is a simplified schematic cross-section view of a convex surgical file cutting surface illustrating features and advantages in accordance with an embodiment of the invention.

FIG. 13 shows a cross-section of a cutting surface 114a and an associated portion 202a of the shield 108a having a generally convex configuration suited for some particular bone and/or tissue removal applications. The convex curvature of the cutting surface 114a can also be advantageous in providing enhanced rigidity to the thin cutting surface 114a and/or the associated blade 106.

Figure 14:
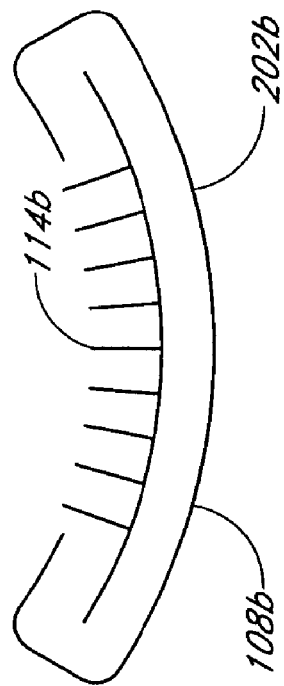
FIG. 14 is a simplified schematic cross-section view of a concave surgical file cutting surface illustrating features and advantages in accordance with another embodiment of the invention.

FIG. 14 shows a cross-section of a cutting surface 114b and an associated portion 202b of the shield 108b having a generally concave configuration suited for particular bone and/or tissue removal applications. The concave curvature of the cutting surface 114b can also be advantageous in providing enhanced rigidity to the thin cutting surface 114b and/or the associated blade 106.

Figure 15:
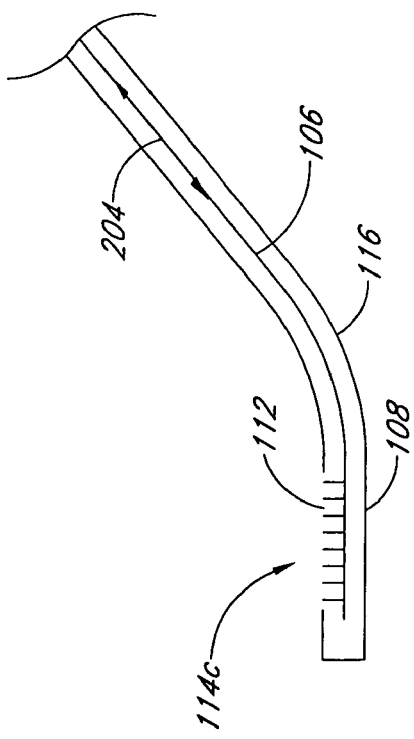
FIG. 15 is a simplified schematic side view sectional view of surgical file distal tip with a top cutting surface illustrating features and advantages in accordance with an embodiment of the invention.

FIG. 15 shows a lengthwise-section of the distal tip portion 92 having a cutting surface 114c on the top or upper side of the reciprocating blade 106 within the non-moving shield 108. This configuration is suited for some particular bone and/or tissue removal applications. The bend 116 allows the cutting surface 114c to pass into a cavity that involves traveling around a corner. The direction of blade travel is generally denoted by arrows 204.

Figure 16:
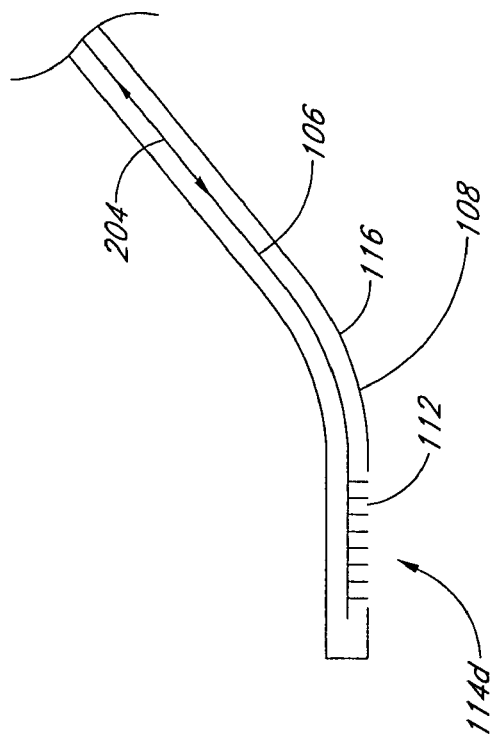
FIG. 16 is a simplified schematic side sectional view of a surgical file distal tip with a top cutting surface illustrating features and advantages in accordance with another embodiment of the invention.

FIG. 16 shows a lengthwise-section of the distal tip portion 92 having a cutting surface 114d on the bottom or lower side of the reciprocating blade 106 within the non-moving shield 108. This configuration is suited for some particular bone and/or tissue removal applications. The bend 116 allows the cutting surface 114d to pass into a cavity that involves traveling around a corner. The direction of blade travel is generally denoted by arrows 204.

Figure 17:
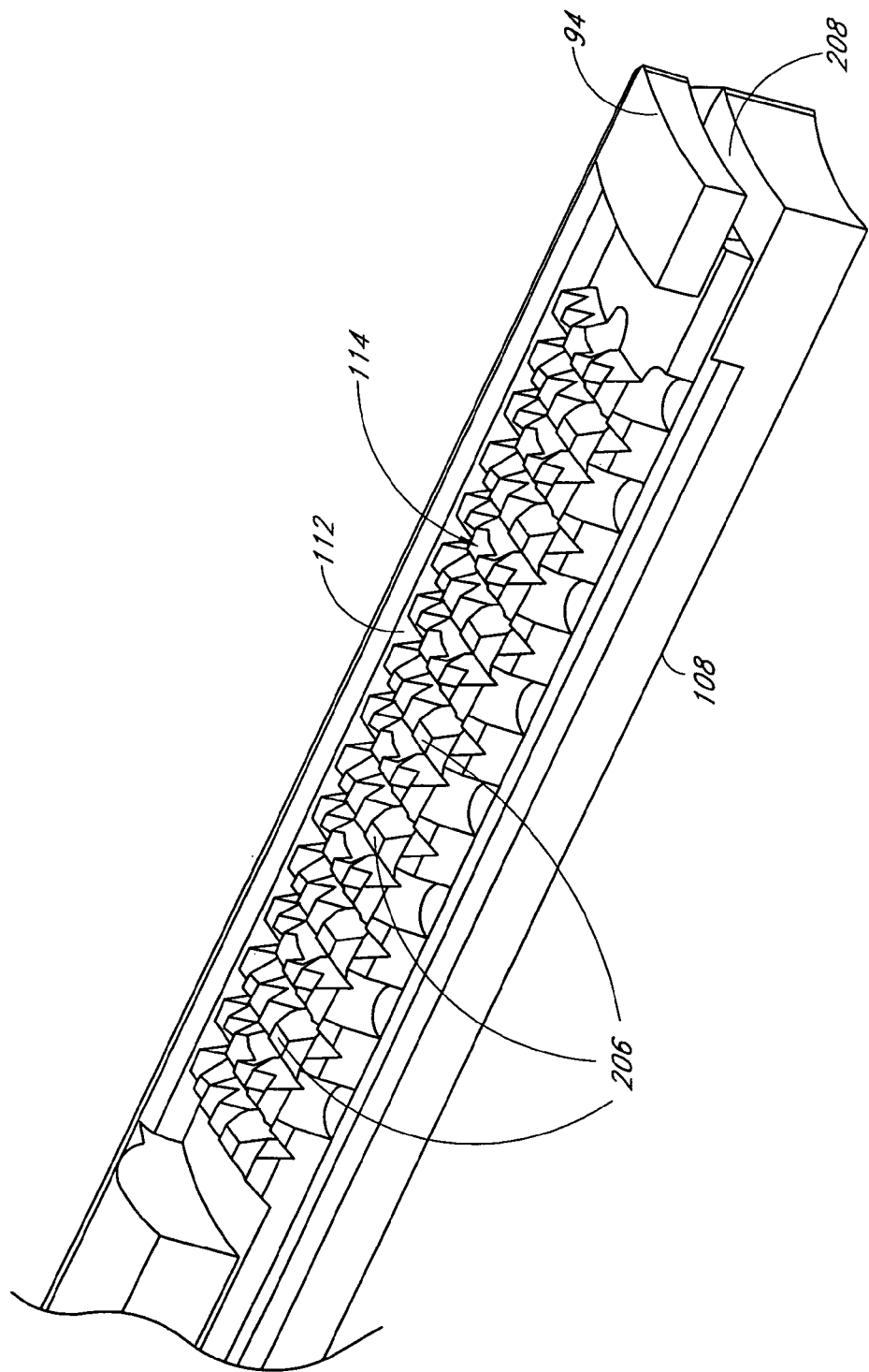
FIG. 17 is a simplified perspective view of a surgical file cutting surface with abrasives illustrating features and advantages in accordance with an embodiment of the invention.

FIG. 17 shows the cutting surface 114 including an abrasive material or abrasives 206 for cutting, removing, filing or grinding bone and/or tissue materials. For clarity, one side of the shield 108 has been removed in the drawing. Any one of a number of suitable abrasives may be used that are safe to use within a patient's body or are biocompatible and hard. In one embodiment, the abrasives 206 comprise embedded diamonds or diamond particles.

Also shown in FIG. 17 is a lateral slot or opening at the tip portion distal end 94. Advantageously, the distal opening 208 allows the removal of any bone and/or tissue debris that may collect within the distal and provides for flushing out of the debris as the blade cutting surface 114 reciprocates and the irrigation fluid flows out of the instrument.

Figure 18:
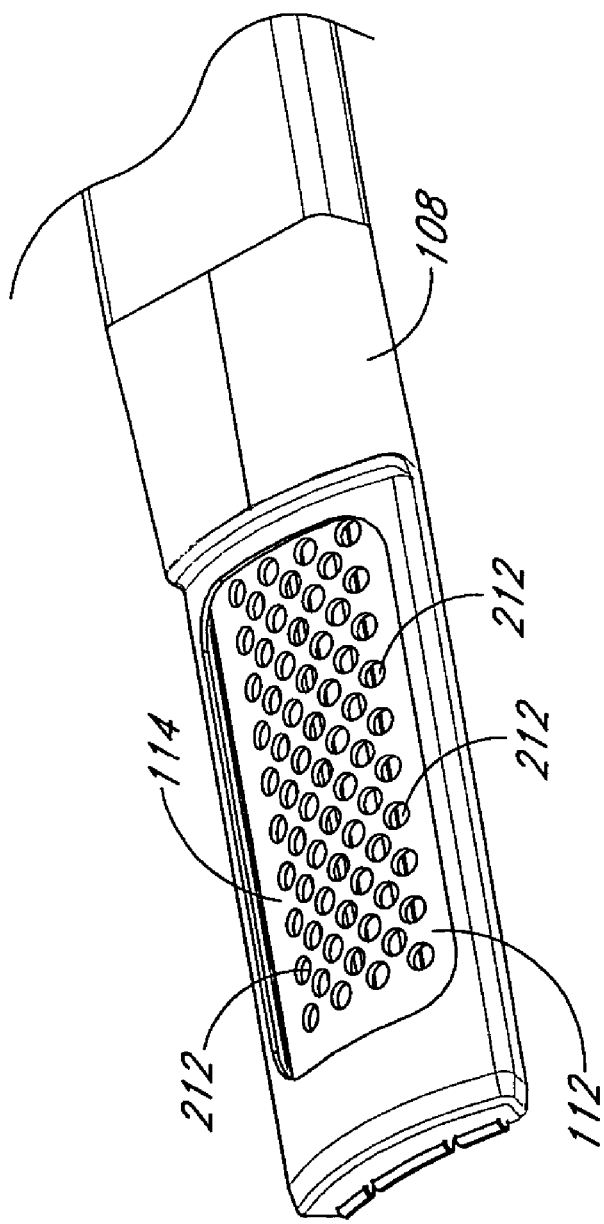
FIG. 18 is a simplified perspective view of a surgical file cutting surface with irrigation fluid openings illustrating features and advantages in accordance with an embodiment of the invention.

FIG. 18 shows the blade cutting surface 114 including a plurality of micro holes or openings 212 for the flow of irrigation fluid therethrough. For clarity the abrasives are not shown in the drawing. The holes 212 are in fluid, liquid or hydraulic communication with the longitudinal slots 190 of the lower linear bearing 120. The slots 190 of the upper linear bearing 120 also provide irrigation water to the cutting area.

Figure 19:
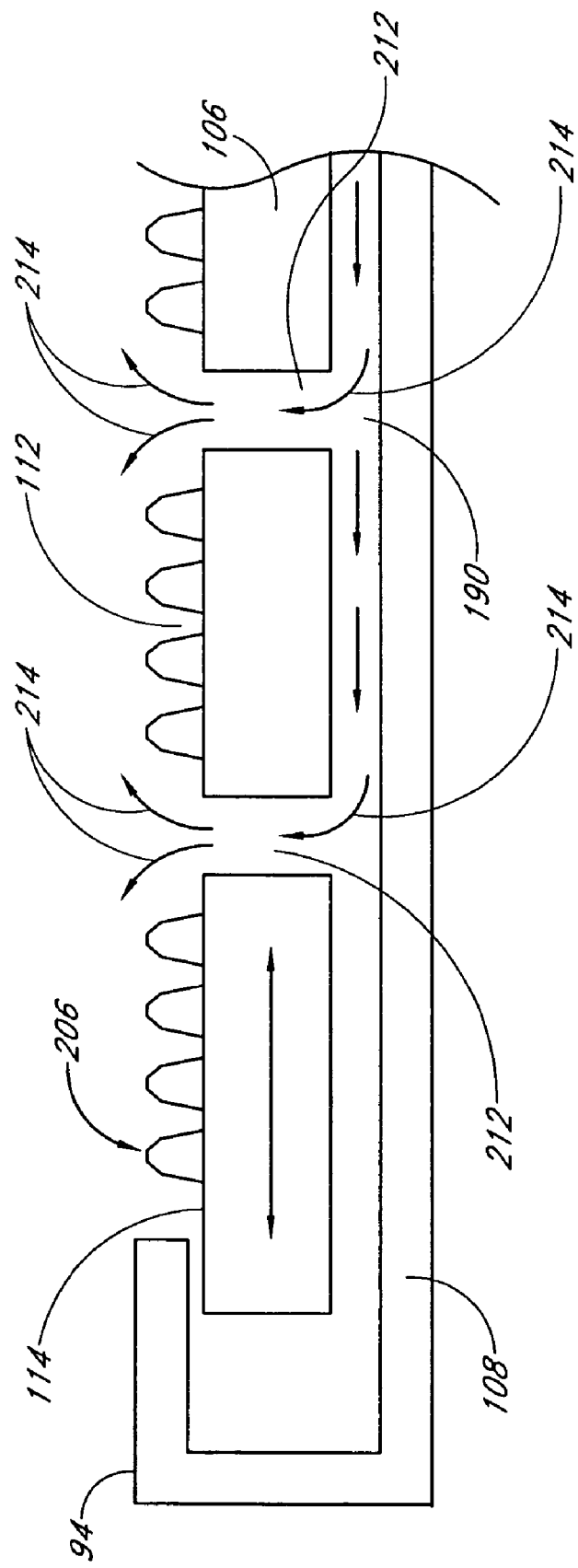
FIG. 19 is a simplified schematic view of a surgical file cutting blade with irrigation fluid flow therethrough illustrating features and advantages in accordance with an embodiment of the invention.

FIG. 19 schematically depicts the fluid, liquid or hydraulic communication between the bearing slot(s) 190 and the cutting surface holes 212. The flow of water from the bearing slots(s) 190 and the micro hole openings 212 is generally indicated by arrows 214. The water is forced to flow up, down or out through the openings 212 in the cutting blade surface 114 and away from the blade cutting surface 114. The water washes away cut material and keeps debris from clogging the cutting surface 114 to maintain optimum cutting and material removal performance, and to keep the cutting area cool to prevent tissue necrosis damage.

The water also flows over the moving (reciprocating) cutting blade 106 and drive mechanism or bearings 120 to provide cooling and lubrication. The water can be forced into the cutting cavity 112 to flush away micro cutting debris and maintain a clear field of view for video navigation and visualization. The water can be forced into the cutting area cavity 112 to clean and remove freshly cut bone cells and bone fragments to prevent repopulation and unwanted bone growth in the area.

Figure 20:
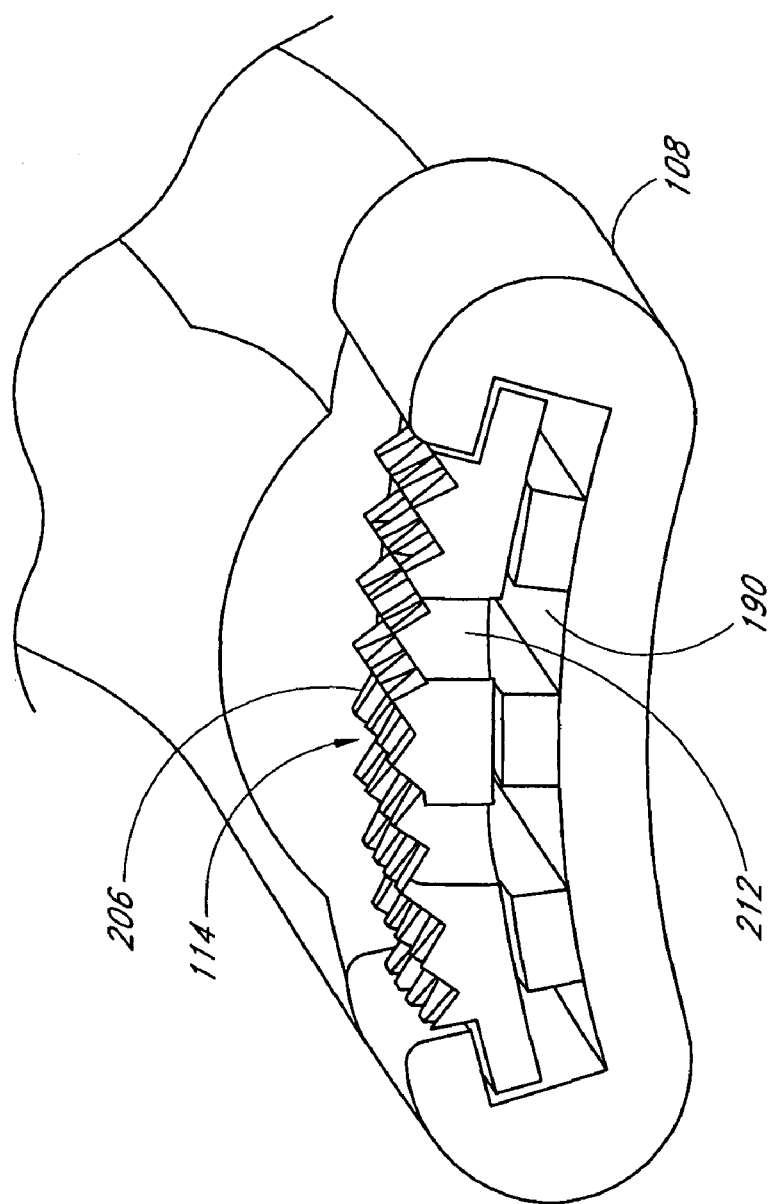
FIG. 20 is a simplified schematic cross-section view of a surgical file distal cutting tip with irrigation fluid passageways illustrating features and advantages in accordance with an embodiment of the invention.

FIG. 20 is another schematic depiction showing the fluid, liquid or hydraulic communication between the irrigation fluid holes 212 and the bearing irrigation passageways 190. The drawing also shows the abrasive material or abrasives 206 of the blade cutting surface 114.

Figure 21:
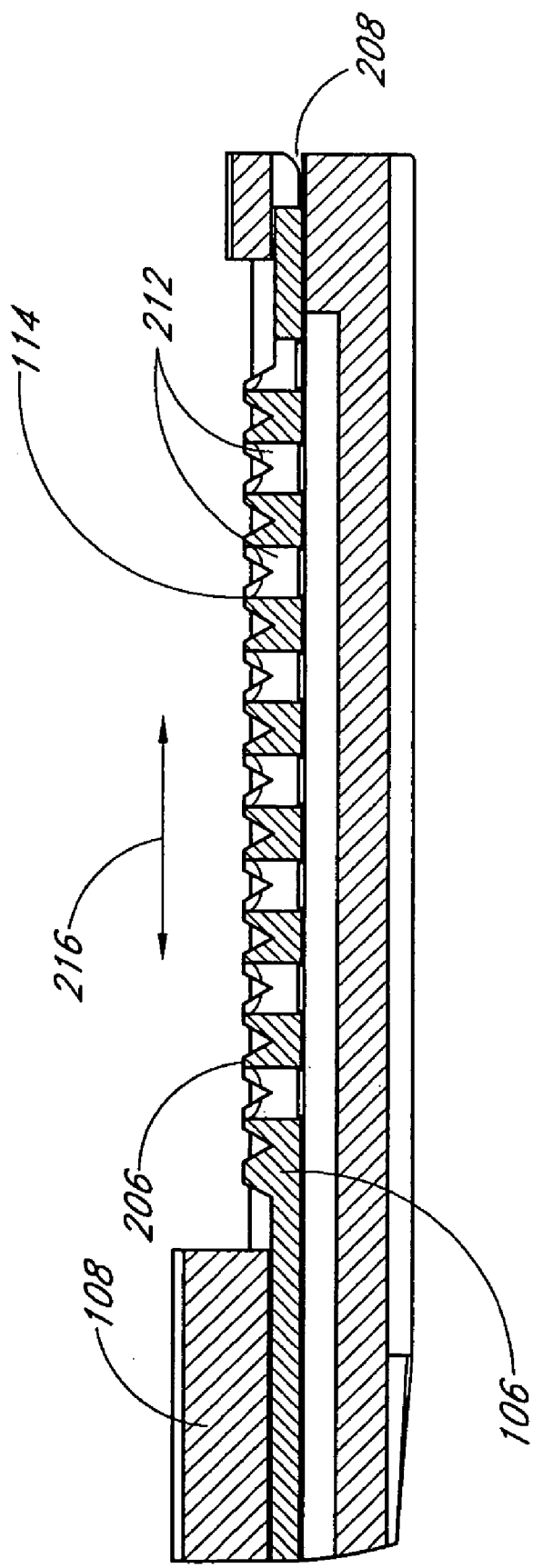
FIG. 21 is a simplified side sectional view of a surgical file distal cutting tip with a linear reciprocation stroke illustrating features and advantages in accordance with an embodiment of the invention.

FIG. 21 shows the reciprocation blade stroke direction as generally indicated by arrows 216. The free linear motion of the reciprocation blade stroke is a linear stroke. In one embodiment, for applications within the human body, the linear stroke is in the range from about 2.5 mm (0.1 inches) to about 7.6 mm (0.3 inches), including all values and subranges therebetween. In another embodiment, the linear stroke is in the range from about 1.3 mm (0.05 inches) to about 12.7 mm (0.5 inches), including all values and subranges therebetween. In yet another embodiment, the linear stroke is in the range from about 0.25 mm (0.01 inches) to about 25.4 mm (1 inch), including all values and sub-ranges therebetween. In modified embodiments, the linear stroke may efficaciously be lower or higher depending on the particular application, as needed or desired.

Cauterization

In accordance with one embodiment, the surgical file instrument 12 can stop the small amount of bleeding of freshly cut or sculpture shaped bone or other tissue by accommodating connection to existing cauterizing equipment 60. In this embodiment, the special feature the system has is a non-electrically conductive shield 108, which is covering an electrically conductive metal file blade 106.

When bleeding of the freshly cut bone is detected, the file cutting blade 106 can be brought back into contact with the freshly shaped bone that may be bleeding slightly. A pulse of electricity can be momentarily applied that will flow from the metal blade file surface into the bleeding bone or other tissue surfaces. This will heat the bleeding bone or other tissue surfaces, coagulate the blood flow and advantageously stop the bleeding of the bone and/or tissue surface. Desirably, the irrigation flow facilitates localizing the heat and cooling while the shield 108 protects the adjacent nerves and spine from heat.

Illumination and Vision Probes

Figure 22:
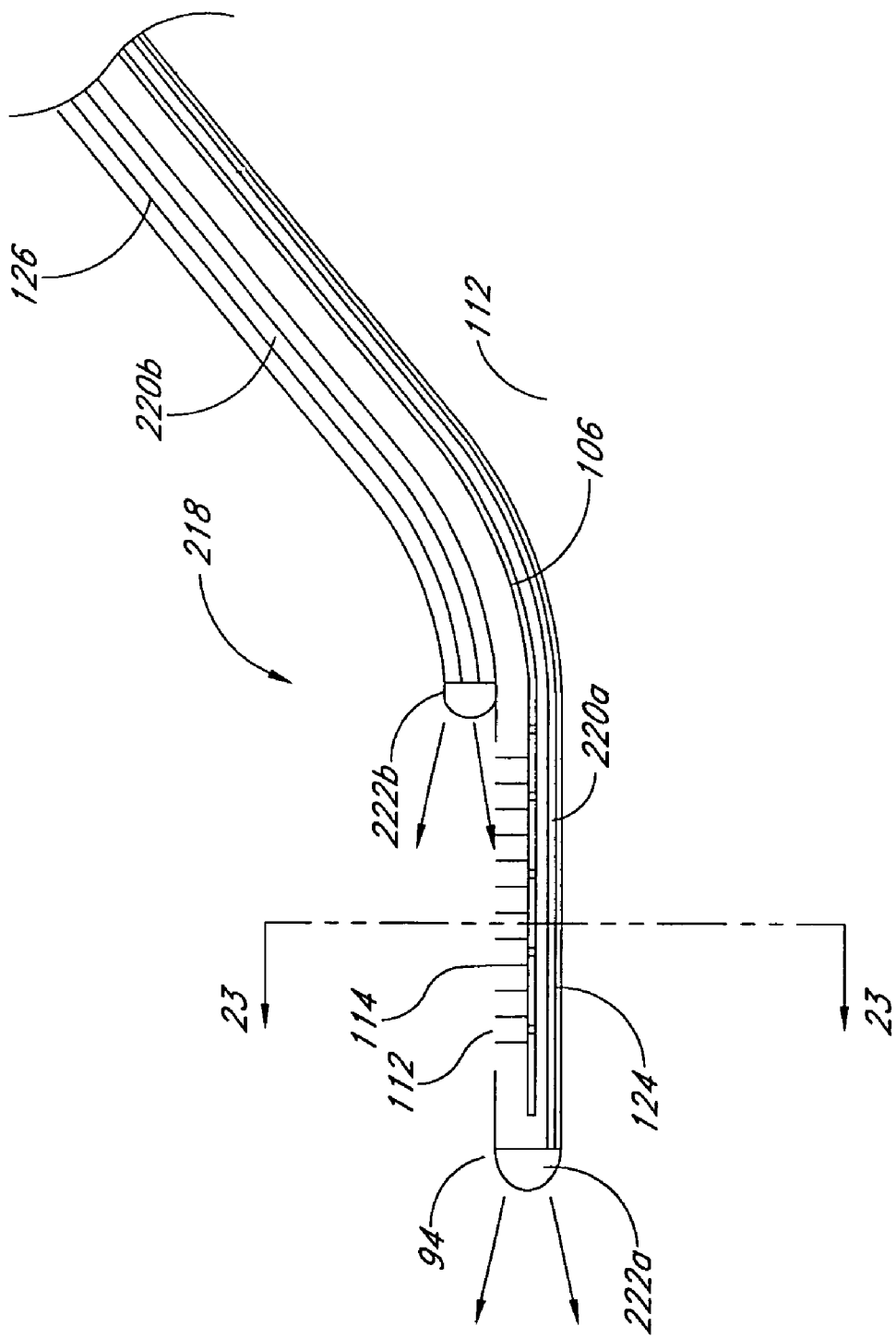
FIG. 22 is a simplified side sectional view of a surgical file distal cutting tip with fiber optic probes illustrating features and advantages in accordance with an embodiment of the invention.

FIG. 22 shows a fiber optic vision system 218 including the fiber optic probes 124 and 126. The fiber optic vision system 218, in some surgical embodiments, enables surgeons to visually see and verify the presence of unwanted bone and cartilage buildup that is causing nerve root compression and damage to normal body functions. This information on the unwanted material can be documented and recorded by saving visual pictures into a computer database and printing color pictures immediately for reference and record.

The lower fiber optic probe 124 includes a plurality of optical fibers 220a that optically terminates at a distal lens array or arrangement 222a. The lens array 222a is positioned at substantially the tip distal end 94. The fiber optic probe 124 may be placed within the shield 108 or it may have a separate housing. The lower fiber optic probe 124 generally follows the longitudinal profile of the distal tip portion 92, the blade 106 and/or the shield 108.

The upper fiber optic probe 126 includes a plurality of optical fibers 220b that optically terminates at a distal lens array or arrangement 222b. The lens array 222b is positioned proximal to the blade cutting surface 114. The fiber optic probe 126 may be placed within the shield 108 or it may have a separate housing. The upper fiber optic probe 126 generally follows the longitudinal profile of the distal tip portion 92, the blade 106 and/or the shield 108.

Advantageously, the fiber optic vision system 218 enables visual viewing of the patients body cavities all during insertion and placement of the cutting blade. This is intended to enable the surgeon to safely navigate the tiny body cavities such as neuroforamen tubular canal and avoid damage to fragile nerve roots.

Figure 23:
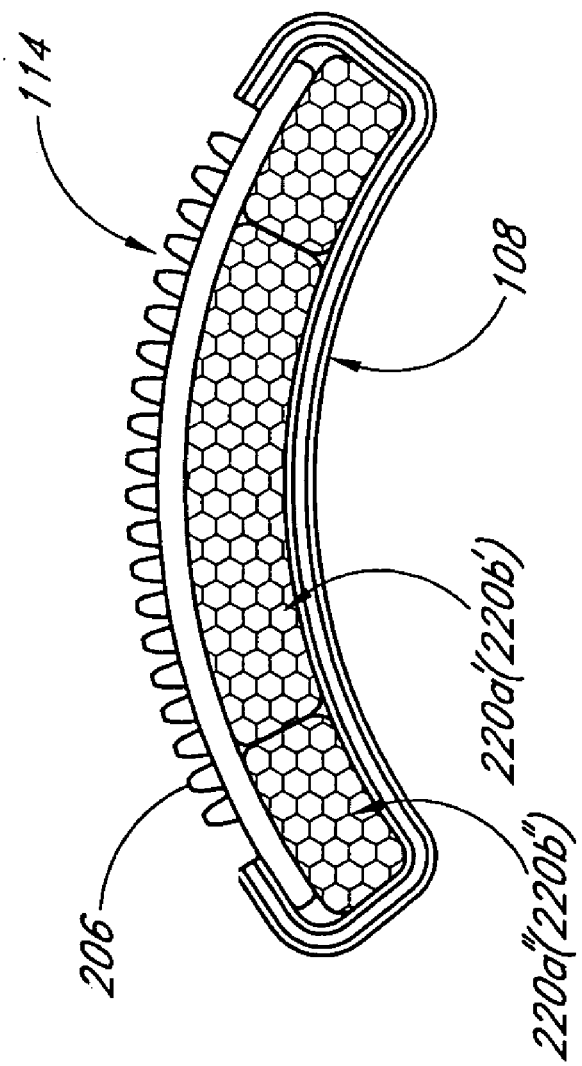
FIG. 23 is a simplified sectional view along fine 23-23 of FIG. 22 illustrating features and advantages in accordance with an embodiment of the invention.

FIG. 23 shows the optical fibers 220a in more detail. The upper optical fibers 220b (220b', 220b") have a similar configuration and functioning though they may have a different curvature or be flat and planar. The optical fibers 220a comprise a central plurality of optical vision fibers 220a' flanked by light or illumination fibers 220a". The optical vision fibers 220a' are connected at their proximal end to the video camera 78.

The fiber optical illumination fibers 220a" illuminate the body cavity and enable video visualization. An LED located at the proximal end of the fiber optics illumination fibers 220a" is used transmit light to the distal end of the illumination fibers 220a" to provide illuminating light. Advantageously, the direct vision optical system 218 enables surgeons to safely navigate into blind cavities of the human body and to illuminate and see specific body anatomy such as nerves and bony buildups that could be irritating and pressing against nerves causing nerve compression.

In the illustrated embodiment, the direct vision optical system 218 desirably provides an integrated illumination and optical vision system. The optics for vision and illumination are included within the distal tip assembly 18 which in some embodiments is a docking sterile one time use assembly.

Figure 24:
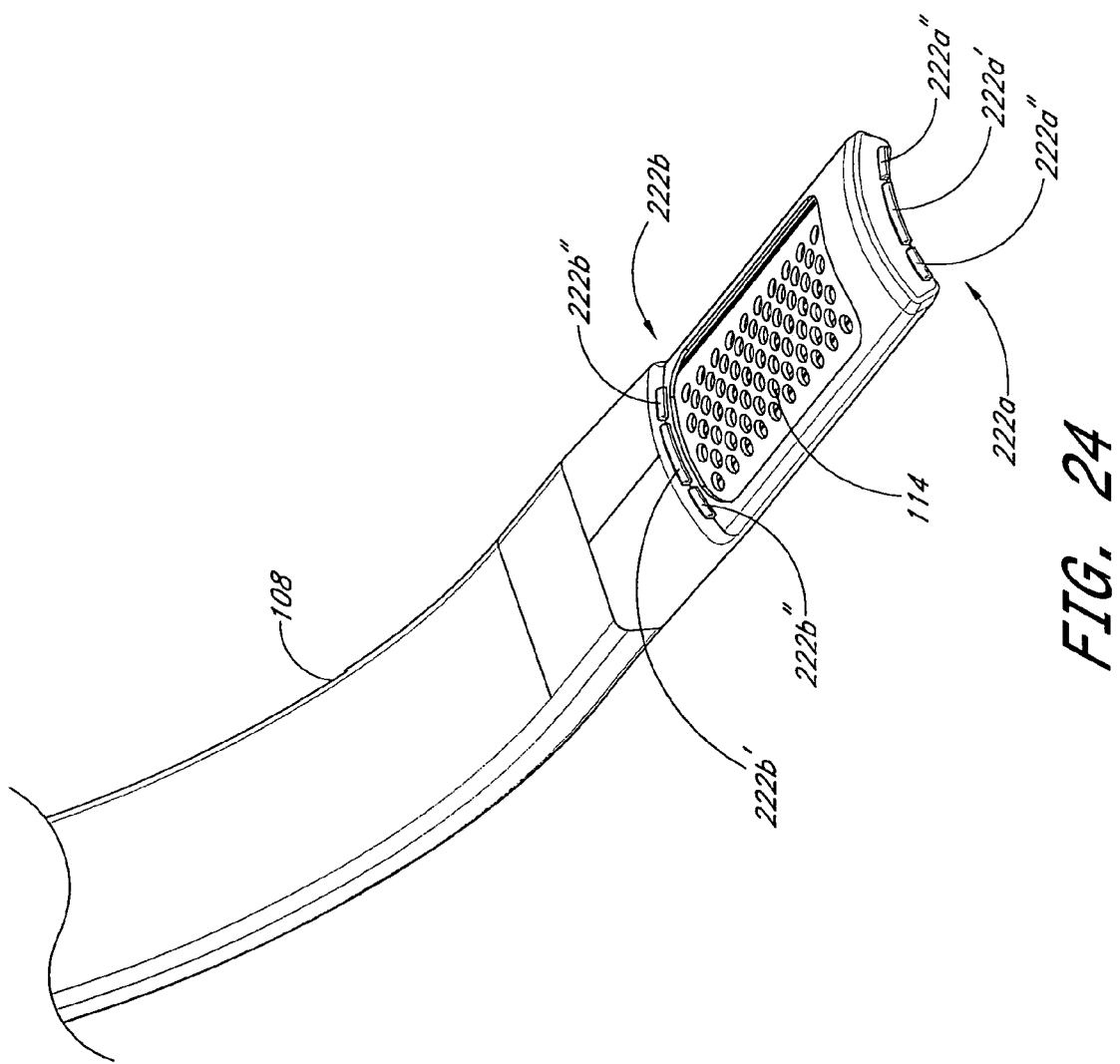
FIG. 24 is a simplified side sectional view of a surgical file distal cutting tip with an illumination and vision system illustrating features and advantages in accordance with an embodiment of the invention.

Referring in particular to FIG. 24, the distal optical system lenses arrangements 222a and 222b are each arrayed in three segments. The lower optical segments 222a are arranged with a video imaging lens 222a' centered medially and with illuminating lenses 222a" positioned on the right and left lateral sides. The upper optical segments 222b are arranged with a video imaging lens 222b' centered medially and with illuminating lenses 222b" positioned on the right and left lateral sides.

Figure 25:
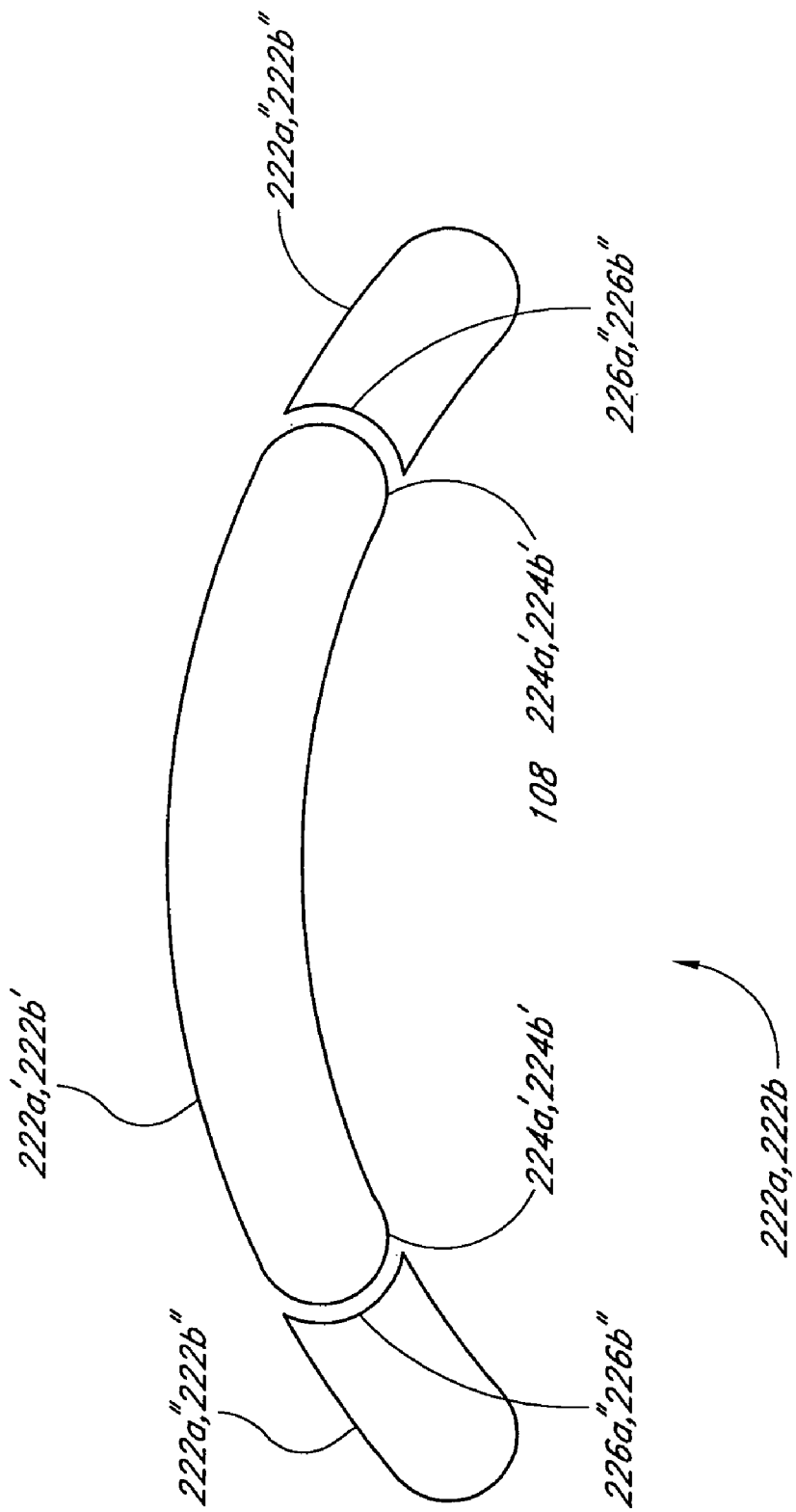
FIG. 25 is a simplified schematic view of an arrangement of lenses of a surgical file illumination and vision system illustrating features and advantages in accordance with an embodiment of the invention.

FIG. 25 shows the lens arrays 222a, 222b in more detail. The lateral sides of the central lenses 222a', 222b' have a respective semi-arc male shape 224a', 224b' to each of their left and right sides. The illuminating lenses 222a", 222b" are shaped to have mating female semi-arc medial sides 226a", 226b" on there medial sides which mate into the male mating features 224a', 224b' of the central lens sides.

Advantageously, such mating lens arrays 222a, 222b can accommodate a wide range of instrument sizes while using substantially the same basic lens assembly design. Different lenses may be used in the design and the curvature of the lens array adjusted and changed to provide the desired illumination and/or field of view. For example, for a particular medial video imaging lens 222a', 222b' the curvature of the side illuminating lenses 222a", 222b" can be adjusted or changed to illuminate the desired field of view. This desirably saves on cost since micro lenses are very expensive to tool up and make. The distal tip assembly 18 can have numerous sizes with varying cross sections of the distal tip portion 92 depending on the particular application and advantageously substantially the same basic lens assembly design 222a, 222b can be utilized with the different sizes.

Additionally the mating lenses 222a', 222b' and 222a", 222b" allow the black out of the respective mating surfaces 224a', 224b' and 226a" and 226b" to substantially prevent illumination light from passing laterally into the imaging lens 222a', 222b' and degrading the optical quality of the resulting picture. A lens set comprising the central imaging lens 222a', 222b' and one each right and left illuminating lenses 222a", 222b" can be assembled onto a wide range of instrument disposable cutting tips 18 in an assembly that has an optical distal lens system which is very thin in cross section and that the lenses follow the instrument cross sectional curve. Advantageously, for embodiments of the invention and in particular the neurosurgery embodiments, having a very thin cross section enables the instruments distal tip to fit into the tiny space between a nerve root and its neuroforamen opening.

Figure 26:
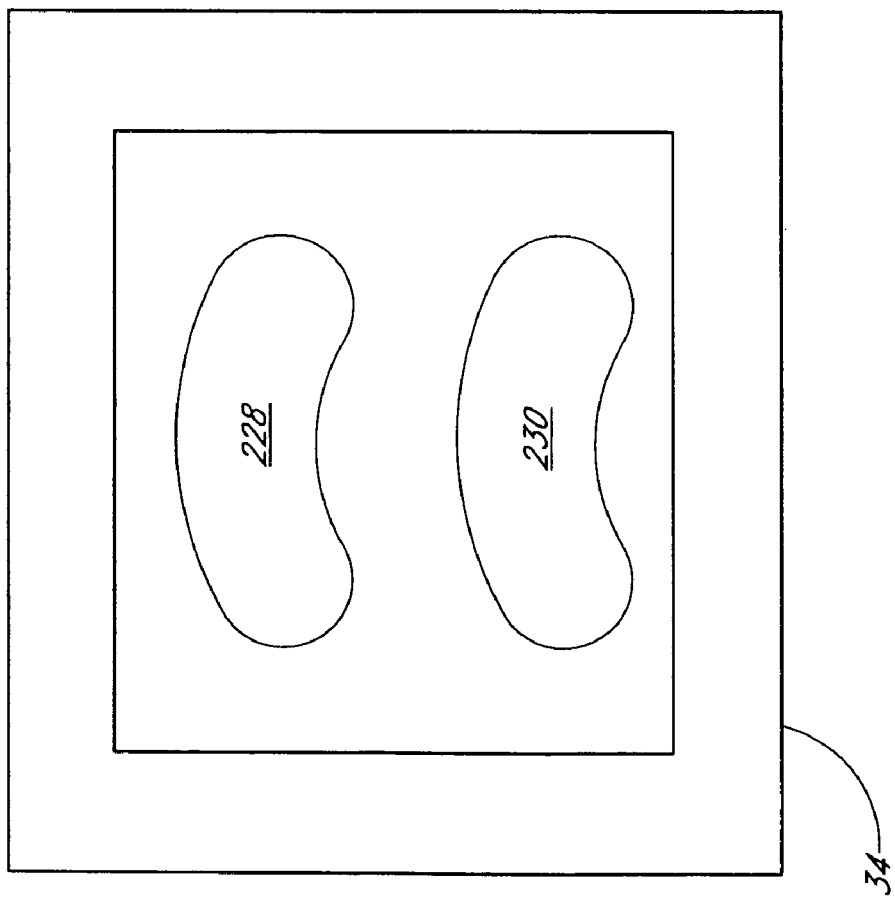
FIG. 26 is a simplified schematic view of display images provided by a surgical file illumination and vision system illustrating features and advantages in accordance with an embodiment of the invention.

As shown in FIG. 26 the images from the direct vision optical system 218 can be viewed on the LCD monitor 34. The drawing shows an example of the display with a view 228 from the upper fiberoptic 126 looking onto the blade 106 and a view 230 from the lower fiberoptic 124 looking out from the instrument distal end 92.

Toroidal Transmission System

The toroidal transmission or power conversion system 98 is a mechanical conversion device that converts rotary to reciprocating motion or action. The powered handpiece 20 houses a rotating motor 80 to power the cutting action of the tissue removal instrument or blade 106. The rotating mechanical action of the motor 80 is converted into reciprocating mechanical motion of a suitable reciprocal stroke length. It is desirable that the mechanical motion conversion device be simple and have few parts.

Having a video camera system mounted directly into a reciprocating motion mechanical device can create a stability problem with respect to inherent vibration that is usually inherent in all reciprocating motion mechanical devices. Advantageously, the toroidal drive system 98 of embodiments of the invention provides a desirable solution for the vibration problem since it has low or minimum levels of associated vibration. This advantageously provides a stable platform for the capture of high quality pictures by the video system including the camera 78 housed in the handpiece 20.

The toroidal drive system 98 inherently has few parts and can be built to be very low vibration due to low mass of the reciprocating components. Thus, the toroidal drive system 98 can provide the powered handpiece 20 with a stable platform and a smooth running mechanical action. The transmission system of embodiments of the invention has utility in a number of fields and applications where conversion of rotary motion to reciprocating motion is desired.

Figure 27:
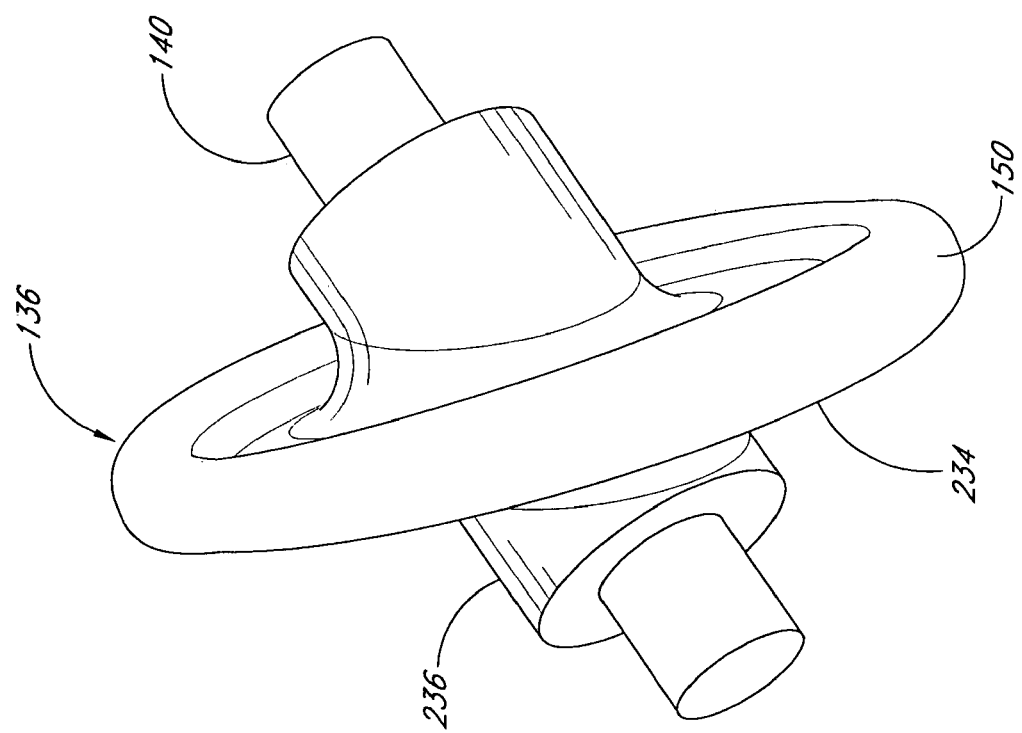
FIG. 27 is a simplified perspective view of a dual torus and drive shaft illustrating features and advantages in accordance with an embodiment of the invention.
Figure 28:
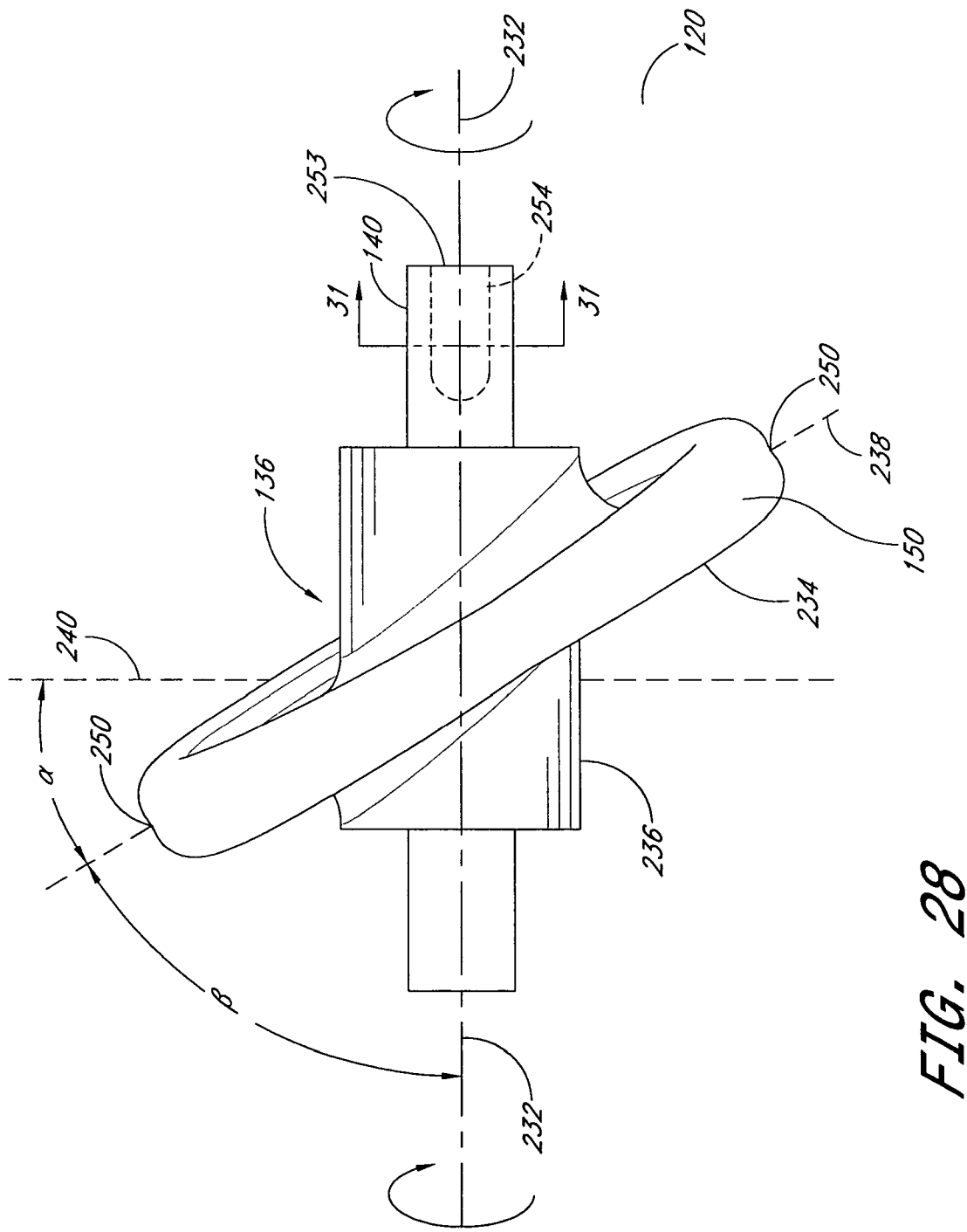
FIG. 28 is a simplified side view of the dual torus and drive shaft of FIG. 27.

FIGS. 27 and 28 show the toroid drive 136 and the female receptor drive shaft 140. In one embodiment, the toroid drive 136 and the drive shaft 140 comprise an integral unit and are formed as a single piece. In another embodiment, the toroid drive 136 and the drive shaft 140 can be rigidly connected to one another.

The toroid drive 136 and the drive shaft 140 can be formed from a number of suitably durable materials. In one embodiment, the toroid drive 136 and the drive shaft 140 are formed from a suitable plastic by molding. The plastic material may comprise a suitable thermoplastic. In modified embodiments, other suitable plastics, metals, alloys, ceramics, combinations thereof, among others, may be efficaciously utilized, as needed or desired. Suitable surface coatings or finishes may be applied, as required or desired.

The toroid drive 136 and the drive shaft 140 can be fabricated by using a number of manufacturing techniques. These include, but are not limited to, molding, machining, casting, forging, laser cutting and/or processing, laminating, adhesively fixing, welding, combinations thereof, among others, with efficacy, as needed or desired.

The toroid drive 136 and the drive shaft 140 are rotatable about a substantially central rotation axis 232. The toroid drive 136 has a generally circular or curvilinear cam portion 234 and a generally central shank portion 236. As discussed further below, the cam 234 has a specially designed generally circular or curvilinear outer rim 150 with a varying or non-uniform thickness.

The cam 234 and/or the outer rim 150 have a substantially central side view plane 238. The cam 234 and/or the outer rim 150 are tilted relative to a vertical plane or axis 240 by a predetermined angle α and hence to the rotation axis by an angle β where β=90°−α. Thus, typically β and α are less than 90°.

In one embodiment, α is about 20° and β is about 70°. In another embodiment, α is in the range from about 10° to about 40° and β is in the range from about 50° to about 80°, including all values and sub-ranges therebetween. In yet another embodiment, α is in the range from about 5° to about 80° and β is in the range from about 10° to about 85°, including all values and sub-ranges therebetween. In modified embodiments, α and β may be lower or higher, as needed or desired.

Figure 29:
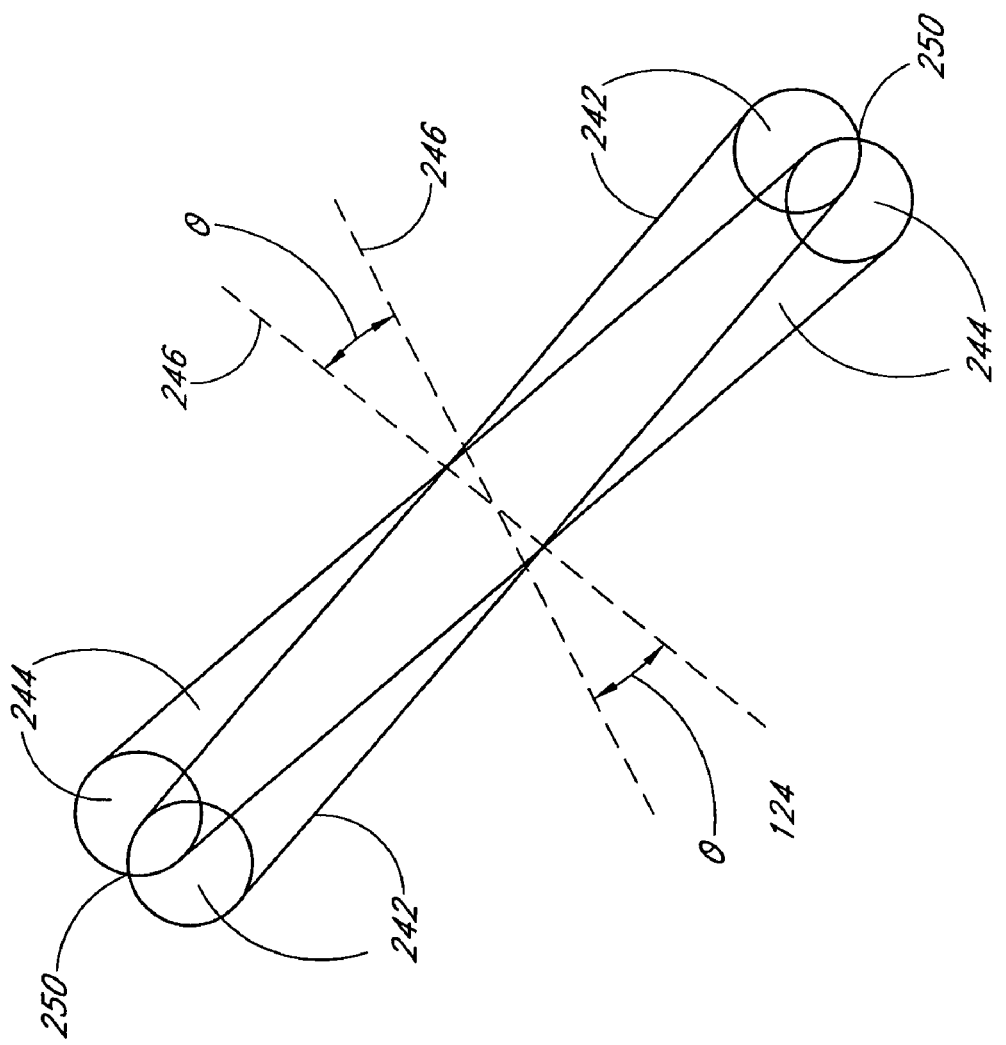
FIG. 29 is a simplified schematic view of a dual torus partial superposition illustrating features and advantages in accordance with an embodiment of the invention.

As schematically illustrated in FIG. 29, in one embodiment, the cam 234 and/or the outer rim 150 are designed to provide a variable thickness for the outer rim 150 by the partial superimposition of two toruses or toroids 242, 244 of substantially uniform rim thickness with respective central axes 246, 248. By controlling the degree of superposition, the rim 150 of variable and controlled thickness is created. Thus, the transmission or power conversion system 98 is also referred to as a "hybrid dual or twin toroid" system.

Advantageously, the outer rim 150 thickness is varied such that the rim 150 substantially continuously contacts the bearing surfaces 164 and 166 as the cam 234 rotates about the central axis 232. Thus, desirably the two surfaces 164 and 166 can remain at a substantially fixed distance apart as they move linearly back and forth in reciprocating motion in response to the cam's rotation about the central axis 232.

In the illustrated embodiment, the torus central axes 246, 248 are at an offset angle θ to produce the desired variable thickness rim 150. The slightly dimpled or grooved surface 250 is indicative of the partial superposition of the two toruses or toroids 242, 244. In modified embodiments, more than two toruses and/or toruses with variable rim thickness may be utilized to create the desired outer rim profile.

Advantageously, the dual torus or toroid (one toroid partially inside another) configuration provides an elegant solution of for maintaining a uniform distance between the bearing surfaces 164, 166 or driven rollers. The rotation of the toroid or torus cam 234 moves the outer rim 150 in a reciprocating motion with the motion being generally parallel to the rotary axis 232. The reciprocating motion of the slide plate 138 is also generally parallel to the rotary axis 232 which is then transmitted to the blade 106.

Figure 30:
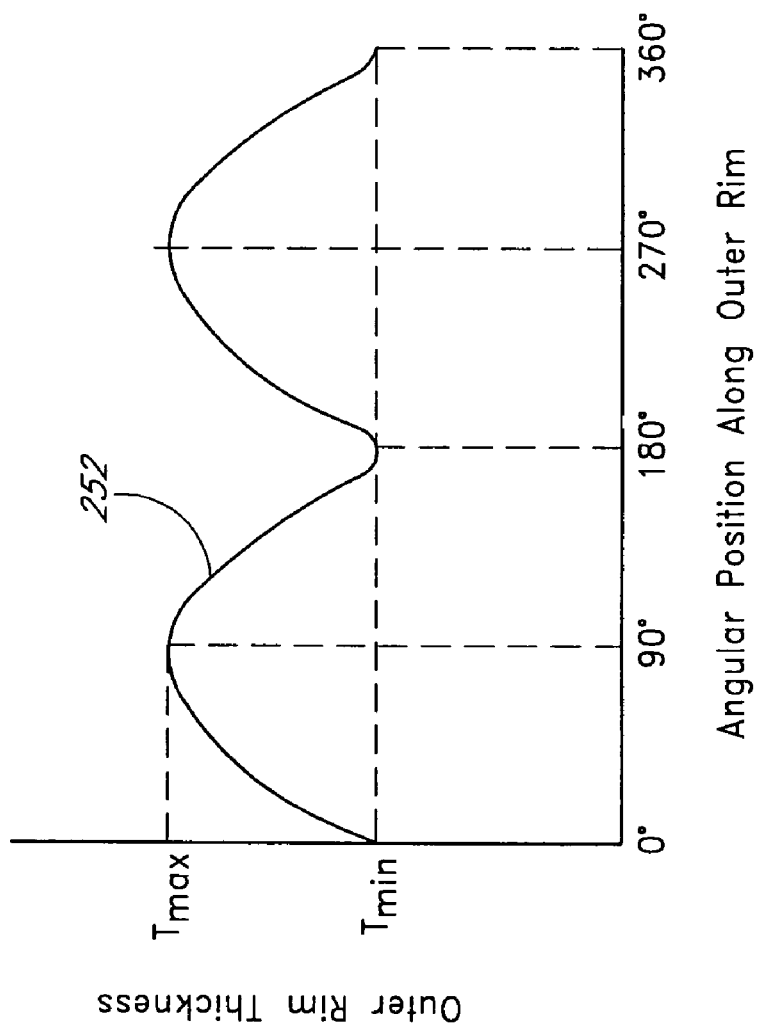
FIG. 30 is a simplified schematic graphical representation of variation in outer rim thickness of a dual torus or toroid illustrating features and advantages in accordance with an embodiment of the invention.

FIG. 30 shows the thickness profile of the outer rim 150 in accordance with one embodiment. The thickness varies across the rim 150 in a generally offset sinusoidal profile with a minimum thickness $T_{min}$ and a maximum thickness $T_{max}$. In modified embodiments, other suitable rim thickness profiles may be efficaciously utilized, as needed or desired.

The disposable cutting blade assembly 18 includes the integrated transmission system 98 within the distal cover 72. The transmission system 98 converts the rotary motion of the drive motor 80 into the reciprocating motion of the tissue-cutting blade 106. The transmission system 98 is a sterile assembly of the disposable cutting blade assembly 18 that is sterile packaged.

The transmission system 98 is an internal mechanism and is generally housed within the housing 96. This is important in that the "one time use disposable" tip assembly 18 embodiments because easy separation from the re-sterilizable motor drive portion of the powered handpiece 20. In theses embodiments, the powered handpiece 20 with its rotary motor 80 comprises an independent assembly from the disposable distal cutting tip assembly 18. Numerous sizes and shapes of distal cutting tip portion 92 are available to be connected onto the motor drive powered handpiece 20.

Since the disposable distal cutting tip assembly 18 has an internal mechanism to convert rotary motion into reciprocating motion, it advantageously enables a simple and cost effective means of disconnecting the two assemblies 18 and 20. The drive shaft 140 at its proximal end 253 includes a female receptor hole 254 that is configured to substantially irrotationally mate with a matching male distal shaft drive protruding out of the motor drive 80.

Figure 31A:
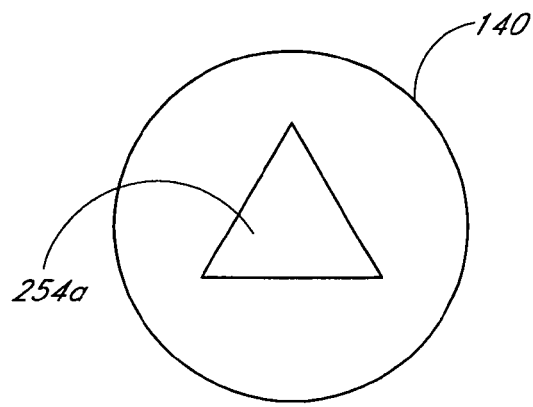
FIG. 31A is a simplified sectional view along line 31-31 of FIG. 28 illustrating features and advantages in accordance with an embodiment of the invention.

FIG. 31A shows a simple female triangular hole 254a in the drive shaft 140 that can engage a triangular shaped distal shaft drive protruding out of the motor drive assembly. When the distal tip assembly 18 and the powered handpiece 20 are connected both the female triangular receptor hole 254a and the motor's male triangular drive shaft can rotate in tandem. The male and female features are free to mesh and align during the axial motion of connecting the disposable cutting tip assembly 18 onto the reusable sterilizable motor handpiece 20.

A triangular shaped male mating drive is desirable because it facilitates sterilization of the male triangular shaft. The surfaces that are steam sterilized and reused are desirably simple surfaces that are easy to wash and clean. The surfaces should also enable reliable cleaning prior to sterilization. A triangular male shaft has three flat surfaces that are both easy to see and clean.

Figure 31B:
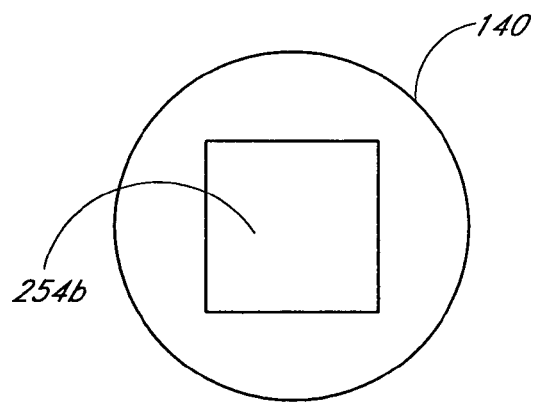
FIG. 31B is a simplified sectional view along line 31-31 of FIG. 28 illustrating features and advantages in accordance with another embodiment of the invention.
Figure 31C:
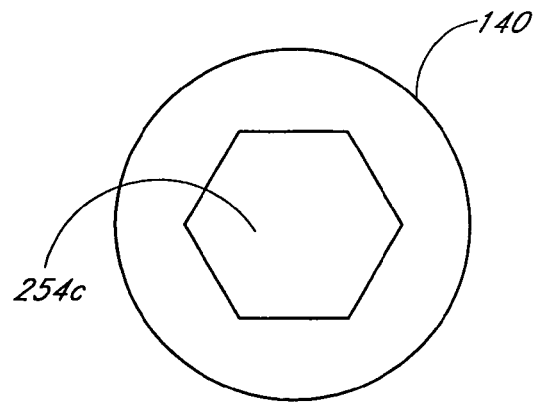
FIG. 31C is a simplified sectional view along line 31-31 of FIG. 28 illustrating features and advantages in accordance with yet another embodiment of the invention.

In modified embodiments, other suitable male-female mating drive polygonal or non-polygonal interlocking configurations may be utilized with efficacy, as needed or desired. For example, FIG. 31B shows a generally square or rectangular female receptor hole 254b and FIG. 31C shows a generally hexagonal female receptor hole 254c.

Figure 32:
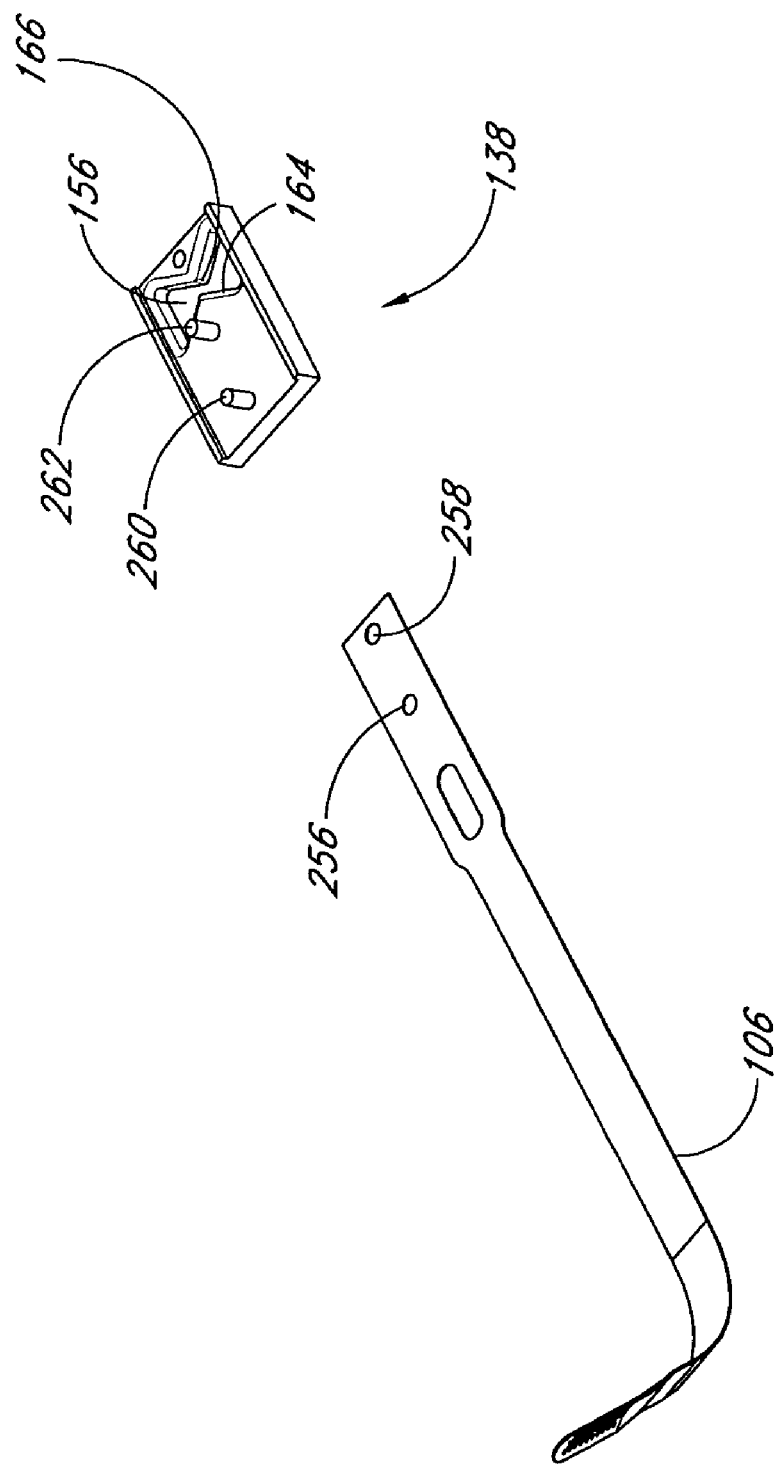
FIG. 32 is a simplified perspective view of a distal cutting blade and a reciprocating slide plate that connects to the blade illustrating features and advantages in accordance with an embodiment of the invention.
Figure 33:
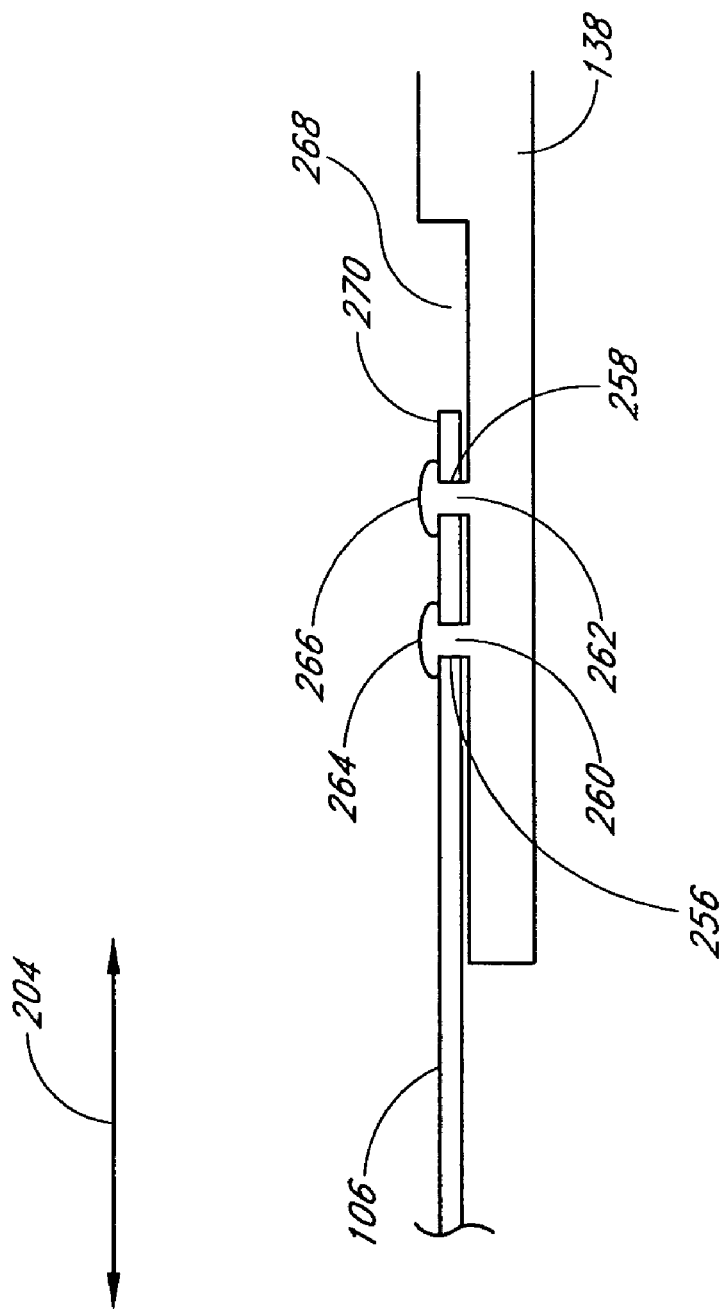
FIG. 33 is a simplified schematic side view of a distal cutting blade connected to a slide blade illustrating features and advantages in accordance with an embodiment of the invention.

FIGS. 32 and 33 show the cutting blade 106 and the drive slide 138. The outer rim 150 of the toroid drive 136 engages the slide slot 156 and abuts against the bearing surfaces 164, 166 as it rotates to reciprocatingly displace the slide 138 connected to the blade 106. The slide 138 can be generally above the toroid drive 136 or it can be generally below the toroid drive 136. In modified embodiments, the slide 138 can be to the sides of the toroid drive 136 as long as the outer rim 150 rotates within the slide slot 156 and causes the slide to move in a reciprocating motion.

It is important that the distal filing blade 106 maintain its structural rigidity and not to fail in a buckling mode that would cause the file blade 106 to become bent or distorted into a shape that may result in an undesirable thicker profile. To safeguard against this, in one embodiment, a safety shear system is provided.

The slide 138 includes a pair of posts or pins 260, 262 that engage respective blade holes 256, 258. In one embodiment, the posts 260, 262 are formed from a molding process in which the slide 138 including the posts 260, 262 comprises a plastic. The posts 260, 262 in one embodiment are heat staked and the like to mushroom and form respective heads 264, 266 to affix the blade 106 and the slide 138. The mushroomed pins 260, 262 prevent undesirable blade buckling by being configured to shear at a force much lower than the force that could potentially buckle the file blade 106.

Thus, advantageously, the file blade 106 is driven by a structure that has an intentional weak point that will shear away the driving reciprocating action of the blade drive 106 to prevent a potential distal blade 106 buckling. The configuration of the shear pins 260, 262 is tailored to the specific file blade configuration (which varies in width and length and cross sectional curve). Thus, the shear pin connection including the diameter and/or cross-section of the mushroomed heads 264, 266 and/or the shank portions of the pins 260, 262 is configured such that the mushroomed pins 260, 262 shear at a force lower than a force that would buckle the specific distal cutting blade 106 and allow safe disengagement and disconnection of the blade 106 from the slide 138.

Advantageously, the diameter(s) of the pins 260, 262 provides a desirable shear pin safety mechanism. The pins 260, 262 allow the connection between the drive slide 138 and the blade 106 to shear at a predetermined force. This force can be determined for a particular cutting blade configuration by a number of methods including modeling, numerical analysis, computer simulation, experimental and empirical testing and the like, among others. Accordingly, each differing cutting blade 106 is provided with a shear connection feature to shear and stop the blade driving action before the blade could conceivably buckle. A clearance space 268 in the slide 138 is provided in the proximal direction behind a blade proximal end 270 to allow the blade 106 to move proximally in the slide part 138 when shear disconnection occurs so that the blade 106 is substantially decoupled from the reciprocating motion.

The safety shear force $F_{shear}$ can be calculated as a function of the blade buckling force $F_{buckle}$ in a number of ways to provide suitable protection. In one embodiment, the shear force $F_{shear}$ is about $\frac{1}{3}^{rd}$ of the blade buckle force $F_{buckle}$. In another embodiment, the shear force $F_{shear}$ is in the range from about $0.25F_{buckle}$ to about $0.75F_{buckle}$, including all values and sub-ranges therebetween. In yet another embodiment, the shear force $F_{shear}$ is in the range from about $0.1F_{buckle}$ to about $0.9F_{buckle}$, including all values and sub-ranges therebetween. In modified embodiments, the shear force $F_{shear}$ may be lower or higher, as needed or desired.

FIGS. 32 and 33 illustrate a connection between the blade 106 and the slide plate 138 in accordance with an embodiment that provides a safety shear decoupling between the 106 and the slide plate 138. In modified embodiments, as the skilled artisan will appreciate, the blade 106 and the slide 138 may be connected utilizing other suitable techniques, as needed or desired.

Figure 34:
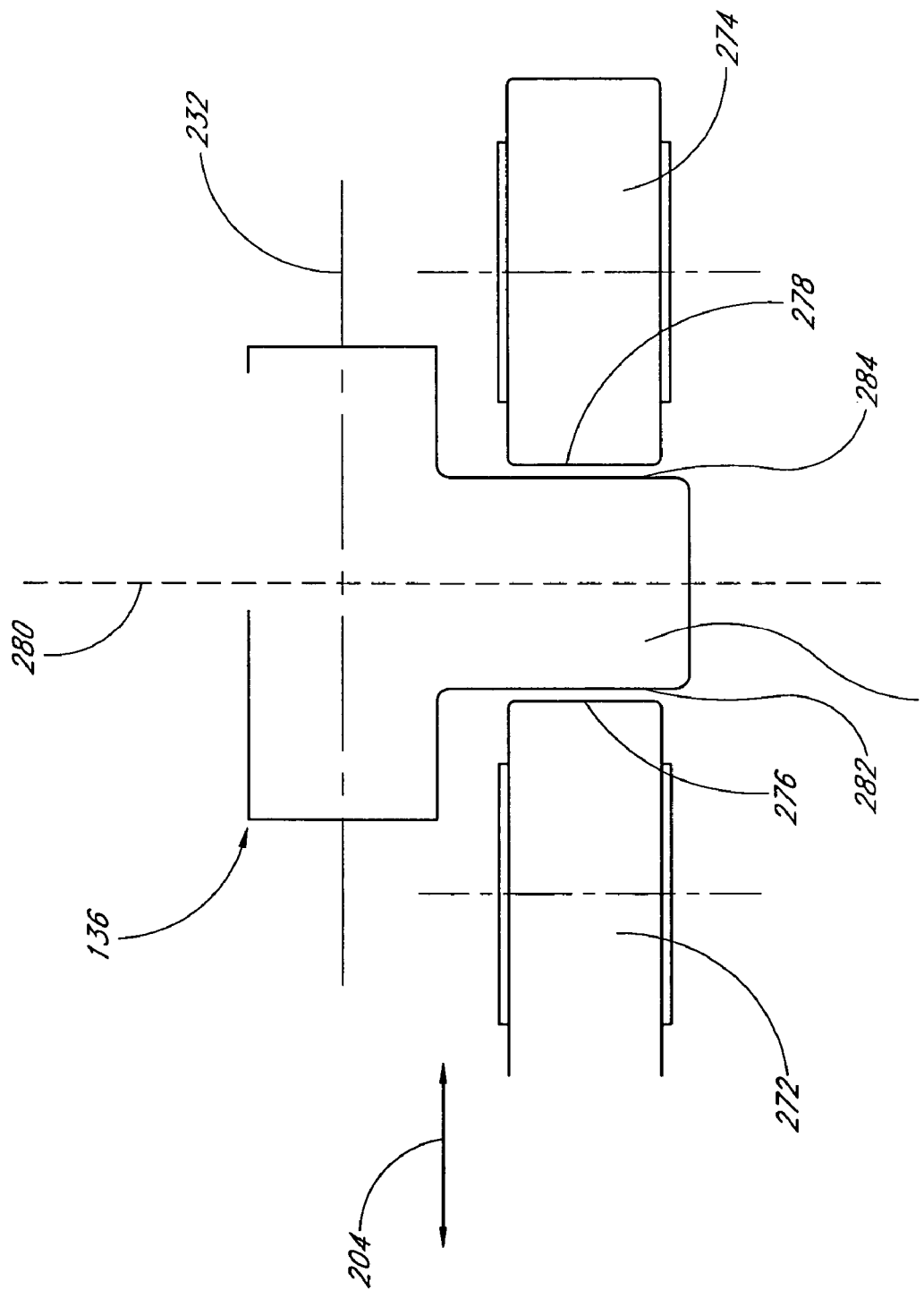
FIG. 34 is a simplified schematic view of toroid drive and associated bearings illustrating features and advantages in accordance with an embodiment of the invention.

FIG. 34 shows the hybrid dual toroid drive 136 with a pair of associated bearings 272, 274 operatively mounted on the slide plate 138. The bearings 272, 274 and their toroid abutting surfaces 276, 278 are spaced by a predetermined distance that allows the variable thickness cam outer rim 150 to be in substantially continuous contact while rotating. In this embodiment, the rotation axis 232 is substantially perpendicular to a plane 280 between the bearing surfaces 276, 278.

The specially configured bearing abutting surfaces 282, 284 of the outer rim 150 advantageously provide an increased surface contact area with respective bearing surfaces 276, 278. This desirably decreases the pressure load between driving toroidal surfaces 282, 284 and the driven linear slide follower bearings 272, 274 and their respective surfaces 276, 278. The bearings 272, 274 also provide for a low friction contact with the driving toroidal surfaces 282, 284 and advantageously improve wear-resistant properties.

Figure 35:
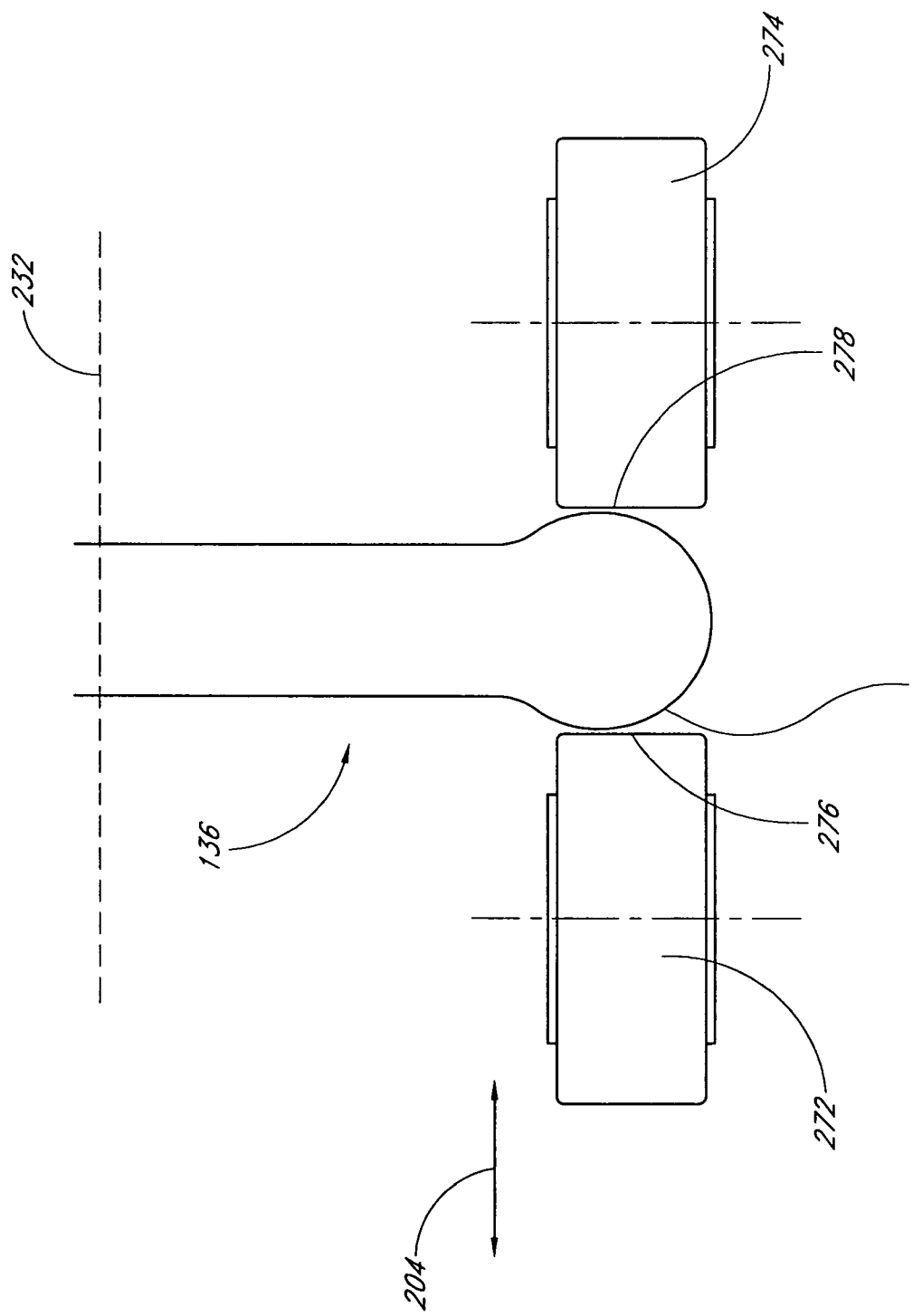
FIG. 35 is a simplified schematic view of toroid drive and associated bearings illustrating features and advantages in accordance with another embodiment of the invention.

FIG. 35 shows a modified embodiment wherein the toroid drive 136 has an outer rim 150a that substantially contacts the bearing surfaces 276, 278 mounted on the slide 138 in a low surface area or point contact arrangement. In further embodiments, the cam outer rim 150 can directly contact the slide bearing surfaces 164 and 166, as needed or desired.

Figure 36:
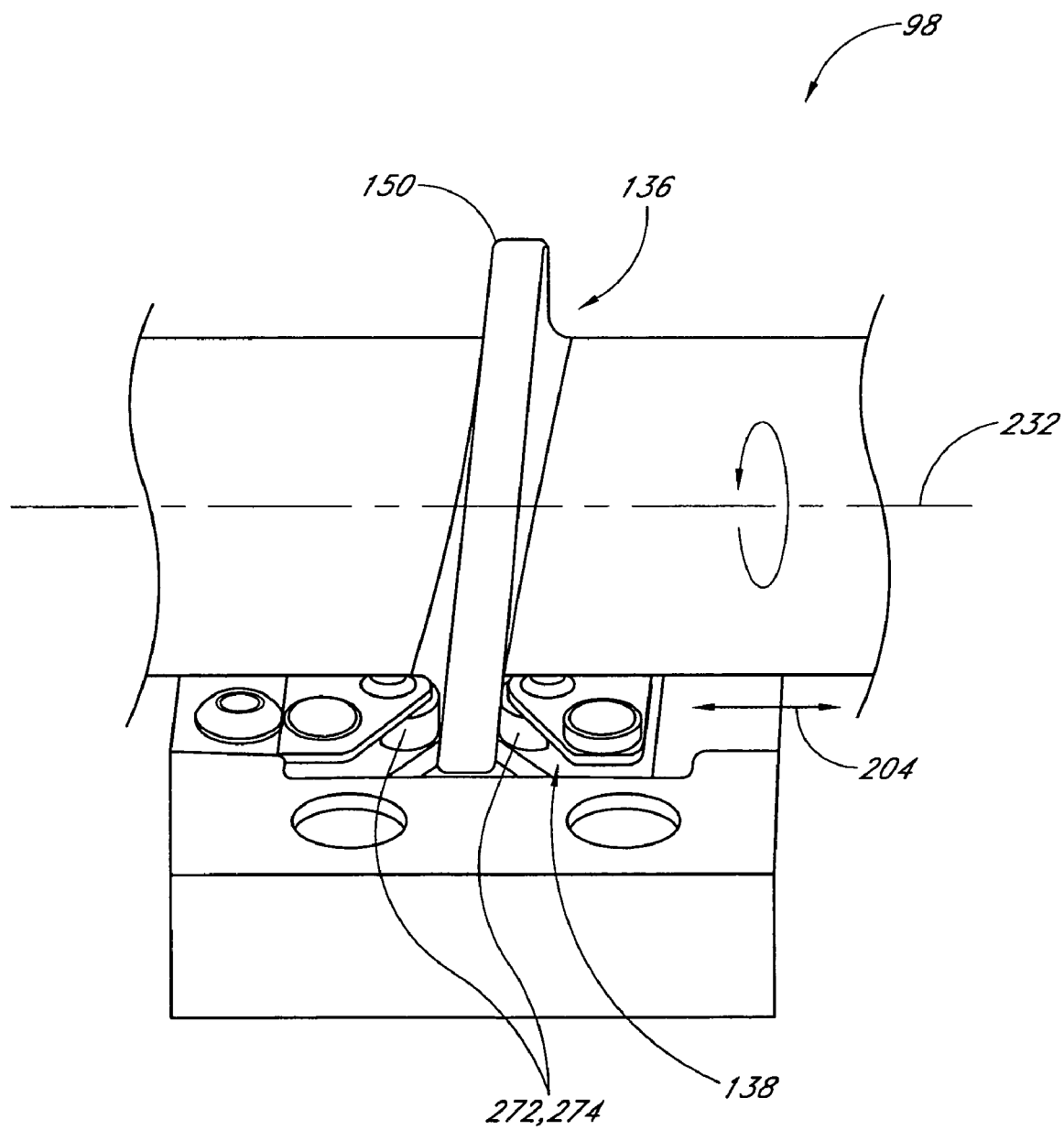
FIG. 36 is a simplified perspective view of a surgical file transmission system in a test set-up illustrating features and advantages in accordance with an embodiment of the invention.

FIG. 36 shows the operation of the toroidal transmission and power converter system 98 in a laboratory system set-up. Rotation of the toroid drive 136 is about the central rotary axis 232 is converted into linear reciprocating motion of the slide 138 as generally indicated by arrows 204. The slide is connected to the cutting blade 106. Also shown are the slide bearings 272 and 274.

Irrigation Pump System

A pulsatile water pump system 290 is incorporated into the disposable cutting blade assembly 18 and is housed within the distal cover 72. The pulsating water pump 290 supplies sterile water into a patient and in one embodiment is disposed after one use to insure no "patient to patient" bio-contamination. The pulsatile pump system of embodiments of the invention has utility in a number of fields and applications where fluid transport is desired. In one embodiment, a pulse of water is provided after each linear motion stroke.

The integrated cutting blade water pump system 290 is advantageously driven by blade motion and insures that the blade 106 will automatically be cooled and lubricated whenever the cutting blade 106 is in reciprocating motion. In modified embodiments, an external pump system may be utilized, as needed or desired.

The water pump system 290 lubricates the reciprocating blade moving parts. The water pump system 290 cools the reciprocating blade moving parts. The water pump system 290 provides clear water for optical vision capability.

The pulsating water pump system 290 more effectively clears debris from the cutting blade surface for better cutting performance by providing pulsed jets of irrigation fluid. The pulsatile water pump system 290 is driven by reciprocating cutting blade motion pumps water whenever reciprocating blade 106 is driven. In modified embodiments, the system may have a manual override feature for pump operation.

Figure 37:
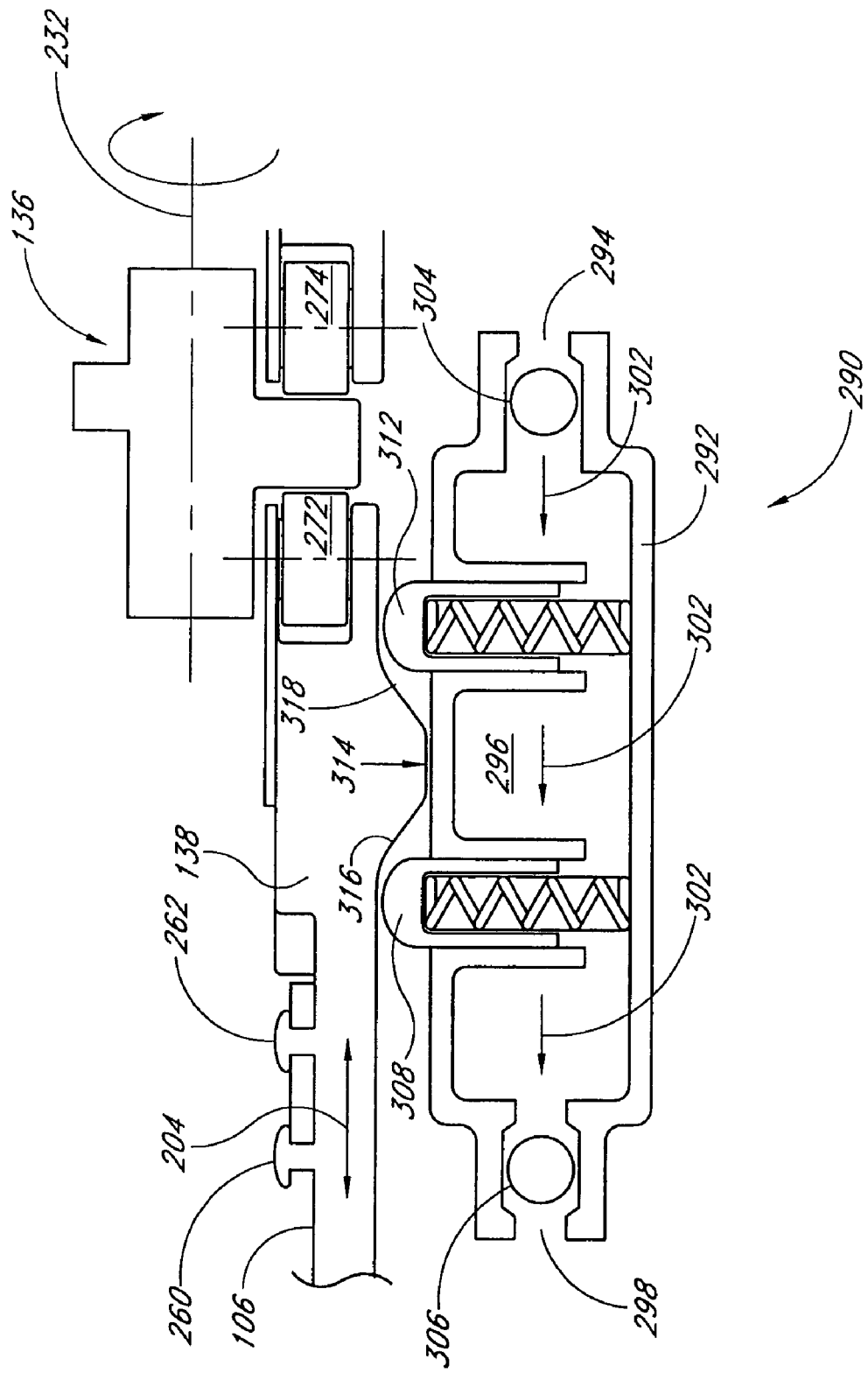
FIG. 37 is a simplified side cross-sectional view of a surgical file pulsatile pump system illustrating features and advantages in accordance with an embodiment of the invention.

FIG. 37 shows the pulsatile dual direction water pump system 290 in accordance with an embodiment. The pump system 290 has a stationary pump body 292 that includes an inlet 294, a flow chamber 296 and an outlet 298. The inlet 294 is fed water from the umbilical cord 16 or through another feedline. The outlet 298 provides water to the bearing retainer 118 within the blade shield 108. The general direction of flow or the fluid path through the pump 290 is generally indicated by arrows 302.

The inlet 294 has a one-way or check valve 304 and the outlet 298 has a one-way or check valve 306 to prevent undesired back-flow. Any one of a number of suitable valves may be used such as, but not limited to, pressure relief valves, ball-spring devices and the like.

The pump system 290 includes a pair of spaced spring-biased or -loaded plungers 308, 312. In modified embodiments, other suitable resilient biasing or loading mechanisms may be efficaciously utilized, as needed or desired. The plungers 308, 312 can move back and forth into the pump chamber 296 to selectively occlude the pump chamber 296 and/or fluid path 302 to displace fluid and pulsatingly pump it to the desired site. Water is drawn in from the inlet 294 through the valve 304 as the plungers 308, 312 move back towards their undepressed position.

The slide 138 has a lower surface 314 with a pair of specially contoured and spaced cam surfaces 316, 318 that operatively couple the slide 138 with the pump plungers 308, 312. During a forward linear stroke motion the distal cam surface 316 contacts or abuts the distal plunger 308 and depresses it to pump water out of the outlet 298. During a backward linear stroke motion the proximal cam surface 318 contacts or abuts the proximal plunger 312 and depresses it to pump water out of the outlet 298.

Thus, the reciprocating linear stroke blade drive motion moves cam surfaces 316, 318 to alternatingly depress pump plungers and thereby pump water in a pulsing modality whenever the driven cutting blade 106 is moved through a linear stroke by the transmission system 98. Desirably, the transmission system 98 provides the motion, force or energy to substantially simultaneously and synchronously drive the reciprocating blade 106 and the pulsatile pump system 290.

In embodiments of the invention, the water pump 290 is integrated into the reciprocating blade mechanism. The pulsatile (pulsating with each linear stroke) water pump feature pulses a jet of water out through the cutting blade irrigation holes 212 to keep the cutting surface 114 clean for optimum cutting action. The pulse powered pump 290 is powered by the reciprocating action of the cutting blade 106. Advantageously, this direct drive eliminates a separate pump drive source. This desirably saves parts and cost by eliminating a separate water pump.

The disposable cutting tip assembly 18 is sterile. It incorporates the water pump 290 which is also sterile. The pump 290 is very close or proximate to the site where the pressurized water is provided. Advantageously, this reduces pressure losses that would be incurred if the pump is at a distance from the point of use. It desirably also solves the problem of sterilizing a far away water pump.

When the reciprocating blade device 106 is cutting it should be provided lubrication and cooling and the cutting surface 114 should desirably also remain clean and clear of tissue debris. The water pump 290 pumps water when the cutting surface 114 is activated as the same drive mechanism drives both. Thus, an operator need not remember to activate the pump 290 since its operation is automatically actuated with cutting blade 106. Desirably, this provides a safety feature to prevent damage, galling, a freeze up and also prevents cutting debris buildup and thermal glazing.

The pump system 290 can be formed from a number of suitably durable materials. In one embodiment, the pump system 290 is formed from a suitable plastic. The plastic material may comprise a suitable thermoplastic. In modified embodiments, other suitable plastics, metals, alloys, ceramics, combinations thereof, among others, may be efficaciously utilized, as needed or desired. Suitable surface coatings or finishes may be applied, as required or desired.

The pump system 290 can be fabricated by using a number of manufacturing techniques. These include, but are not limited to, molding, machining, casting, forging, laser cutting and/or processing, laminating, adhesively fixing, welding, combinations thereof, among others, with efficacy, as needed or desired.

Figure 38:
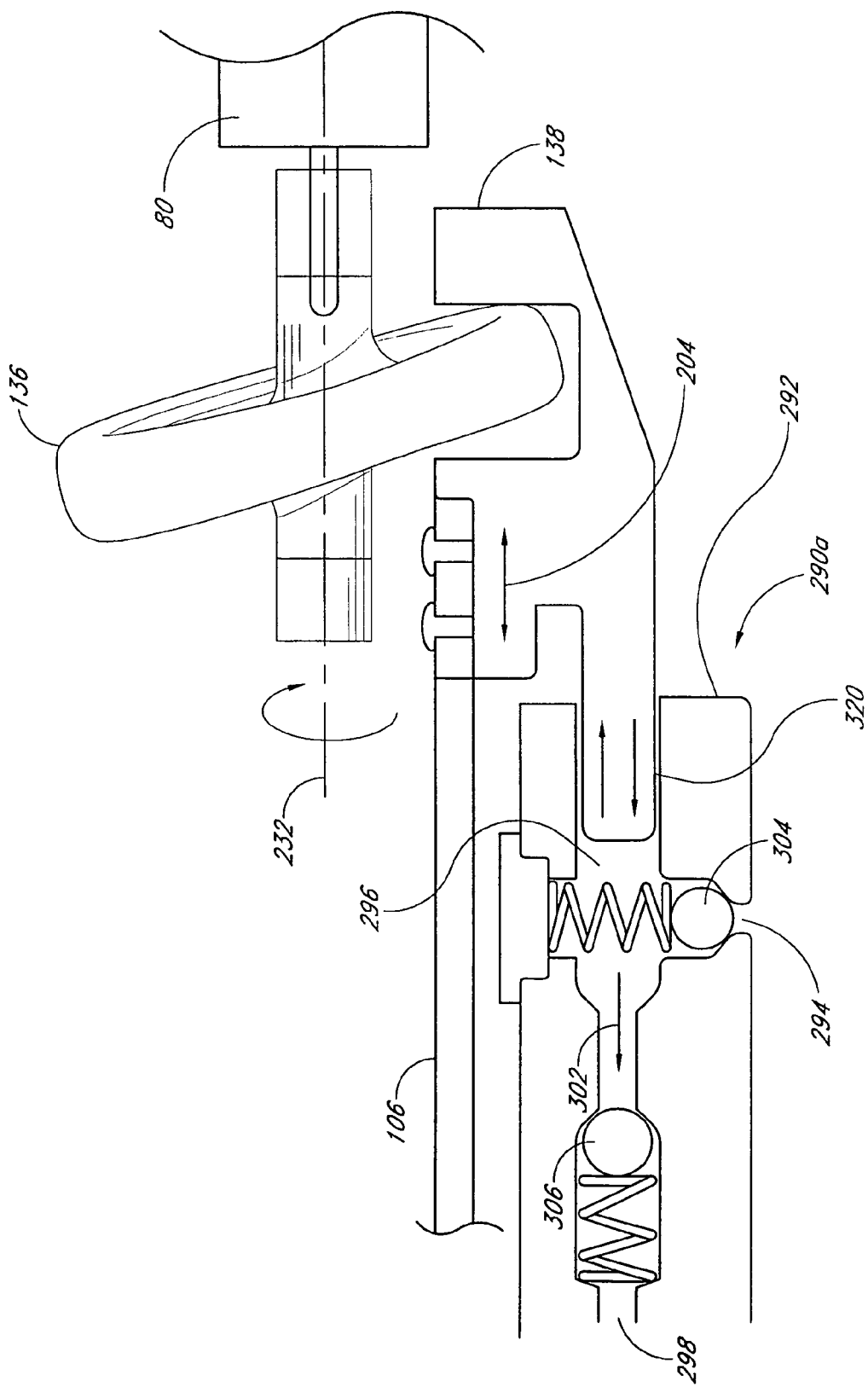
FIG. 38 is a simplified side cross-sectional view of a surgical file pulsatile pump system illustrating features and advantages in accordance with another embodiment of the invention.

FIG. 38 shows a pulsatile single direction eater pump system 290a in accordance with another embodiment. The pump system 290a includes a plunger 320 connected to the slide 138. During forward linear stroke motion the plunger 320 occludes the pump cavity 296 to displace water form the outlet 298 to the desired site. During backward linear stroke motion the plunger 320 moves in an outward direction from the pump cavity 296 and water is drawn into the cavity 296 through the inlet 294.

Powered Handpiece

Figure 39:
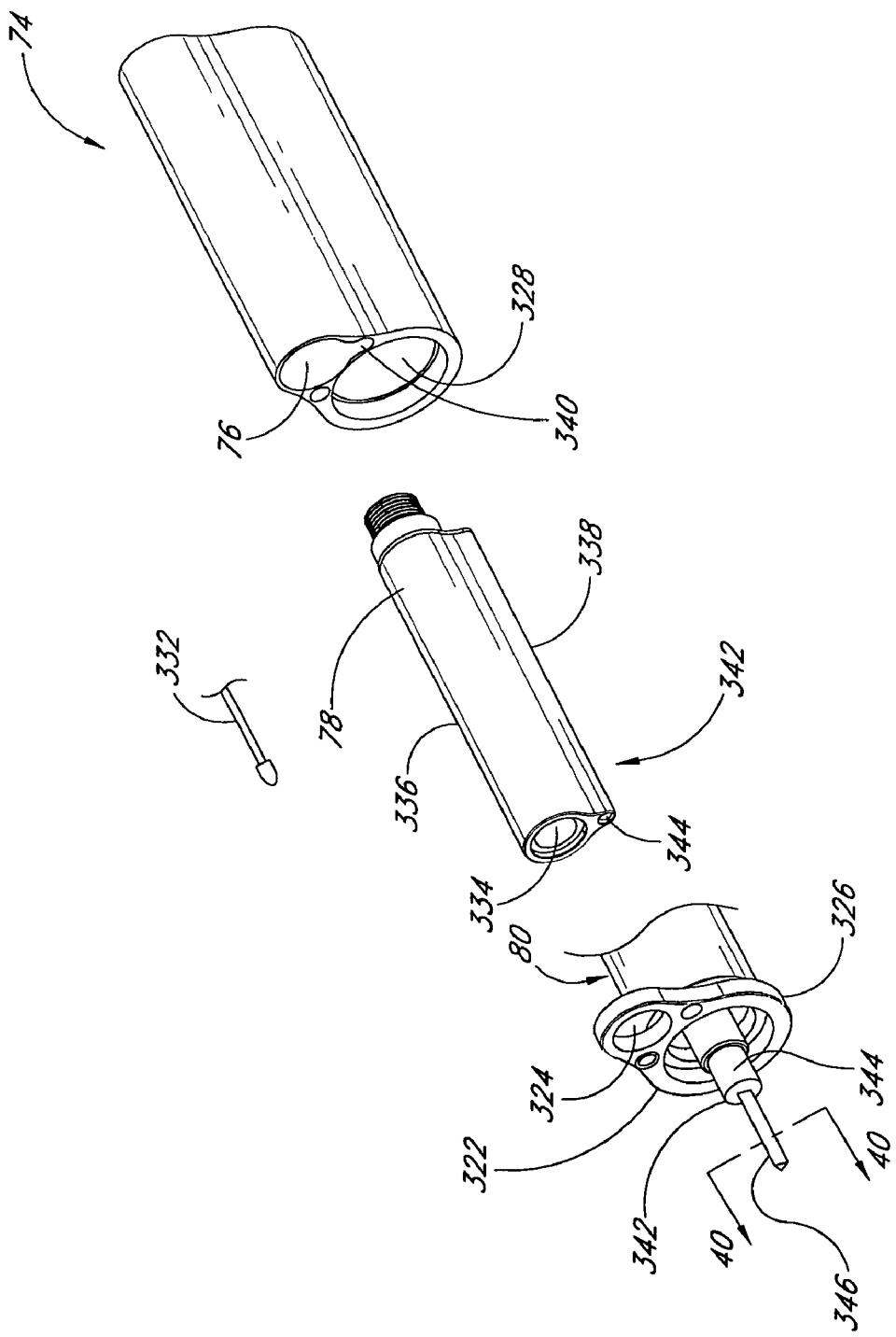
FIG. 39 is a simplified exploded perspective view of a surgical file powered handpiece illustrating features and advantages in accordance with another embodiment of the invention.

FIG. 39 shows the powered handpiece 20 including the cover or housing 74, the video camera 78, the motor assembly 80 and a distal interface member 322 for connecting to the interface member 102 and coupling 104 of the distal tip assembly 18. The interface member 322 has an opening 324 substantially aligned with the interface opening 158 which allow passage of the fiber optic probes 124, 126 for connection to the camera 78.

The proximal end 70 of the distal tip assembly 18 and the handpiece's distal end or portion 326 are configured and adapted to provide a quick and reliable connection or mating. This includes, but is not limited to, mechanical docking, electrical docking, optical docking and hydraulic docking.

The housing 74 and motor assembly 80 are steam sterilizable. The steam sterilization process involves the application of hot water and steam under pressure to kill germs followed by a partial drying process. The drying process is not always fully complete in that the instruments and parts processed, often come back partially wet. Usually there are small pockets of standing water trapped in small pools created by part shapes with water-titer pockets that end up facing upward due to there placement in the holding trays used to contain the parts and instruments to be steam sterilized.

With the routine use of steam sterilization it is desirable that any optical or electronic parts that are used with the steam sterilized instruments be designed to provide solutions to residual water and the problems it can create with electromechanical and opto-mechanical components. As discussed further below, the motor housing also houses the video camera module, which in inserted into the freshly sterilized motor housing. The hermetically sealed video camera module is designed to specifically address the specialized problems of residual water in a freshly steam sterilized surgical instrument in a sterile surgical setup environment.

The handpiece housing 74 has a motor housing 328 that receives the motor assembly 80 and the video housing 76 that receives the video camera 78. The video camera 78 is contained in the video housing 76 which provides a hermetically sealed housing. The video housing 76 desirably provides a water and gas sealed environmentally protective housing. The video camera 78 optically connects to the proximal end 70 of the distal tip assembly 18 and interfaces with the imaging fiberoptics.

The cable 16, the cover 68 and the components of the handpiece 20 are sterilizable except for the video camera 78 that is hard to sterilize. During assembly in a sterile field operating room, the non-sterile video camera 78 is inserted into a freshly sterilized handpiece housing 74. A hermetic (gas and liquid) seal is created by O-ring seals or the like. The O-rings are part of the interface at the handpiece's proximal end 330 and the distal end interface 322. Advantageously, this hardware and procedure combined together enables a non-sterile delicate electronic video camera to be made bacteriologically safe inside the sterile outer housing 74 of the sterilized handpiece 20.

The housing 74 also contains an LED illuminator 332 that connects to the illumination fiberoptics of the distal tip assembly 18. The LED (Light Emitting Diode) 332 is also mounted into the video housing 74 in a waterproof and gastight method to prevent intrusion and damage from water or water vapor accumulation. In one embodiment, a distal video imaging lens 334 is recessed to help prevent accidental damage.

The camera 78 can be provided in a mount 336 with an outer shape that is designed to prevent the incorrect insertion into the housing 74. The mount 336 has a male structure 338 that is received within a mating female receptor opening 340 within the housing 74. The male structure 338 provides the mount 336 with an asymmetrical cross sectional shape that is intended to create a visually obvious shape that can be readily inserted into its mating female receptor opening 340 in the correct or desired orientation.

In one embodiment, the camera 78 and the mount 336 comprise a video module 342 with the camera 78 housed in a waterproof and air-tight manner as discussed above in connection with the video housing 74. The hermetically sealed video module 342 can then be fitted within in the housing 74. The LED 332 can also be hermetically sealed within the module 342, for example, in an opening 344.

The camera 78 can comprise any one of a number of suitable video or digital devices. In one embodiment, the video camera 78 comprises a device as available from Toshiba. Advantageously, the integration of the video camera 78 within the handpiece greatly enhances the capability, compactness, utility and versatility of the system.

As discussed above, the sterilizable powered handpiece 20 contains a non-sterile non-sterilizable video camera 78 contained inside the sterile hand piece assembly. Advantageously, the sterile powered handpiece 20 hermetically seals the non-sterile video camera 78 in a sterile housing 74 or 336, which permits safely using the sealed assembly in the sterile field and inside a patients body.

The handpiece 20 can include one or more switches or buttons that allows the user to operably control the surgical file operation. Alternatively, or in addition, the controls can be provided on a separate platform and/or on the control system 14.

The precision motor 80 can comprise any one of a number of suitable rotary motion creating devices such as, but not limited to, gas turbines and electric motors and the like. In one embodiment, the motor 80 comprises a gas or air turbine rotary motor that is fed pressurized air or gas through the umbilical cord 16.

In one embodiment, the gas turbine motor 80 is provided air or gas at about 80 psi to run the device. In another embodiment, air or gas is provided at a pressure in the range from about 50 psi to about 100 psi, including all values and subranges therebetween. In modified embodiments, the pressure can be lower or higher, as needed or desired.

The motor assembly 80 at its distal end or portion 342 includes a rotatable power shaft 344 connected to a rotatable drive shaft 346. The motor distal end 342 docks with the proximal end 70 of the distal tip assembly 18. The power shaft 344 is generally received in the distal tip assembly holes 162, 160 and 149.

The motor 80 powers the reciprocating blade 106. The male drive shaft 346 is substantially irrotationally received within the matching female receptor hole of the drive shaft 140 to provide rotary motion to the transmission system 98 that converts it into linear reciprocating motion.

Figure 40A:
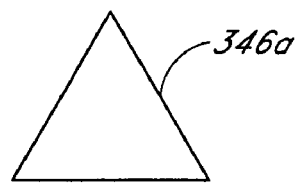
FIG. 40A is a simplified sectional view along line 40-40 of FIG. 39 illustrating features and advantages in accordance with an embodiment of the invention.

FIG. 40A shows a simple triangular shaft 346a that can engage the triangular receptor hole 254a. When the distal tip assembly 18 and the powered handpiece 20 are connected both the female triangular receptor hole 254a and the motor's male triangular drive shaft 346a can rotate in tandem. The male and female features are free to mesh and align during the axial motion of connecting the disposable cutting tip assembly 18 onto the reusable sterilizable motor handpiece 20. This docking feature has a simplified rotary triangular shaped drive shaft, even though it drives a reciprocating (push-pull) motion-cutting blade.

A triangular shaped male mating drive 346a is desirable because it facilitates sterilization of the male triangular shaft 346a. The surfaces that are steam sterilized and reused are desirably simple surfaces that are easy to wash and clean. The surfaces should also enable reliable cleaning prior to sterilization. The triangular male shaft 346a has three flat surfaces that are both easy to see and clean.

Figure 40B:
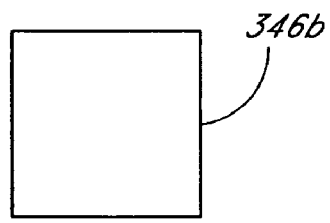
FIG. 40B is a simplified sectional view along line 40-40 of FIG. 39 illustrating features and advantages in accordance with another embodiment of the invention.
Figure 40C:
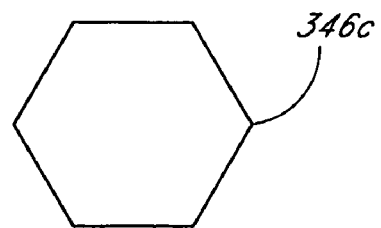
FIG. 40C is a simplified sectional view along line 40-40 of FIG. 39 illustrating features and advantages in accordance with yet another embodiment of the invention.

In modified embodiments, other suitable male-female mating drive polygonal or non-polygonal interlocking configurations may be utilized with efficacy, as needed or desired. For example, FIG. 40B shows a generally square or rectangular male shaft 346b and FIG. 31C shows a generally hexagonal male shaft 346c.

Surgical Methods

The methods which are described and illustrated herein are not limited to the sequence of acts described, nor are they necessarily limited to the practice of all of the acts set forth. Other sequences of acts, or less than all of the acts, or simultaneous occurrence of the acts, may be utilized in practicing embodiments of the invention.

The surgical instrument of embodiments of the invention enable the removal of obstructions in the tubular spaces (neuroforamen) between the vertebras of the neck and back. Desirably, this allows surgeons to navigate into the tiny (neuroforamen) canals between delicate nerve roots and remove small amounts of bony overgrowth (osteophytes) under direct vision.

Embodiments of the invention allow a surgeon to safely navigate down into the neuroforamen canal next to the nerve roots and see and remove obstructions that cause nerve compression with direct vision. The surgeons can perform a new surgical procedure, a "micro foramentomy" through as small as about a ½ inch to about 1 inch incision. This advantageously represents a truly minimally invasive surgical procedure which would serve to benefit patients and surgeons.

Figure 41:
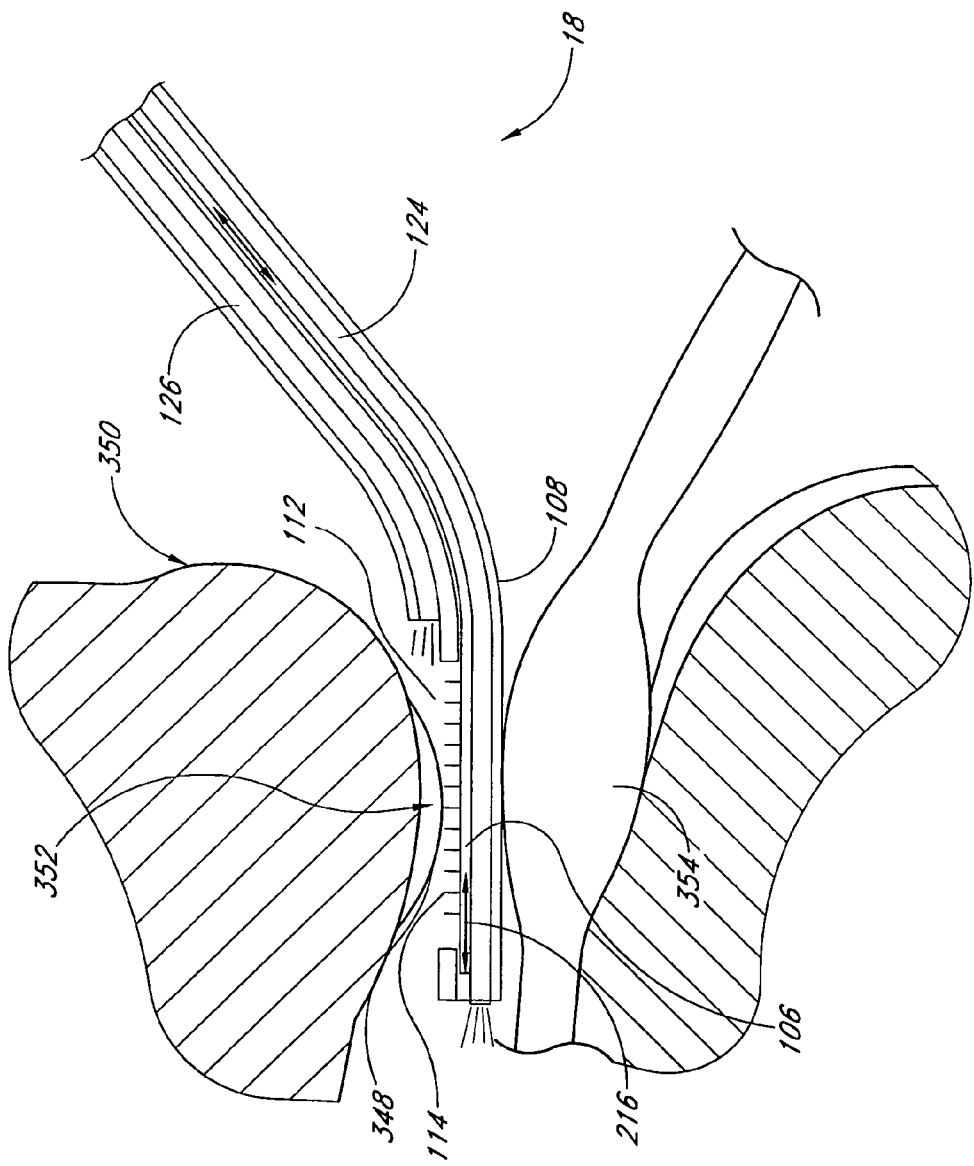
FIG. 41 is a simplified schematic view of a bone and/or tissue removal procedure illustrating features and advantages in accordance with an embodiment of the invention.
Figure 42:
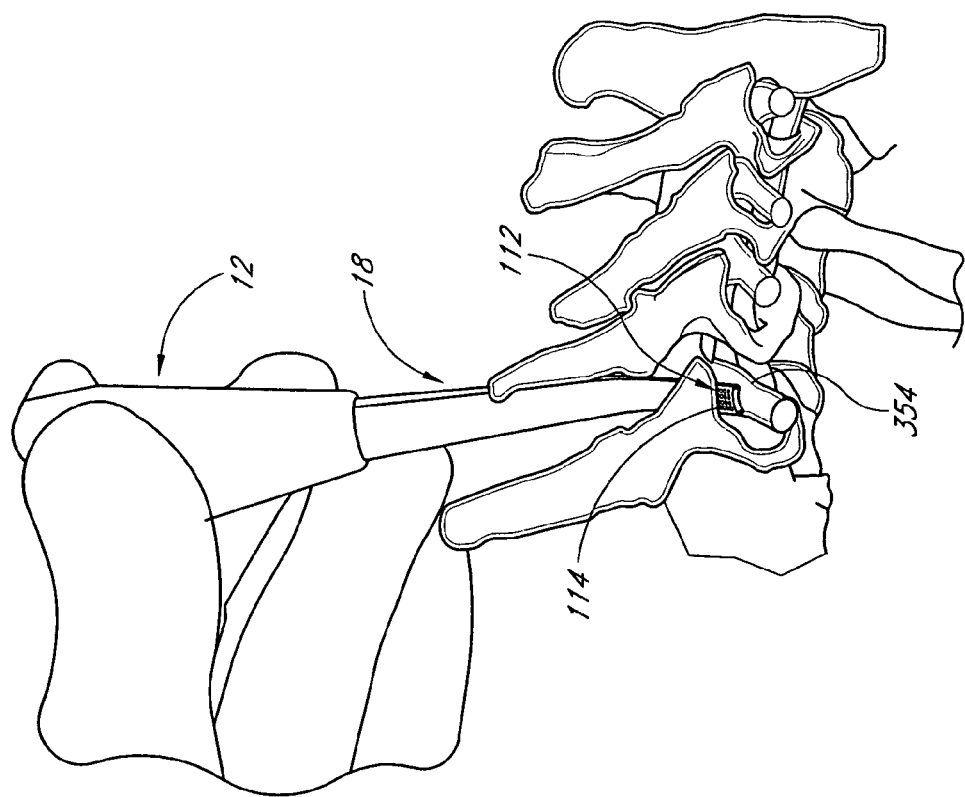
FIG. 42 is a simplified perspective view of a bone and/or tissue removal procedure on a plastic anatomical model of the human spine illustrating features and advantages in accordance with an embodiment of the invention.

FIGS. 41 and 42 show a bone and/or tissue cutting procedure using the surgical instrument 12. The shielded cutting blade 106 is inserted into a neuroforamen 348 between a vertebra 350, unwanted bone and/or tissue 352 and a nerve root 354. The shield 108 protects the nerve root 354 while the blade cutting surface 114 removes the bone and/or tissue 354 to relieve nerve compression by enlarging the neuroforamen 348.

Advantageously, embodiments of the invention provide a high level of cutting blade control and enable surgeons to reach into previously inaccessible areas to remove unwanted bone with precision, sensitivity and complete safety and confidence. The shielded cross sectional profile of embodiments of the cutting tip permit protection of delicate nerves during the neuroforamen enlargement process to relieve nerve compression.

As seen in FIG. 42, the shielded portion 108 of the file is facing the delicate nerve 354 and the opposite cutting surface 114 is facing the bone that is to be removed 352 to enlargen the bony and cartilage structural opening. Advantageously, the surgical instrument of embodiments of the invention has a cutting surface 114 that can travel around corners. A direct vision system allows surgeons to safely navigate into blind cavities of the patient's body and also assists visualization of the actual tissue cutting action and its results.

In the embodiments of a sterile disposable (one time use) cutting tip assembly 18, the cutting tip assembly 18 is used typically, in one embodiment, for about three minutes in a two-hour surgical procedure. The tip of the distal assembly 18 can provide the surgeon with a picture of the area, and enable the doctor to see the cavity and its anatomical features.

The view is magnified so the user sees a full screen image of the small tunnel, which is typically, in one embodiment, about one quarter of an inch in diameter. The enlarged view of the area allows surgeons to inspect and find the exact location and size of nerve irritation and compression, and determine where and how much bone and cartilage to remove to eliminate the nerve compression and relieve the pain.

Orthopaedic File Embodiment

Figure 43:
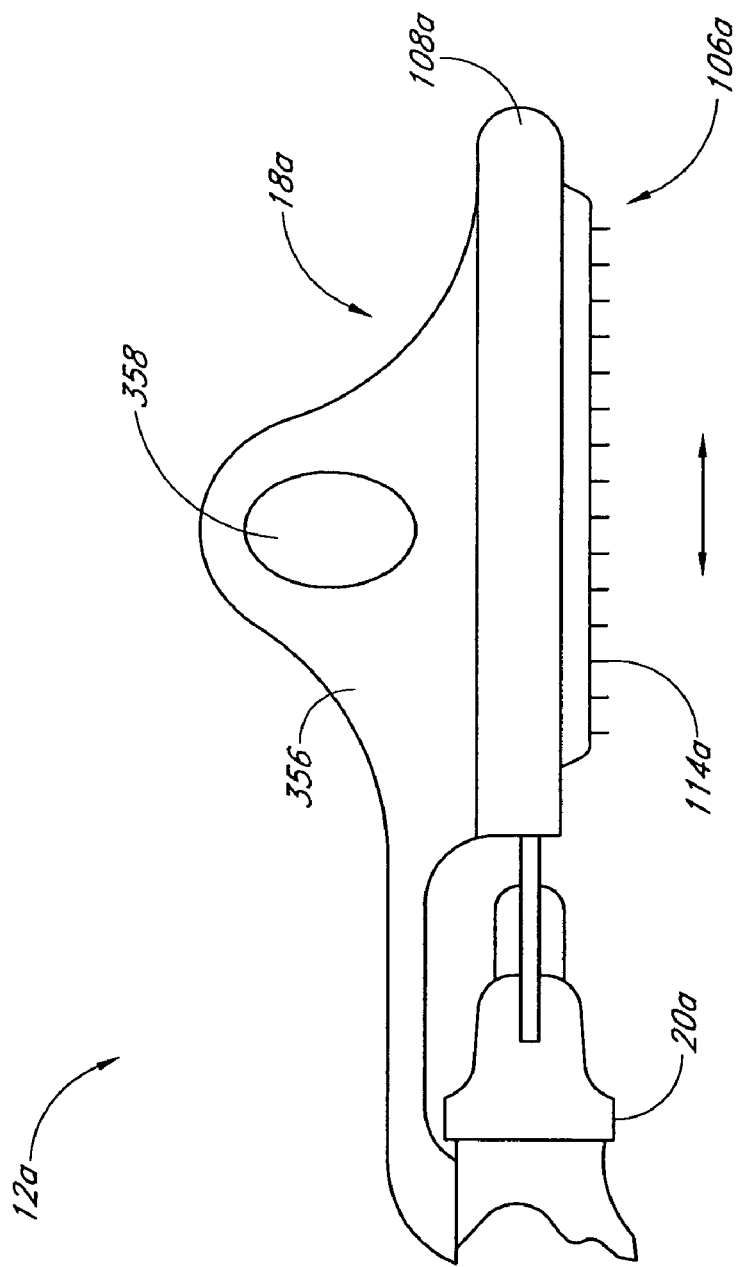
FIG. 43 simplified side view of a orthopaedic surgical file instrument illustrating features and advantages in accordance with an embodiment of the invention.
Figures 44, 45:
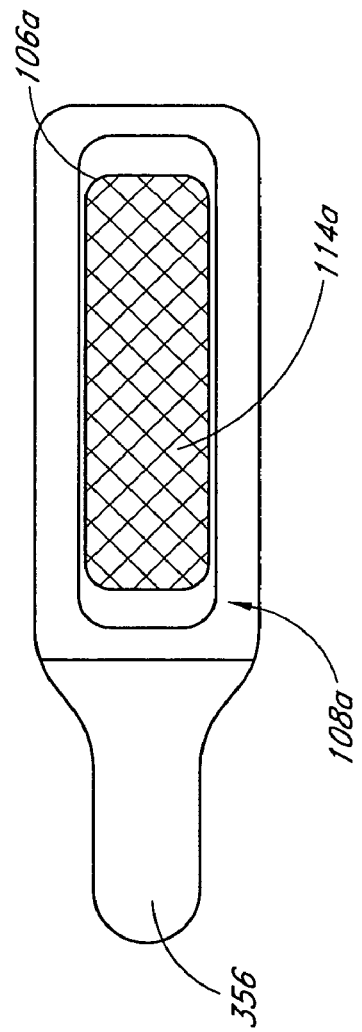
FIG. 44 is a simplified front view of a distal cutting assembly of the surgical file instrument of FIG. 43.
FIG. 45 is a simplified bottom view of the distal cutting assembly of FIG. 44.

FIGS. 43-43 show different views of an orthopaedic shielded reciprocating surgical file instrument or apparatus 12a. The surgical file instrument 12a generally comprises a distal tip assembly 18a docked to and powered by a handpiece 20a.

The distal blade assembly 18a generally comprises a reciprocating blade 106a with a cutting surface 114a and a shield or guard 108a. The cutting surface 114 has an abrasive material or abrasives 206a.

The distal blade assembly 18a further includes a handle 356 above the blade 106a. The handle 356 is used by a surgeon to press against or down on the bone and/or tissue material to be removed. The handle 356 is shaped to facilitate manipulation and has a suitable ergonomic shape or the like. The handle 356 further includes an opening 358 to facilitate operation.

From the foregoing description, it will be appreciated that a novel approach for precision bone and/or tissue removal surgery has been disclosed. While the components, techniques and aspects of the invention have been described with a certain degree of particularity, it is manifest that many changes may be made in the specific designs, constructions and methodology herein above described without departing from the spirit and scope of this disclosure.

Various modifications and applications of the invention may occur to those who are skilled in the art, without departing from the true spirit or scope of the invention. It should be understood that the invention is not limited to the embodiments set forth herein for purposes of exemplification, but is to be defined only by a fair reading of the appended claims, including the full range of equivalency to which each element thereof is entitled.

What is claimed is:

1. An apparatus for translating a rotary motion to a linear motion, the apparatus comprising:

two surfaces of two respective bearings, the two surfaces being a substantially fixed distance apart; and a cam that rotates about a central axis that is (a) substantially parallel to a direction of the linear motion of the two surfaces and (b) substantially perpendicular to a plane extending between the two surfaces;

wherein said central axis is at an angle to the plane extending between the two surfaces;

the cam having a curvilinear body of nonuniform thickness, the curvilinear body being disposed at an angle to the central axis of the cam;

wherein the curvilinear body has a shape comprising at least two toruses, the at least two toruses being partially superimposed, and each of said at least two toruses has a central axis, wherein the central axes of the at least two toruses are at an angle to each other; and wherein the body continuously contacts the two surfaces as the cam rotates about the central axis, such that the two surfaces remain at the substantially fixed distance apart as they move linearly back and forth in reciprocating motion in response to the cam's rotation about the central axis.

2. The apparatus of claim 1, wherein the plane extending between the two surfaces is generally equidistant from both of the surfaces.

3. The apparatus of claim 1, wherein the curvilinear body is disposed at an angle to the central axis of the cam of between about 10-85 degrees.

4. The apparatus of claim 1, wherein the cam body comprises first and second cam body surfaces on opposing sides of the cam body, and the first cam body surface continuously contacts a first one of the two surfaces, and the second cam body surface continuously contacts a second one of the two surfaces.

5. An apparatus for translating a rotary motion to a linear motion, the apparatus comprising:
   two surfaces that are a substantially fixed distance apart, the two surfaces connected to move with a slide that is configured for reciprocating linear movement; and
   a cam that rotates about a central axis, said central axis being at an angle to a plane extending between the two surfaces;
   the cam having a curvilinear body, the body having a non-uniform thickness, wherein the body continuously contacts the two surfaces as the cam rotates about the central axis, such that the two surfaces remain at the substantially fixed distance apart as they and the connected slide move linearly in response to the cam's rotation about the central axis;
   wherein the cam body comprises first and second cam body surfaces on opposing sides of the cam body, and the first cam body surface continuously contacts a first one of the two surfaces, and the second cam body surface continuously contacts a second one of the two surfaces.

6. The apparatus of claim 5, wherein said cam's central axis is substantially parallel to a direction of the linear motion of the two surfaces.

7. The apparatus of claim 5, wherein said central axis is substantially perpendicular to the plane extending between the two surfaces.

8. The apparatus of claim 5, wherein the two surfaces move linearly back and forth in reciprocating motion in response to the cam's rotation about the central axis.

9. The apparatus of claim 5, wherein the curvilinear body has a shape comprising at least two toruses, the at least two toruses being partially superimposed, and each of said at least two toruses has a central axis, wherein the central axes of the at least two toruses are at an angle to each other.

10. The apparatus of claim 5, wherein at least one bearing comprises the two surfaces.

11. The apparatus of claim 10, wherein two bearings respectively comprise the two surfaces.

12. The apparatus of claim 11 additionally comprising a blade connected to the slide so as to reciprocate with the slide.

13. The apparatus of claim 5, wherein the curvilinear body is disposed at an angle to the central axis of the cam.

14. The apparatus of claim 5, wherein the plane extending between the two surfaces is generally equidistant from both of the surfaces.

15. The apparatus of claim 5, wherein the central axis is disposed at an angle to the plane extending between the two surfaces of between about 5-80 degrees.

16. The apparatus of claim 5, wherein the cam body has an outer rim, and the thickness of the cam body varies about the outer rim.

17. The apparatus of claim 16, wherein the thickness of the cam body about the outer rim varies in a generally sinusoidal manner.

18. An apparatus for translating a rotary motion to a linear motion, the apparatus comprising:
   two surfaces that are a substantially fixed distance apart, the two surfaces connected to move with a slide that is configured for reciprocating linear movement;
   a cam that rotates about a central axis, said central axis being at an angle to a plane extending between the two surfaces; and
   the cam having means for continuously contacting the two surfaces as the cam rotates about the central axis, such that the two surfaces remain at the substantially fixed distance apart as they move and the connected slide linearly in response to the cam's rotation about the central axis;
   wherein the means for continuously contacting the two surfaces comprises first and second cam surfaces on opposing sides of the cam and the first cam surface continuously contacts a first one of the two surfaces, and the second cam surface continuously contacts a second one of the two surfaces.

19. The apparatus of claim 18, wherein said cam's central axis is substantially parallel to a direction of the linear motion of the two surfaces.

20. The apparatus of claim 18, wherein said central axis is substantially perpendicular to the plane extending between the two surfaces.

21. The apparatus of claim 18, wherein the two surfaces move linearly back and forth in reciprocating motion in response to the cam's rotation about the central axis.

22. The apparatus of claim 18, wherein the means for continuously contacting the two surfaces has a shape comprising at least two toruses, the at least two toruses being partially superimposed, and each of said at least two toruses has a central axis, wherein the central axes of the at least two toruses are at an angle to each other.

23. The apparatus of claim 18, wherein the means for continuously contacting the two surfaces is disposed at an angle to the central axis of the cam.

24. The apparatus of claim 18, wherein at least one bearing comprises the two surfaces.

25. The apparatus of claim 24, wherein two bearings respectively comprise the two surfaces.

26. An apparatus for translating a rotary motion to a linear motion, the apparatus comprising:
   two surfaces that are a substantially fixed distance apart, the two surfaces connected to move with a slide that is configured for reciprocating linear movement; and
   rotation means that rotates about a central axis, said central axis being at an angle to a plane extending between the two surfaces;
   wherein the rotation means is configured to continuously contact the two surfaces as the rotation means rotates about the central axis, such that the two surfaces remain at the substantially fixed distance apart as they and the connected slide move linearly in response to the rotation means that rotates about the central axis;
   wherein the rotation means that rotates about the central axis comprises first and second surfaces on opposing sides of the rotation means that rotates about the central axis, and the first surface continuously contacts a first one of the two surfaces, and the second surface continuously contacts a second one of the two surfaces.

27. The apparatus of claim 26, wherein at least one bearing comprises the two surfaces.

28. The apparatus of claim 27, wherein two bearings respectively comprise the two surfaces.

29. The apparatus of claim 26, wherein said rotation means's central axis is substantially parallel to a direction of the linear motion of the two surfaces.

30. The apparatus of claim 26, wherein said central axis is substantially perpendicular to the plane extending between the two surfaces.

31. The apparatus of claim 26, wherein the two surfaces move linearly back and forth in reciprocating motion in response to the rotation means's rotation about the central axis.

32. The apparatus of claim 26, wherein the rotation means has a shape comprising at least two toruses, the at least two toruses being partially superimposed, and each of said at least two toruses has a central axis, wherein the central axes of the at least two toruses are at an angle to each other.

* * * * *